United States Patent
Vieira Simões et al.

(10) Patent No.: US 10,377,729 B2
(45) Date of Patent: Aug. 13, 2019

(54) BIS-FURAN DERIVATIVES AS TRANSTHYRETIN (TTR) STABILIZERS AND AMYLOID INHIBITORS FOR THE TREATMENT OF FAMILIAL AMYLOID POLYNEUROPATHY (FAP)

(71) Applicant: BSIM Therapeutics, S.A., Coimbra (PT)

(72) Inventors: Carlos José Vieira Simões, Cantanhede (PT); Zaida Catarina Lourenço de Almeida, Coimbra (PT); Teresa Margarida Vasconcelos Dias de Pinho e Melo, Coimbra (PT); Rui Manuel Pontes Meireles Ferreira de Brito, Coimbra (PT); Dora Cristina Silva Costa, Coimbra (PT); Ana Lúcia Cabral Cardoso Lopes, Coimbra (PT)

(73) Assignee: BSIM Therapeutics, S.A., Coimbra (PT)

( * ) Notice: Subject to any disclaimer, the term of this patent is extended or adjusted under 35 U.S.C. 154(b) by 0 days.

(21) Appl. No.: 15/736,826

(22) PCT Filed: Jun. 15, 2016

(86) PCT No.: PCT/IB2016/053546
§ 371 (c)(1),
(2) Date: Dec. 15, 2017

(87) PCT Pub. No.: WO2016/203402
PCT Pub. Date: Dec. 22, 2016

(65) Prior Publication Data
US 2018/0208570 A1    Jul. 26, 2018

Related U.S. Application Data

(60) Provisional application No. 62/204,346, filed on Aug. 12, 2015, provisional application No. 62/180,036, filed on Jun. 15, 2015.

(30) Foreign Application Priority Data

Jun. 9, 2016 (PT) .......................... 109442

(51) Int. Cl.
*A61K 45/06*    (2006.01)
*A61K 47/54*    (2017.01)
(Continued)

(52) U.S. Cl.
CPC .......... *C07D 307/68* (2013.01); *A61K 31/341* (2013.01); *A61K 31/423* (2013.01);
(Continued)

(58) Field of Classification Search
CPC .. C07D 307/68; A61K 47/545; A61K 31/341; A61K 31/423; A61K 45/06; A61P 25/28
(Continued)

(56) References Cited

U.S. PATENT DOCUMENTS 5,284,656 A    2/1994  Platz et al.
5,451,569 A    9/1995  Wong et al.
(Continued)

FOREIGN PATENT DOCUMENTS

WO    WO 2004/093874 A1    11/2004
WO    WO 2008/124838 A1    10/2008
WO    WO-2016080853 A1  *  5/2016  ........... C07D 277/34

OTHER PUBLICATIONS

Chemical Abstracts, STN Registry database, record for RN 1156379-50-8, "5-[[(2-furanylmethyl)thio]methyl]-2-methyl-3-Furancarboxylic acid", entered into STN on Jun. 12, 2009. (Year: 2009).*
(Continued)

*Primary Examiner* — Daniel R Carcanague
(74) *Attorney, Agent, or Firm* — Wolf, Greenfield & Sacks, P.C.

(57) ABSTRACT

The design and synthesis of a novel bis-furan scaffold tailored for high efficiency at inhibiting transthyretin amy-
(Continued)

loid formation is reported. In vitro results show that the discovered compounds are more efficient inhibitors of amyloid formation than tafamidis, a drug currently used in the treatment of familial amyloid polyneuropathy (FAP), despite their lower molecular weight and lipophilicity. Moreover, ex vivo experiments with the strongest inhibitor in the series, conducted in human blood plasma from normal and FAP Val30Met-transthyretin carriers, disclose remarkable affinity and selectivity profiles. The promises and challenges facing further development of this compound are discussed under the light of increasing evidence implicating transthyretin stability as a key factor not only in transthyretin amyloidoses and several associated co-morbidities, but also in Alzheimer's disease.

21 Claims, 14 Drawing Sheets

(51) Int. Cl.
    *A61P 25/28*     (2006.01)
    *A61K 31/341*     (2006.01)
    *A61K 31/423*     (2006.01)
    *C07D 307/68*     (2006.01)

(52) U.S. Cl.
    CPC ............ *A61K 45/06* (2013.01); *A61K 47/545* (2017.08); *A61P 25/28* (2018.01)

(58) Field of Classification Search
    USPC .......................................................... 549/200
    See application file for complete search history.

(56) References Cited

U.S. PATENT DOCUMENTS

| | | | |
|---|---|---|---|
| 6,469,048 | B2 | 10/2002 | Cohen et al. |
| 7,868,033 | B2 | 1/2011 | Labaudiniere et al. |
| 2002/0137762 | A1 | 9/2002 | Joshi et al. |
| 2005/0282818 | A1 | 12/2005 | Ramesh et al. |
| 2006/0241186 | A1 | 10/2006 | Stanton et al. |
| 2010/0099683 | A1* | 4/2010 | Tomkinson .......... A61K 31/397 514/249 |

OTHER PUBLICATIONS

Chemical Abstracts, STN Registry database, record for RN 325970-36-3, "5,5'-(1,2-ethenediyl)bis[2-methyl-N-(phenylmethyl)-3-furancarboxamide]", entered into STN on Mar. 7, 2001. (Year: 2001).*
Chemical Abstracts, STN Registry database, record for RN 303065-19-2, "5,5'-[thiobis(methylene)]bis[2-methyl-3-furancarboxylic acid]", entered into STN on Nov. 16, 2000. (Year: 2000).*
International Search Report and Written Opinion for PCT/US2008/059931, dated Aug. 22, 2008.
Alhamadsheh et al., Potent Kinetic Stabilizers That Prevent Transthyretin-Mediated Cardiomyocyte Proteotoxicity. Science Translational Medicine. Aug. 24, 2011;3(97):97ra81. DOI: 10.1126/scitranslmed.3002473.
Almeida et al., Selective binding to transthyretin and tetramer stabilization in serum from patients with familial amyloidotic polyneuropathy by an iodinated diflunisal derivative. Biochemical Journal Jul. 2004;381(2):351-356. DOI: 10.1042/BJ20040011.
Alvarez-Diez et al., Mechanism-Based Inactivation of Cytochrome P450 3A4 by 4-Ipomeanol. Chem. Res. Toxicol., 2004;17(2):150-157. DOI: 10.1021/tx0341431.
Ando et al., Guideline of transthyretin-related hereditary amyloidosis for clinicians. Orphanet Journal of Rare Diseases 2013;8:31. https://doi.org/10.1186/1750-1172-8-31.
Beirao et al., Recurrence of Vitreous Amyloidosis and Need of Surgical Reintervention in Portuguese Patients With Familial Amyloidosis ATTR V30M. Retina 2011;31:1373-7. doi: 10.1097/IAE.0b013e318203c0c2.
Brain et al., Endothelin-1: demonstration of potent effects on the microcirculation of humans and other species. J Cardiovasc Pharmacol. 1989;13 Suppl 5:S147-9.
Braquet et al., Effect of endothelin-1 on blood pressure and bronchopulmonary system of the guinea pig. Journal of Cardiovascular Pharmacology Jan. 1989;13 Suppl 5:S143-6.
Brito et al., Amyloid Formation by Transthyretin: From Protein Stability to Protein Aggregation. 2003;3:349-360.
Bulawa et al., Tafamidis, a potent and selective transthyretin kinetic stabilizer that inhibits the amyloid cascade. PNAS Jun. 2012, 109 (24) 9629-9634. https://doi.org/10.1073/pnas.1121005109.
Cardoso et al., Comparative in vitro and ex vivo activities of selected inhibitors of transthyretin aggregation: relevance in drug design. Biochemical Journal Nov. 2007;408(1):131-138; DOI: 10.1042/BJ20070689.
Choi et al., Accelerated Aβ Deposition in APPswe/PS1ΔE9 Mice with Hemizygous Deletions of TTR (Transthyretin). Journal of Neuroscience Jun. 2007;27(26):7006-10. DOI: https://doi.org/10.1523/JNEUROSCI.1919-07.2007.
Coelho et al., Long-term effects of tafamidis for the treatment of transthyretin familial amyloid polyneuropathy. J Neurol. Nov. 2013;260(11):2802-14. doi: 10.1007/s00415-013-7051-7. Epub Aug. 22, 2013.
Coelho et al., Tafamidis for transthyretin familial amyloid polyneuropathy: a randomized, controlled trial. Neurology. Aug. 21, 2012;79(8):785-92. doi: 10.1212/WNL.0b013e3182661eb1. Epub Jul. 25, 2012.
Costa et al., Transthyretin binding to A-Beta peptide—Impact on A-Beta fibrillogenesis and toxicity. FEBS Letters, 2008;582(6):936-42. doi: 10.1016/j.febslet.2008.02.034.
Costa et al., Transthyretin Protects against A-Beta Peptide Toxicity by Proteolytic Cleavage of the Peptide: A Mechanism Sensitive to the Kunitz Protease Inhibitor. PLoS ONE 2008;3(8): e2899. https://doi.org/10.1371/journal.pone.0002899.
Faria et al., A look into amyloid formation by transthyretin: aggregation pathway and a novel kinetic model. Phys. Chem. Chem. Phys., 2015;17:7255-7263. DOI: 10.1039/C4CP04549A.
Hubbard et al., Anti-Neutrophil-Elastase Defenses of the Lower Respiratory Tract in α1-Antitrypsin Deficiency Directly Augmented with an Aerosol of α1-Antitrypsin. Ann Intern Med. 1989;111(3):206-212.
Johnson et al., Toward Optimization of the Linker Substructure Common to Transthyretin Amyloidogenesis Inhibitors Using Biochemical and Structural Studies. J. Med. Chem., 2008;51(20):6348-6358. DOI: 10.1021/jm800435s.
Klabunde et al., Rational design of potent human transthyretin amyloid disease inhibitors. Nat Struct Biol. Apr. 2000;7(4):312-21.
Krasnaya et al., A novel method of the synthesis of substituted furans with the use of acetylenic alkoxy β-ketoesters. Tetrahedron 1967;23(9):3687-3697.
Lai et al., The Acid-Mediated Denaturation Pathway of Transthyretin Yields a Conformational Intermediate That Can Self-Assemble into Amyloid. Biochemistry, 1996;35(20):6470-6482. DOI: 10.1021/bi952501g.
Lawson et al., Tetrahydrothiophene. Organic Syntheses, 1956;36:89. http://www.orgsyn.org/Content/pdfs/procedures/CV4P0892.pdf.
Maia et al., Clinical phenotypes of Cerebral Amyloid Angiopathy. J Neurol Sci. Jun. 15, 2007;257(1-2):23-30. Epub Mar. 6, 2007.
Maia et al., CNS involvement in V30M transthyretin amyloidosis: clinical, neuropathological and biochemical findings. J Neurol Neurosurg Psychiatry. Feb. 2015;86(2):159-67. doi: 10.1136/jnnp-2014-308107. Epub Aug. 4, 2014.
McCurtry et al., Renal and hepatic necrosis after metabolic activation of 2-substituted furans and thiophenes, including furosemide and cephaloridine. Toxicol Appl Pharmacol. Nov. 1977;42(2):285-300.
Mitchell et al., Hepatic necrosis caused by furosemide. Nature Oct. 1974;251:508-511. doi:10.1038/251508a0.

(56) References Cited

OTHER PUBLICATIONS

Naganawa et al., Synthetic studies on tautomycin. Tetrahedron, 1994;50:8969. DOI: 10.1016/S0040-4020(01)85365-5.

Nencetti et al., TTR Fibril Formation Inhibitors: Is there a SAR? Current Medicinal Chemistry, May 2012;19(15):2356-79. https://doi.org/10.2174/092986712800269326.

Ortore et al., Computational Studies on Transthyretin. Current Medicinal Chemistry, May 2012;19(15):2380-2387.

Palaninathan et al., Novel Transthyretin Amyloid Fibril Formation Inhibitors: Synthesis, Biological Evaluation, and X-Ray Structural Analysis. PLoS ONE 2009;4(7):e6290. https://doi.org/10.1371/journal.pone.0006290.

Penchala et al., AG10 inhibits amyloidogenesis and cellular toxicity of the familial amyloid cardiomyopathy-associated V122I transthyretin. PNAS Jun. 2013;110(24):9992-9997. https://doi.org/10.1073/pnas.1300761110.

Peterson et al., A Reactive Metabolite of Furan, cis-2-Butene-1,4-dial, Is Mutagenic in the Ames Assay. Chem. Res. Toxicol., 2000;13(7):531-534. DOI: 10.1021/tx000065f.

Petrassi et al., Structure-Based Design of N-Phenyl Phenoxazine Transthyretin Amyloid Fibril Inhibitors. J. Am. Chem. Soc., 2000;122(10):2178-92. DOI: 10.1021/ja993309v.

Pevzner et al., Synthesis and Phosphorylation of 4-Functionalized 2-tert-Butyl-3-chloromethylfurans. Russian Journal of General Chemistry, Jul. 2002;72(7):1085-1089.

Purkey et al., Hydroxylated polychlorinated biphenyls selectively bind transthyretin in blood and inhibit amyloidogenesis: rationalizing rodent PCB toxicity. Chem Biol. Dec. 2004;11(12):1719-28.

Raz et al., The Interaction of Thyroxine with Human Plasma Prealbumin and with the Prealbumin-Retinol-binding Protein Complex. The Journal of Biological Chemistry 1969;244(12):3230-3237.

Ribeiro et al., Stability of the Transthyretin Molecule as a Key Factor in the Interaction with A-Beta Peptide—Relevance in Alzheimer's Disease. PLoS ONE 2012;7(9): e45368. https://doi.org/10.1371/journal.pone.0045368.

Ribeiro et al., Transthyretin stabilization by iododiflunisal promotes amyloid-β peptide clearance, decreases its deposition, and ameliorates cognitive deficits in an Alzheimer's disease mouse model. J Alzheimers Dis. 2014;39(2):357-70. doi: 10.3233/JAD-131355.

Scott et al., Tafamidis: a review of its use in familial amyloid polyneuropathy. Drugs. Aug. 2014;74(12):1371-8. doi: 10.1007/s40265-014-0260-2.

Seidler et al., Identification and prediction of promiscuous aggregating inhibitors among known drugs. J Med Chem. Oct. 9, 2003;46(21):4477-86.

Sekijima, Recent progress in the understanding and treatment of transthyretin amyloidosis. J Clin Pharm Ther. Jun. 2014;39(3):225-33. doi: 10.1111/jcpt.12145.

Simoes et al., A novel bis-furan scaffold for transthyretin stabilization and amyloid Inhibition. Eur J Med Chem. Oct. 4, 2016;121:823-840. doi: 10.1016/j.ejmech.2016.02.074. Epub Mar. 3, 2016.

Simoes et al., Toward the Discovery of Functional Transthyretin Amyloid Inhibitors: Application of Virtual Screening Methods. J. Chem. Inf. Model., 2010;50(10):1806-1820. DOI: 10.1021/ci100250z.

Whitney et al., Benzyne-oxazole cycloadducts: isolation and retro-Diels-Alder reactions. J. Org. Chem., 1990;55(3):929-935. DOI: 10.1021/jo00290a025.

Winberg et al., Dimethylenedihydroheteroaromatic Compounds and Heterocyclophanes by 1,6-Hofmann Elimination Reactions. J. Am. Chem. Soc., 1960;82(6):1428-1435. DOI: 10.1021/ja01491a037.

\* cited by examiner

Thyroxine (T4)　　2OH-PCB80　　Iododiflunisal　　Tafamidis

Phenox　　　　　　　PCX2

A

D

BIS-FURAN DERIVATIVES AS TRANSTHYRETIN (TTR) STABILIZERS AND AMYLOID INHIBITORS FOR THE TREATMENT OF FAMILIAL AMYLOID POLYNEUROPATHY (FAP)

RELATED APPLICATIONS

This application is a national stage filing under 35 U.S.C. § 371 of international PCT application, PCT/IB2016/053546, filed Jun. 15, 2016, which claims priority to U.S. provisional applications, U.S. Ser. No. 62/204,346, filed on Aug. 12, 2015, and U.S. Ser. No. 62/180,036, filed Jun. 15, 2015, under 35 U.S.C. § 119(e), and to Portuguese application, No. 109442, filed Jun. 9, 2016, the entire contents of each of which are incorporated herein by reference.

TECHNICAL FIELD

The present disclosure relates to compound or a pharmaceutical preparation for stabilizing the protein transthyretin (TTR) and inhibiting amyloid fibril formation, and for treating, preventing, or ameliorating one or more symptoms of amyloid diseases. Furthermore, this disclosure also relates to a method for preparing said compound or pharmaceutical preparation and to a method for using such compound or pharmaceutical preparation for inhibiting the formation of TTR amyloid fibrils.

BACKGROUND ART

Transthyretin (TTR) is a homotetramer protein present in the blood plasma and cerebral spinal fluid. TTR is implicated in the formation of amyloid aggregates and deposition of amyloid fibrils, causing several pathologies in humans. The wild-type form of TTR is involved in senile systemic amyloidosis (SSA) in elders, due to deposition of amyloid mostly in the heart tissue. More than a hundred TTR variants are associated with amyloid formation and deposition of amyloid fibrils in various tissues and therefore with several familial amyloidoses, including familial amyloid polyneuropathy (FAP) and familial amyloid cardiomyopathy (FAC). In all cases, TTR aggregation seems to cause neuronal and/or cellular dysfunction by mechanisms that are not yet fully elucidated.

TTR plays a critical role in modulating the deposition of beta amyloid (Abeta) in Alzheimer's Disease. In addition, TTR stability is a key factor in TTR-Abeta interactions, which is relevant for the pathogenesis of Alzheimer's Disease. It has also been shown that administration of the TTR stabilizer iododiflunisal (IDIF) to AD/TTR$^{+/-}$ mice resulted in decreased brain Abeta levels and deposition and in improved cognitive function associated with reduced AD-like neuropathology in that particular mouse model. See, e.g., Choi et al. *J Neurosci*. 2007 Jun. 27; 27(26):7006-10; Ribeiro et al. PLoS One. 2012; 7(9):e45368; and Ribeiro et al. J Alzheimers Dis. 2014; 39(2):357-70; the entire contents of each of which are incorporated herein by reference.

Amyloid formation by TTR involves a first step wherein the native TTR tetramer dissociates to monomers with low conformational stability and increased tendency for partial unfolding. This is followed by self-assembly of partially unfolded monomers to form cytotoxic, oligomeric intermediate species, and eventually amyloid fibrils. Thus, stabilization of the native tetrameric form of TTR is a valid approach to reduce amyloid formation and can be attained by the binding of small organic molecules to tetrameric TTR.

It has been shown that thyroxine (T4) and several non-steroidal anti-inflammatory drugs (NSAIDs) bind to one or the two equivalent, funnel-shaped thyroxine-binding sites in TTR with high affinity, stabilize the tetramer and thereby prevent in vitro amyloid fibril formation. However, the use of NSAIDs in long-term treatments of TTR-amyloidoses is hindered by their poor selectivity for TTR and adverse anti-inflammatory effects. In addition, the serum concentration of T4 is relatively low (0.1 micromolar) compared to that of TTR (3.6-7.2 micromolar). Because thyroid-binding globulin (TBG) has an order of magnitude higher affinity for T4, less than 1% of TTR has T4 bound to it in the human serum.

GENERAL DESCRIPTION

The identification of novel, selective and safe TTR stabilizers capable of inhibiting amyloid formation is highly desirable. This has been illustrated by the development of tafamidis meglumine, chemical name N-methyl D-(2,3,4,5,6-pentahydroxy-hexyl)-ammonium; 2-(3,5-dichloro-phenyl)-benzoxazole-6-carboxylate, the first and only chemical entity directed to the treatment of FAP to have reached the drug market. Tafamidis meglumine demonstrated improvement of symptoms (mostly in secondary endpoints) in approximately 60% of FAP patients enrolled in an 18-month phase-III clinical trial. Therefore, one or more alternatives to tafamidis meglumine available is highly desirable.

The present disclosure provides compounds, compositions, and pharmaceutical preparations useful for inhibiting the formation of TTR amyloid fibrils. Methods for preparing such compounds, compositions, and pharmaceutical preparations are also provided. In addition, methods for using such compounds, compositions, and pharmaceutical preparations for inhibiting the formation of TTR amyloid fibrils, for example in the context of treating amyloid diseases, are also provided.

Some aspects of this disclosure provide compounds that are useful for inhibiting TTR amyloid fibril formation in vitro or in vivo, and thus can be used to treat amyloid diseases, e.g., amyloid diseases associated with transthyretin-related amyloidosis (ATTR). The compounds provided herein stabilize the tetrameric native state of the protein TTR, preventing amyloid fibril formation commonly observed when TTR is destabilized into monomers, and therefore may be used for treating amyloid diseases associated with TTR destabilization. Such compounds include the compounds described in the figures and in the text of this document.

The present disclosure relates to compounds of Formula (I):

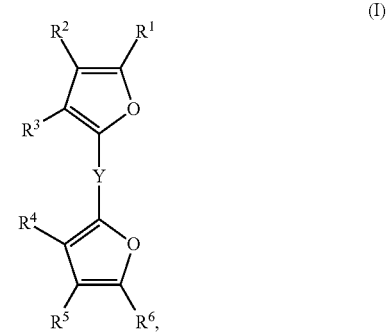

or pharmaceutically acceptable salt, solvate, hydrate, tautomer, stereoisomer, or prodrug thereof, wherein:
—Y— is —CH=CH—, —CH$_2$—CH$_2$—, or —CH$_2$—S—CH$_2$—;
R$^1$ is H or —CH$_3$;
R$^2$ is —OR$^a$, —C(=O)OR$^a$, —S(=O)2NHR$^a$, —S(=O)$_2$OR$^a$, —P(=O)NH2(OR$^a$), —C(=O)N(R$^a$)$_2$, —C(=O)NHOR$^a$, or —CHN$_4$ (tetrazolyl);
R$^3$ is H or —CH$_3$;
R$^4$ is H, —OH, Halogen, —CH$_3$, or —OCH$_3$;
R$^5$ is H, F, —CN, —SH, —OR$^a$, —C(=O)OR$^a$, —S(=O)2NHR$^a$, —S(=O)$_2$OR$^a$, —P(=O)NH2(OR$^a$), —C(=O)N(R$^a$)$_2$, —C(=O)NHOR$^a$, or —CHN$_4$ (tetrazolyl);
R$^6$ is H, —OH, Halogen, —CH$_3$, or —OCH$_3$;
each instance of R$^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted, heterocyclic ring, or substituted or unsubstituted, heteroaryl ring, or a chemical delivery system (CDS).

In an embodiment, the compound is of the formula:

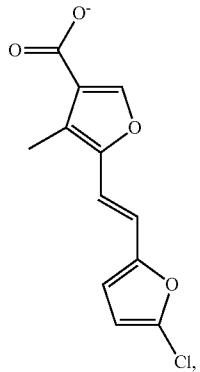 [SMILES: Cc1c(C(=O)[O-])coc1/C=C/c1ccc(Cl)o1]

or pharmaceutically acceptable salt, solvate, hydrate, tautomer, stereoisomer, or prodrug thereof, wherein the C=C double bond connecting the two furan rings is of (E)-configuration or is of (Z)-configuration.

In an embodiment, the compound is of the formula:

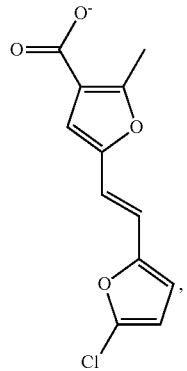 [SMILES: Cc1oc(/C=C/c2ccc(Cl)o2)cc1C(=O)[O-]]

or pharmaceutically acceptable salt, solvate, hydrate, tautomer, stereoisomer, or prodrug thereof, wherein the C=C double bond connecting the two furan rings is of (E)-configuration or is of (Z)-configuration.

In an embodiment, the compound is of the formula:

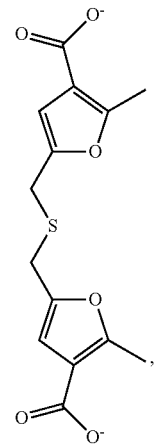 [SMILES: Cc1oc(CSCc2cc(C(=O)[O-])c(C)o2)cc1C(=O)[O-]]

or pharmaceutically acceptable salt, solvate, hydrate, tautomer, stereoisomer, or prodrug thereof.

In an embodiment, a CDS may be a molecule able to enhance the delivery of small organic molecules to the central nervous system, in particular may be able to enhance delivery of small organic molecules to the brain.

In an embodiment, any of the compounds now disclosed may comprise, may be conjugated or may be attached to a CDS, in particular the compound may be non-covalently attached to the CDS, wherein the said CDS may be 1,4-dihydroquinoline or dihydropyridine.

Some aspects of this disclosure provide pharmaceutical preparations comprising a compound as described herein, or a pharmaceutically acceptable salt, solvate, hydrate, tautomer, stereoisomer, or prodrug thereof, and a pharmaceutically acceptable carrier. Typically, the pharmaceutical preparations provided herein are suitable for administration to a human subject, e.g., in that they are sterile and essentially pyrogen-free.

In an embodiment, the pharmaceutical preparation may comprise the compound, or the pharmaceutically acceptable salt, solvate, hydrate, tautomer, stereoisomer, or prodrug thereof in an amount effective to inhibit amyloid fibril formation wherein the amyloid fibril formation may TTR amyloid fibril formation, to stabilize TTR, and/or to ameliorate at least one symptom of an amyloid disease in the subject.

In an embodiment, the pharmaceutical preparation now disclosed may comprise the compound, or the pharmaceutically acceptable salt, solvate, hydrate, tautomer, stereoisomer, or prodrug thereof, in an amount effective to decrease the level of amyloid fibril formation by at least 5%, at least 10%, at least 15%, at least 20%, at least 25%, at least 30%, at least 40%, at least 50%, at least 60%, at least 70%, at least 75%, at least 80%, at least 90%, at least 95%, at least 95.7%, at least 98%, or at least 99% in a given subject.

In an embodiment, the pharmaceutical preparation now disclosed may comprise the compound, or the pharmaceutically acceptable salt, solvate, hydrate, tautomer, stereoisomer, or prodrug thereof, in an amount effective to increase TTR stability or in an amount effective to increase serum or plasma TTR stability, or in an amount effective to increase the ratio of tetrameric TTR to monomeric TTR or in an amount effective to increase the level of tetrameric TTR in the subject and/or to decrease the level of monomeric TTR in a given subject.

In an embodiment, the pharmaceutical preparation now disclosed may comprise the compound, or the pharmaceutically acceptable salt, solvate, hydrate, tautomer, stereoisomer, or prodrug thereof, in an amount effective to increase the stability of TTR, increase the level of tetrameric TTR, decrease the level of monomeric TTR, and/or increase the ratio of tetrameric to monomeric TTR in a given subject by at least 2%, at least 2.5%, at least 3%, at least 4%, at least 5%, at least 6%, at least 7%, at least 7.5%, at least 8%, at least 9%, at least 10%, at least 12%, at least 12.5%, at least 15%, at least 20%, at least 25%, at least 30%, at least 50%, at least 60%, at least 70%, at least 75%, at least 80%, at least 95%, or at least 99% as compared to the stability, level, or ratio in the absence of the compound, the pharmaceutically acceptable salt, solvate, hydrate, tautomer, stereoisomer, or prodrug thereof.

In an embodiment, the pharmaceutical preparation now disclosed may comprise the compound, or the pharmaceutically acceptable salt, solvate, hydrate, tautomer, stereoisomer, or prodrug thereof, in an amount effective to increase the ratio of tetrameric to monomeric TTR in the subject to at least 0.72, at least 0.75, at least 0.8, at least 0.85, at least 0.9, at least 0.95, at least 0.98, or at least 0.99, and/or to maintain such a ratio in a given subject.

In an embodiment, the pharmaceutical preparation may comprise the compound, or the pharmaceutically acceptable salt, solvate, hydrate, tautomer, stereoisomer, or prodrug thereof in an amount effective to ameliorate at least one symptom of an amyloid disease in a given subject, in particular wherein the symptom is neuropathy, neurological impairment, neurological dysfunction, cognitive deficiency, nutritional deficiency, and decreased TTR stability. In an embodiment, the amyloid disease may be selected from the following list: Familial Amyloid Polyneuropathy, Familial Amyloid Cardiomyopathy, Senile Systemic Amyloidosis, or Alzheimer's Disease, AA amyloidosis, Light-Chain (AL) amyloidosis, Type-2 Diabetes, Medullary Carcinoma of the Thyroid, Parkinson's disease, Polyneuropathy, and Spongiform Encephalopathy (Creutzfeldt Jakob disease).

In an embodiment, the pharmaceutical preparation may comprise 0.1-1000 mg of the compound or the pharmaceutically acceptable salt, solvate, hydrate, tautomer, stereoisomer, or prodrug thereof per kg body weight of a given subject.

In an embodiment, the pharmaceutical preparation may be orally administered or may be in an injectable form.

In an embodiment, the pharmaceutical preparation may comprise a micronized form of the compound or of the pharmaceutically acceptable salt, solvate, hydrate, tautomer, stereoisomer, or prodrug thereof.

In an embodiment, the pharmaceutical preparation may further comprise at least one additional compound, or a pharmaceutically acceptable salt, solvate, hydrate, tautomer, stereoisomer, or prodrug thereof, wherein the at least one additional compound is a small molecule drug, a peptide drug, an interfering RNA, or an oligonucleotide, in particular an additional compound approved for therapy of an amyloid disease such as Tafamidis, Patisiran, Revusiran, Tolcapone, or Donepezil.

In an embodiment, the amyloid disease may be AA amyloidosis, Alzheimer's disease, Light-Chain (AL) amyloidosis, Type-2 Diabetes, Medullary Carcinoma of the Thyroid, Parkinson's disease, Polyneuropathy, Spongiform Encephalopathy (Creutzfeldt Jakob disease).

In an embodiment, the pharmaceutical preparation may further comprise a CDS, wherein the CDS is non-covalently attached to the compound, or to the pharmaceutically acceptable salt, solvate, hydrate, tautomer, stereoisomer, or prodrug thereof. The CDS may enhance delivery of the compound to the central nervous system, in particular the CDS may enhance delivery to the brain. Furthermore, the CDS may comprise 1,4-dihydroquinoline or dihydropyridine.

Some aspects of this disclosure provide methods for inhibiting amyloid fibril formation in a subject. The methods typically comprise administering a compound described herein, or a pharmaceutically acceptable salt, solvate, hydrate, tautomer, stereoisomer, or prodrug thereof, or a pharmaceutical preparation as described herein to a subject in need thereof.

Some aspects of this disclosure provide methods of treating an amyloid disease by administering a compound described herein, or a pharmaceutically acceptable salt, solvate, hydrate, tautomer, stereoisomer, or prodrug thereof, or a pharmaceutical preparation described herein to a subject in need thereof.

In an embodiment, the method of inhibiting amyloid fibril formation may comprise administering to a given subject a compound now disclosed, or a pharmaceutically acceptable salt, solvate, hydrate, tautomer, stereoisomer, or prodrug thereof, or the pharmaceutical preparation, now disclosed.

In an embodiment, the subject may exhibit an increased level of amyloid fibril formation, in particular transthyretin amyloid fibril formation as compared to a reference level, wherein the reference level is a level observed or expected in a healthy subject or a population of healthy subjects.

In an embodiment, the subject has or has been diagnosed with an amyloid disease, in particular a transthyretin amyloid disease.

In an embodiment, the subject has or has been diagnosed with an amyloid disease, in particular Familial Amyloid Polyneuropathy, Familial Amyloid Cardiomyopathy, Senile Systemic Amyloidosis, Alzheimer's Disease, AA amyloidosis, Alzheimer's Disease, Light-Chain (AL) amyloidosis, Type-2 Diabetes, Medullary Carcinoma of the Thyroid, Parkinson's disease, Polyneuropathy, or Spongiform Encephalopathy (Creutzfeldt Jakob disease).

In an embodiment, the method of inhibiting amyloid fibril formation now disclosed may comprise administering an amount of the compound, of the pharmaceutically acceptable salt, solvate, hydrate, tautomer, stereoisomer, or prodrug thereof, or of the pharmaceutical preparation to the subject that is effective to ameliorate at least one symptom of the amyloid disease in the subject.

In an embodiment, said method may comprise administering the compound, the pharmaceutically acceptable salt, solvate, hydrate, tautomer, stereoisomer, or prodrug thereof, or the pharmaceutical preparation at a dosage of 0.1-1000 mg of the compound or the pharmaceutically acceptable salt, solvate, hydrate, tautomer, stereoisomer, or prodrug thereof per kg body weight of the subject per day.

In an embodiment, said method may comprise administering the compound, the pharmaceutically acceptable salt, solvate, hydrate, tautomer, stereoisomer, or prodrug thereof, or the pharmaceutical preparation at a dosage effective to increase TTR stability in the subject, at a dosage effective to increase serum or plasma TTR stability in the subject, at a dosage effective to increase the ratio of tetrameric TTR to monomeric TTR in the subject and/or at a dosage effective to increase the level of tetrameric TTR in the subject and/or to decrease the level of monomeric TTR in the subject.

In an embodiment, the method now disclosed may comprise administering the compound, the pharmaceutically acceptable salt, solvate, hydrate, tautomer, stereoisomer, or prodrug thereof, or the pharmaceutical preparation at a dosage effective to increase the stability of TTR, increase the level of tetrameric TTR, decrease the level of monomeric TTR, and/or increase the ratio of tetrameric to monomeric TTR in the subject by at least 2%, at least 2.5%, at least 3%, at least 4%, at least 5%, at least 6%, at least 7%, at least 7.5%, at least 8%, at least 9%, at least 10%, at least 12%, at least 12.5%, at least 15%, at least 20%, at least 25%, at least 30%, at least 50%, at least 60%, at least 70%, at least 75%, at least 80%, at least 95%, or at least 99% as compared to the stability, level, or ratio in the absence of the compound, the pharmaceutically acceptable salt, solvate, hydrate, tautomer, stereoisomer, or prodrug thereof.

In an embodiment, the method now disclosed may comprise administering the compound, the pharmaceutically acceptable salt, solvate, hydrate, tautomer, stereoisomer, or prodrug thereof, or the pharmaceutical preparation at a dosage effective to increase the ratio of tetrameric to monomeric TTR in the subject to at least 0.72, at least 0.75, at least 0.8, at least 0.85, at least 0.9, at least 0.95, at least 0.98, or at least 0.99, and/or to maintain such a ratio in a given subject.

In an embodiment, the method now disclosed may comprise administering the compound, the pharmaceutically acceptable salt, solvate, hydrate, tautomer, stereoisomer, or prodrug thereof, or the pharmaceutical preparation in an amount effective to decrease the level of amyloid fibril formation by at least 5%, at least 10%, at least 15%, at least 20%, at least 25%, at least 30%, at least 40%, at least 50%, at least 60%, at least 70%, at least 75%, at least 80%, at least 90%, at least 95%, at least 95.7%, at least 98%, or at least 99% in a given subject.

In an embodiment, the method now disclosed may further comprise administering at least one additional compound to the subject, wherein the at least one additional compound is approved for therapy of an amyloid disease.

In an embodiment, the method now disclosed may further comprise identifying the subject as exhibiting an increased level of amyloid fibril formation as compared to a reference level or as having an amyloid disease or as being at an above-average risk of developing an amyloid disease by performing an analysis of a sample of the subject, body fluid, cell, or tissue sample, and wherein said analysis may comprise detecting the presence of amyloid fibrils, a level of transthyretin expression, and/or a mutation in the transthyretin gene in the sample, analysis of abdominal fat, and/or imaging studies of the heart of the subject.

The present disclosure also relates to a method of treating an amyloid disease, the method comprising administering to a subject in need thereof the compound or a pharmaceutically acceptable salt, solvate, hydrate, tautomer, stereoisomer, or prodrug thereof now disclosed, or the pharmaceutical preparation now disclosed.

In an embodiment, the method of treating an amyloid disease may comprise a step of administering an amount of the compound, of the pharmaceutically acceptable salt, solvate, hydrate, tautomer, stereoisomer, or prodrug thereof, or of the pharmaceutical preparation, now disclosed to the subject that is effective to ameliorate at least one symptom of the amyloid disease in the subject.

In an embodiment, said amyloid disease may be AA amyloidosis, Alzheimer's Disease, Light-Chain (AL) amyloidosis, Type-2 Diabetes, Medullary Carcinoma of the Thyroid, Parkinson's disease, Polyneuropathy, or Spongiform Encephalopathy (Creutzfeldt Jakob disease).

In an embodiment, the amyloid disease is Familial Amyloid Polyneuropathy, Familial Amyloid Cardiomyopathy, Senile Systemic Amyloidosis or Alzheimer's Disease.

In an embodiment, the method of treating an amyloid disease may comprise a step of administering the compound, the pharmaceutically acceptable salt, solvate, hydrate, tautomer, stereoisomer, or prodrug thereof, or the pharmaceutical preparation, now disclosed at a dosage of 0.1-1000 mg of the compound or the pharmaceutically acceptable salt, solvate, hydrate, tautomer, stereoisomer, or prodrug thereof per kg body weight of the subject per day.

In an embodiment, the method of treating an amyloid disease may comprise a step of administering the compound, the pharmaceutically acceptable salt, solvate, hydrate, tautomer, stereoisomer, or prodrug thereof, now disclosed or the pharmaceutical preparation at a dosage effective to ameliorate a neuropathy, neurological impairment, neurological dysfunction, or cognitive deficiency in the subject, and/or to increase TTR stability.

In an embodiment, the method of treating an amyloid disease may further comprise a step administering at least one additional compound to the subject, wherein the at least one additional compound is approved for therapy of an amyloid disease.

In an embodiment, the method of treating an amyloid disease may further comprise a step of identifying the subject as having an amyloid disease.

In an embodiment of the present disclosure, exemplary amyloid diseases that can be treated with the methods provided herein include, but are not limited to, Familial Amyloid Polyneuropathy, Familial Amyloid Cardiomyopathy, Senile Systemic Amyloidosis, AA amyloidosis, Alzheimer's Disease, Light-Chain (AL) amyloidosis, Type-2 Diabetes, Medullary Carcinoma of the Thyroid, Parkinson's disease, Polyneuropathy, and Spongiform Encephalopathy (Creutzfeldt Jakob disease), and the subject to be treated is a subject with detectable levels of amyloid fibrils, wherein the said fibrils may be detected by positron emission tomography (PET) imaging or other imaging techniques.

In an embodiment, the amyloid disease treated by the present disclosure is Familial Amyloid Polyneuropathy and the subject to be treated is any subject carrying a mutation in the TTR gene.

In an embodiment, the amyloid disease treated by the present disclosure is Familial Amyloid Polyneuropathy, in particular a TTR-related neuropathy caused by the TTR V30M variant, which is the most common amyloidogenic mutation in the TTR sequence, so far identified; and the subject to be treated is any subject carrying the TTR V30M mutation.

In an embodiment, the compounds now disclosed may stall or prevent the formation of amyloid fibrils, in particular TTR amyloid fibrils.

In an embodiment, the compounds now disclosed may stabilize the protein TTR, in particular the wild-type form of the protein TTR.

In some aspects, this disclosure provides methods for preparing the compounds and preparations described herein.

The details of one or more embodiments of the disclosure are set forth in the accompanying Figures and the Detailed Description. Other features, objects, and advantages of the disclosure will be apparent from the description and from the claims.

DEFINITIONS

The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound, of the present disclosure non-covalently associated with one or more molecules of water. Likewise, a "solvate" refers to a compound of the present disclosure non-covalently associated with one or more molecules of an organic solvent.

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "prodrug," as used herein, refers to compounds that have cleavable groups and become by solvolysis or under physiological conditions the compounds described herein, which are pharmaceutically active in vitro or in vivo; in particular it refers to an inactive conjugate that requires biotransformation before exhibiting pharmacological effects. Exemplary prodrugs include esters and/or amides of a compound provided herein, e.g., in FIG. 2, 3, or 4, that can react under biological conditions (e.g., in vitro or in vivo enzymatic conditions) to provide the parent carboxylic acid compound. In certain embodiments, a prodrug has improved physical and/or delivery properties over the parent compound. Prodrugs are typically designed to enhance pharmacologically, pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may have enhanced stability for long-term storage. See, e.g., Bundgard, H., *Design of Prodrugs*, pp. 7-9, 21-24, Elsevier, Amsterdam 1985, the entire contents of which are incorporated herein by reference.

The term "pharmaceutically acceptable carrier," as used herein, refers to one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical preparations also are capable of being commingled with the compounds of the present disclosure, and with each other, in a manner such that there is no interaction which would substantially impair the desired pharmaceutical efficacy.

The term "pharmaceutically acceptable salt," as used herein, refers to an acid or base form of a compound, usually in combination with a counter ion, that is suitable for use in pharmacy. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Pharmaceutically acceptable salts are well known in the art and are the subject of numerous reviews and monographs such as P. H. Stahl and C. G. Wermuth, editors, *Handbook of Pharmaceutical Salts: Properties, Selection and Use*, Weinheim/Zürich:Wiley-VCH/VHCA, 2002.

The terms "therapy," "therapeutic," "treat," or "treatment" refer to, but are not limited to, one or more clinical intervention with an intent to prevent, ameliorate, or cure a condition or symptoms of the condition in a subject.

BRIEF DESCRIPTION OF THE DRAWINGS

The following figures provide preferred embodiments for illustrating the description and should not be seen as limiting the scope of disclosure.

DETAILED DESCRIPTION

Figure 1:
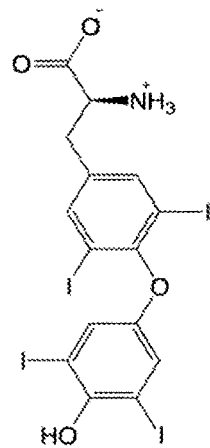
FIG. 1—Chemical formulae of compounds used as reference in this work (upper row), and compounds used as template or query for virtual screening in previous work (lower row). Thyroxine (T4) is a thyroid hormone and the endogenous transthyretin ligand; 2OH—PCB80 is a pollutant and one of the most active TTR stabilizers; iododiflunisal (IDIF) is a derivative of diflunisal, one of the few compounds to have reached clinical trials for the treatment of familial amyloid polyneuropathy (FAP); tafamidis is the only drug available for the treatment of FAP. Phenox is a potent TTR amyloid inhibitor, designed by structure-based methods; PCX2 is a modeled, hypothetical compound inspired by phenox and other potent inhibitors like 2OH—PCB80.
Figure 1:
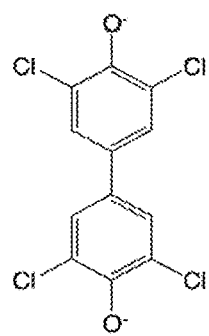
Figure 1:
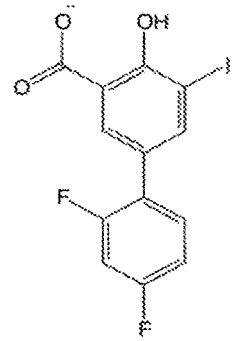
Figure 1:
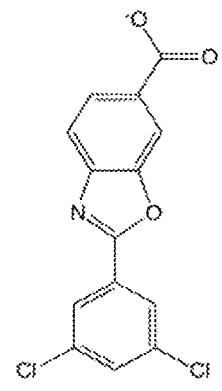
Figure 1:
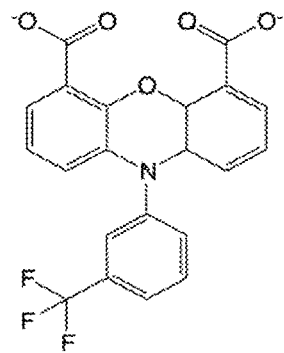
Figure 1:
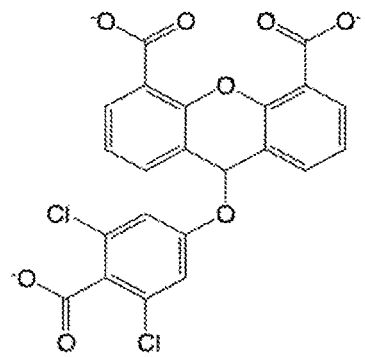

The present disclosure relates to a compound or a pharmaceutical preparation for stabilizing the protein transthyretin (TTR) and inhibiting amyloid fibril formation, and for treating, preventing, or ameliorating one or more symptoms of amyloid diseases. Furthermore, this disclosure also relates to a method for preparing said compound or pharmaceutical preparation and to a method for using such compound or pharmaceutical preparation for inhibiting the formation of TTR amyloid fibrils.

Protein aggregation and deposition are important pathological hallmarks in neurodegenerative diseases like Alzheimer's, Parkinson's and Huntington's disease, a field overwhelmed by failure of compounds targeting amyloid plaques [1]. Remaining traces of skepticism surrounding the role of amyloids in disease, the so-called "amyloid hypothesis", may have been shaken when Biogen presented, in March 2015, the results of its phase 1b study with adu-canumab, an antibody that binds to deposits of the amyloid-β (Aβ) peptide that is strongly implicated in Alzheimer's disease (AD). Aducanumab dose-dependently reduced amyloid deposits in six cortical regions of the brain and, apparently, the higher the dose the better AD patients performed on cognitive tests [2].

Such findings are already fuelling a new impetus in the field of drug discovery for protein misfolding neurodegenerative diseases (PMNDs), with pharmaceutical companies like Janssen and Eli Lilly bolstering their interest in pushing AD treatments (e.g. Lilly's solanezumab) to the market. In parallel, new approaches aiming at stabilizing non-pathogenic protein states to prevent amyloid formation or at manipulating proteasomal and autophagic pathways to clear intracellular protein aggregates may gain additional impetus.

Familial amyloid polyneuropathy (FAP) is a rare, neurodegenerative, amyloid disease caused by mutations in the protein TTR and characterized by progressive peripheral and autonomic polyneuropathy, starting with loss of temperature and pain sensation on the lower limbs and evolving to severe autonomic dysfunction, usually resulting, if untreated, in the death of patients 10-15 years after the onset of the first symptoms. FAP is associated with the formation and deposition of amyloid aggregates and fibrils, mainly by variants of TTR. TTR is a homotetrameric protein that circulates in the plasma and in cerebrospinal fluid, being produced in the liver, the choroid plexus and the pigment epithelium of the eye's retina. The formation of amyloid by TTR is triggered by dissociation of the native tetrameric form, yielding monomeric species with low conformational stability and high tendency to aggregation [3]. At present, more than 100 amyloidogenic mutations in the TTR sequence have been identified, but the most common form of TTR-related neuropathy is caused by the TTR V30M variant.

Liver transplantation (LT) was the standard treatment option for FAP for nearly two decades. LT halts progression of clinical symptoms by replacing the disease-associated TTR allele with a wild-type allele. Although LT has been successfully employed in the treatment of FAP cases [4], its use is far from ideal due to its invasive nature, scarcity of donors, the required long-term post-transplantation immunosuppressive therapy, the high costs involved, and the significant number of patients that are not eligible because of their state of disease progression.

Tafamidis meglumine (brand name Vyndaqel) reached the European drug market as the first drug therapy directed to the treatment of FAP. As a pioneering drug, tafamidis has shown that stabilization of the native tetrameric form of TTR by molecules endowed with chaperone-like activity is a viable approach to prevent (or at least stall) the formation of amyloid aggregates and fibrils, thus delaying disease progression [5]. Tafamidis demonstrated improvement of symptoms in approximately 60% of FAP patients enrolled in an 18-month phase-III clinical trial and was approved in Europe and Japan for treatment of adult FAP patients showing early symptoms of polyneuropathy [6,7]. Patients treated with tafamidis in clinical trials showed some preservation of function and had less neurological deterioration [8]. The reduced rate of neurologic deterioration was sustained throughout a 12-month extension study, totaling 30 months of treatment [9].

The need for more efficacious solutions to the treatment of FAP, and principally of non-responsive FAP patients, is well mirrored in the development of two alternative technologies based on small interference RNAs and silencing oligonucleotides, both aiming at knocking down TTR expression by the liver. Just like with LT, however, these treatments do not eschew the synthesis of mutant TTR by the choroid plexus and the eye's retina [10]. Indeed, clinical manifestations with involvement of the central nervous system (CNS) have been reported in FAP patients with prolonged periods of disease progression [11]. Studies conducted by Maia et al. have shown that CNS TTR amyloidosis was already present 3 years after polyneuropathy onset and progressed from the meninges and its vessels towards meningocortical vessels and the superficial brain parenchyma, as disease duration increased [11]. Amyloid deposition in cerebral blood vessels of FAP patients shows remarkable resemblance with what is observed in cases of Cerebral Amyloid Angiopathy (CAA) of Alzheimer's patients. CAA encompasses a large spectrum of clinical phenotypes, including ischemic events and microbleeds [12], that are now being witnessed in FAP patients. These CNS manifestations should be given serious consideration, as it may be expectable that more than 2000 post-transplant FAP patients will develop CNS amyloidosis in the near future.

The importance of TTR stabilization in several target organs, tissues or compartments, other than the blood plasma, may extend beyond the amyloidogenic nature of this protein. There is a compelling amount of biochemical and in vivo data suggesting that TTR may play a neuroprotective role by modulating Aβ aggregation. TTR-Aβ interactions were characterized by Costa et al., who showed that TTR is capable of interfering with Aβ fibrilization by both inhibiting and disrupting fibril formation [13]. These authors also proposed that TTR, either recombinant or isolated from human sera, can proteolytically process Aβ, generating smaller and less amyloidogenic new peptides and enabling cells to eradicate them [14]. Furthermore, Ribeiro et al. were able to reveal discrepancies in the interaction of different TTR variants with Aβ, prompting TTR stability as a key factor in TTR-Aβ interactions [15]. They also demonstrated that administration of the compound iododiflunisal, a known TTR stabilizer, in AD/TTR+/− mice resulted not only in decreased brain Aβ levels and deposition but also in improved cognitive function associated with AD-like neuropathology in that particular mice model [16].

Small-molecule therapeutics still represents one of the most versatile options when attempting to meet the requirements of multiple target-product profiles, including, for example, the ability to cross the blood-brain barrier. The present disclosure describes the design and synthesis of novel organic compounds aimed at the inhibition of amyloid formation by TTR. The new compounds address an enduring issue of ligand efficiency in binding to TTR thyroxine-binding sites, inherent to the protein's natural preference for heavily halogenated biaryl moieties. Besides being capable of inhibiting amyloid formation in vitro in greater extent than tafamidis, the compounds now disclosed show promising thyroxine competition and selectivity profiles in blood plasmas from normal and TTR V30M carriers. At the current stage of optimization, the compounds may be tailored for the treatment of multiple TTR-related indications.

Nencetti and Orlandini examined hundreds of structurally different TTR amyloid inhibitors discovered over the past decade, offering a comprehensive review of their most relevant chemical classes [17]. This report shows that, even though the majority of TTR ligands was derived using structure-based design principles, the biaryl scaffold is the most common, unifying feature of the compounds—be they early analogues of thyroxine (represented in FIG. 1) and non-steroidal anti-inflammatory drugs (NSAIDs), natural polyphenols, non-natural (and rationally-designed) inhibitors or more exotic bivalent binders [17]. Only more recently, compounds presenting only one aromatic portion and escaping the typical halogenated biaryl of the NSAID pharmacophore have been reported [18,19].

In line with previously reported screening strategies [20], tuning and testing of the virtual screening (VS) performance of several receptor- and ligand-based methodologies were carried out, as well as combinations of both. Some of the most promising VS workflows were implemented on a small computer cluster and several VS campaigns have been conducted ever since. Thus far, 82 virtual screening hits have been purchased from various chemical vendors and/or synthesized in the lab, of which 26 have been confirmed experimentally as TTR amyloid inhibitors—reducing amyloid formation in vitro to less than 50% at protein-ligand concentration ratio of 1:2. Of these, 14 compounds were considered good inhibitors, reducing amyloid formation to less than 10% at a protein-ligand concentration ratio of 1:2, and 6 compounds were considered excellent inhibitors, displaying inhibitory activity superior to the drug tafamidis.

More than looking for active or very active compounds, the focus of the analysis of the screening hits has been centered on identifying novelty and efficient scaffolds (scaffold hopping). The intent and scope of this contribution is not to provide a detailed validation of the in silico approaches to the screening of TTR amyloid inhibitors, but to report the discovery of a promising new scaffold that may hold potential for progression into advanced lead optimization.

A virtual chemical library containing 2,259,573 compounds was assembled by filtering of an original set comprised of 10,962,930 molecules deposited in the ZINC database (2008 version), as described in [20]. The filtering criteria included a set of predefined rules for drug-likeness and bioavailability, as well as rules derived from analysis of physicochemical properties of known TTR stabilizers. The used pharmacokinetic predictors included Lipinski's rule-of-five [22], allowing up to two violations and defining hydrogen-bond donors and acceptors as outlined in the work of Mills and Dean [23], Veber's (GSK) rules [24], Martin's (Abbott) bioavailability score [25], and Pharmacopeia's "Egan egg" bioavailability rule [26]. Aggregators are small molecules respectively known or predicted to aggregate and sequester protein in solution, thus interfering with biochemical assay results [27,28]. Compounds classified or predicted as "aggregators" were filtered out. Molecules predicted insoluble or poorly soluble in water were also discarded.

Figure 2:
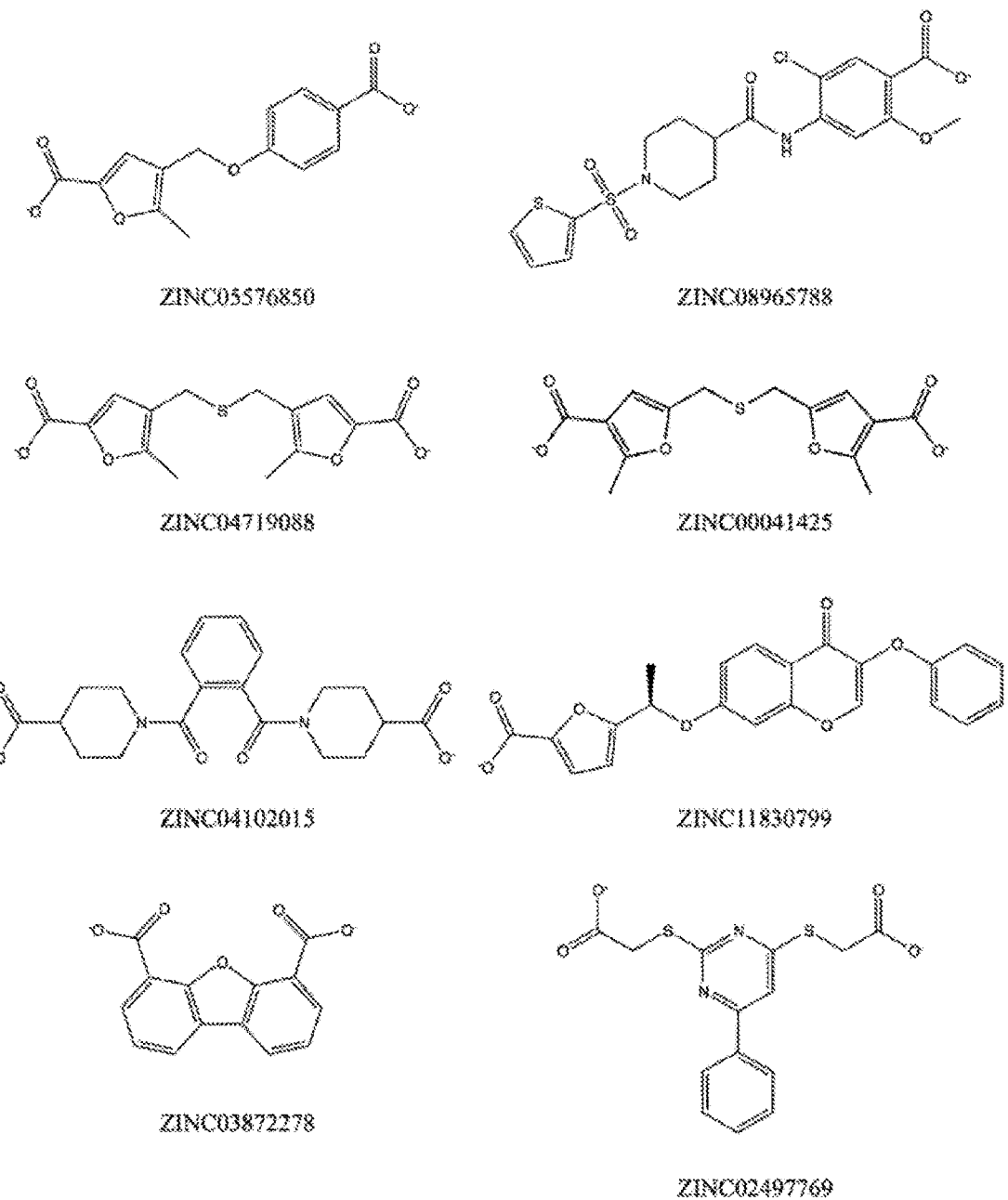
FIG. 2—Chemical formulae of the top-8 screening hits predicted as soluble or very soluble and selected through the virtual screening protocol leading to the discovery of compound bis((3-carboxy-2-methyl-furan-5-yl)methyl)sulfane (ZINC00041425, AT09-A00). AT09-A00 is ranked fourth and was the only compound meeting all requirements set for prioritization for biochemical evaluation.

Compound bis((3-carboxy-2-methyl-furan-5-yl)methyl) sulfane (AT09-A00), shown in FIG. 2, was the ninth compound in a first batch of 12 virtual screening hits acquired from various suppliers to be experimentally tested for amyloid inhibition activity. Prioritization of AT09-A00 was accomplished via in silico screening of the tailored library. A ligand-based VS protocol employing the template compound PCX2 as query (FIG. 1) was chosen for screening, based on its overall VS performance and, most importantly, on its high early recovery rate [20]. PCX2 is a bulky hypothetical compound (a concatamer), modelled on top of phenox (FIG. 1) [29] to gather key pharmacophoric features of multiple TTR stabilizers in a single VS query. Such bulkiness may negatively impact compounds with an entropic penalty in binding to the T4 sites of TTR, but the chosen ranking function scored ligand conformations by similarity in chemical features rather than similarity in shape.

The top-ranked thousand compounds retrieved by the chosen VS protocol were further filtered using tighter criteria for physicochemical and pharmacokinetic predictors. For example, the maximum calculated octanol-water partition coefficient allowed was set to 3.5. Subsets comprised by the top 100 compounds predicted to be soluble, very soluble or highly soluble were assembled. The structural alignment of each compound against the chosen template molecule was visually inspected, with emphasis on the analysis of the overlapping of chemical/pharmacophoric features. Furthermore, all top ranked compounds were docked into the T4-binding sites of TTR using the program AutoDock4 [30] and its built-in free energy scoring function. This software has been extensively tested through redocking studies with TTR X-ray structures [20]. The structures of TTR in complex with flufenamic acid (1BM7) and 2OH—PCB80 (Protein Data Bank entry 2G5U; see FIG. 1) were selected for providing reliable pose predictions against a variety of ligands, as concluded through the crossdocking studies reported in reference [20]. Visual inspection of the docked poses for each of the top hundred (predicted soluble) compounds allowed for a final selection of virtual screening hits to be acquired from chemical suppliers and experimentally evaluated through a biochemical assay described below. In this work, only compounds showing an appropriate (predicted) binding mode within TTR's T4-binding sites were selected.

AT09-A00 was discovered at the sixth entry of the ranked chemical library, holding ZINC code 00041425. Filtering of the top thousand VS hits using the stricter physicochemical property criteria for solubility placed ZINC00041425 on the fourth position of the rank. FIG. 2 reveals the top 8 compounds predicted "soluble" or "very soluble" selected by the chosen VS protocol. Interestingly, compound ZINC03872278 (dibenzofuran-4,6-dicarboxylic acid), ranked tenth across the entire chemical library (and seventh amongst the soluble hits), has been reported as a strong TTR binder (PDB entry 1DVU and reference [31]). It was discarded due to lack of novelty. Visual inspection of ligand poses generated by a docking methodology carefully validated for TTR [20], based on AutoDock4 [30], helped us discarding five hits (ZINC08965788, ZINC04102015, ZINC11830799, ZINC06627939 and ZINC06022431, represented in FIG. 2) due to inappropriate length for TTR's T4 binding sites. Amongst the top 8 screening hits retrieved by the selected VS protocol, compounds ZINC05576850, ZINC04719088, ZINC00041425 and ZINCO2497769 (FIG. 2) were selected for biochemical evaluation. However, only compound bis((3-carboxy-2-methyl-furan-5-yl)methyl)sulfane, ZINC00041425, fulfilled the criteria, namely availability in shelf, set for acquisition from a chemical supplier during the screening stage.

Amongst the top-ranked compounds retrieved by the virtual screening run, the furan moiety, present in compounds positioned in the first, third, fourth and sixth entries of the ranked VS library (respectively ZINC05576850, ZINC04719088, ZINC00041425 and ZINC11830799; see FIG. 2), caught the attention for its novelty, even within the context of TTR ligands bearing five-membered rings [17]. Furan is an interesting heteroaromatic ring with a planar geometry, being relatively nonreactive under most conditions of pharmaceutical development.

Figure 3:
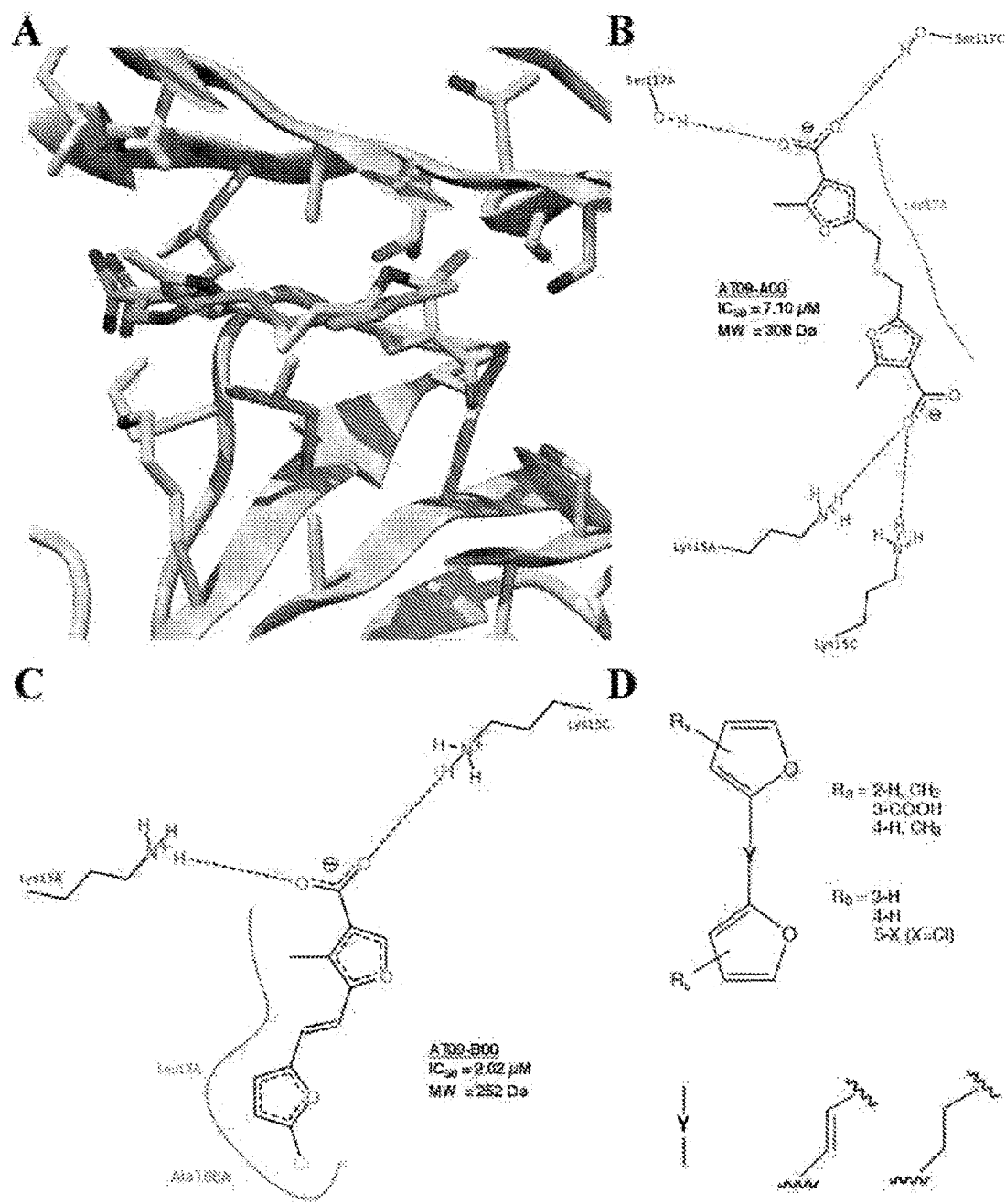
FIG. 3—Early ligand optimization studies conducted on bis-furan compounds. The representations include: a three-dimensional structure of one of the two TTR binding sites showing docked ligand poses of the screening hit AT09-A00, in lighter grey, and the optimized derivative AT09-B00, in darker grey (A); two-dimensional diagrams describing TTR:AT09-A00 interactions (B) and TTR:AT09-B00 interactions (C); a summary of the chemical formulae of exemplary relevant bis-furan compounds considered in this work (D). Panel A was prepared using Chimera, whereas panels B and C were produced with PoseView, integrated in the LeadIT package.

The molecular docking protocol mentioned in the previous subsection and validated in reference [20] was explored to predict the putative binding mode of AT09-A00 to TTR T4-binding sites. FIG. 3 (panels A and B) illustrates the results of such studies. With its highly flexible linker connecting the two furan moieties, this screening hit explores several distinct poses within TTR binding site, some of which may result in favorable interactions with the protein: the negatively charged carboxyl group in one furan ring may interact with the positively-charged side chains of the two Lys-15 residues located at the entrance of TTR binding sites (at ca. 2.5 Å distance), whereas the corresponding group of the second furan ring may act as hydrogen-bond acceptor for the hydroxyl side chains of two Ser-117 residues situated at the inner portion of the binding sites (equally at ca. 2.5 Å distance). Given the high flexibility of the linker, it is also possible that the oxygen atom of the furan ring placed at the inner portion of TTR binding sites may work as a hydrogen bond acceptor for the hydroxyl group of the side chain of Thr-119 residues (at ca. 4 Å distance).

Considering such richness of complementary features between TTR binding sites and AT09-A00, together accounting for a favorable enthalpic contribution to the ligand-protein association, it has shown that the high flexibility of the linker could bring about an important conformational entropy penalty to binding. Therefore, defining the best possible linker strategy was at the center of attention when designing the first optimized bis-furan derivative.

In an embodiment, the linker optimization was conducted as follows. The funnel-like shape of TTR binding sites plays an important role in the binding of small organic molecules to the protein. The majority of TTR stabilizers and amyloid inhibitors identified to date are rigid molecules, with the two typical aryl groups connected by a single bond, as in 2OH—PCB80 (still one of the most potent inhibitor known to date) [32] and tafamidis (the available drug treatment for FAP) [33], or by rigid, unsaturated linkers, as in stilbenoid compounds [31]. In fact, this was proposed to be at the basis of the high potency of resveratrol, a natural antioxidant, at preventing amyloid formation by TTR [31].

Figure 4:
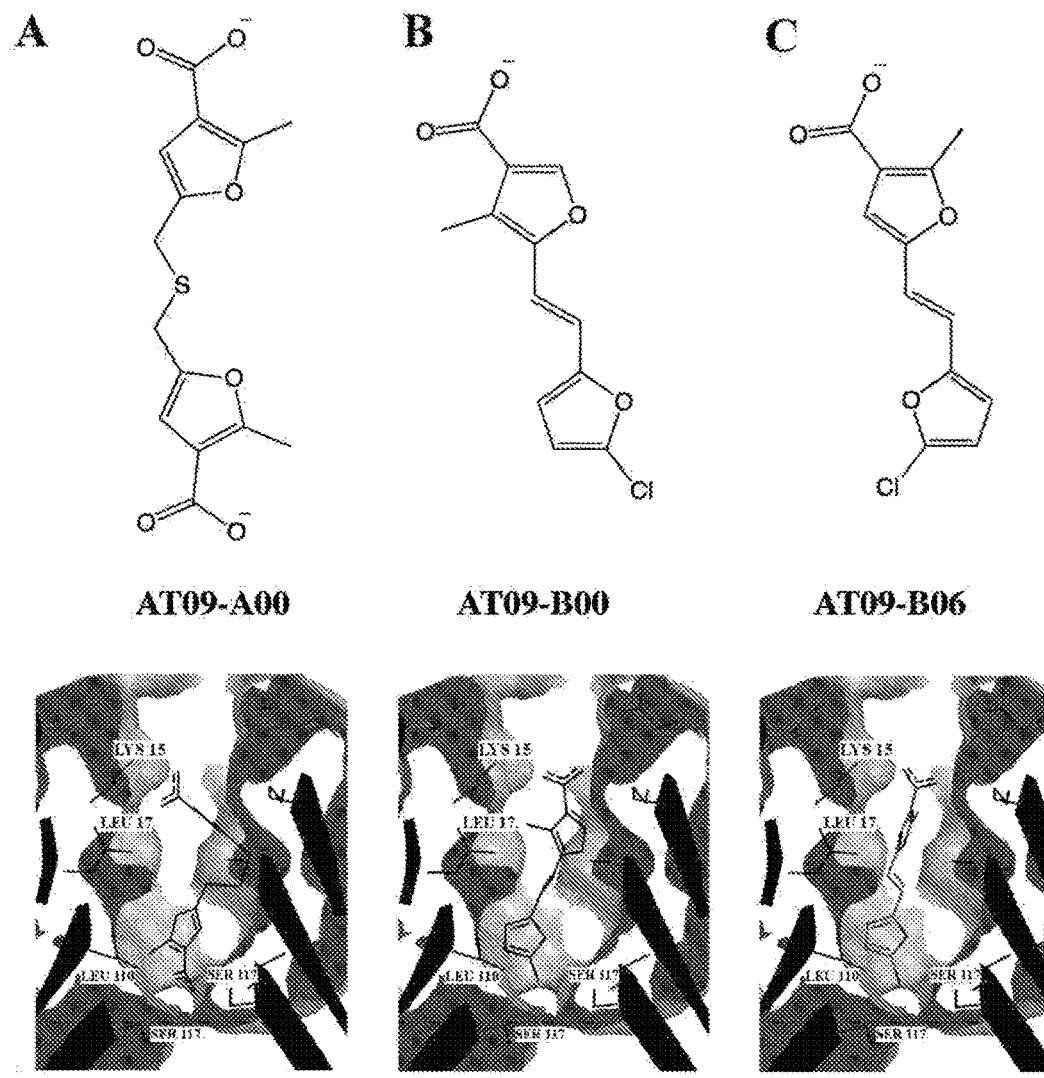
FIG. 4—Chemical formulae of AT09 compounds synthesized and tested for anti-amyloid activity: (A) AT09-A00, (B) AT09-B00 and (C) AT09-B06. The corresponding docking poses within one TTR binding site are shown in the lower row. Docking was carried out with AutoDock4 (version 4.0.1).

In an embodiment, by studying docking-predicted ligand poses of AT09-A00, in a first optimization exercise two linkers, shown in panel D of (FIG. 3), have been selected, which have been favorably reviewed in the literature [17, 34]. The two linkers are composed of two carbon atoms, share similar length (yet being one atom shorter than the AT09-A00 linker), but differ in carbon hybridization and thus in the number of rotatable bonds. The combination of these two linkers with several proposed modifications to the substituents of the furan rings, resulted in a virtual series of bis-furan derivatives that was studied in silico for their complementarity to TTR binding sites—considering both shape and electrostatics. As illustrated in FIG. 4, AT09 compounds bearing a shorter linker (FIG. 4, panels B and C) show less conformational variation within TTR binding sites, which was perceived as a favorable indication.

In an embodiment, the scaffold substitution pattern was performed. In an ideal ligand optimization scenario, one would independently test each and every modification proposed to the starting screening hit. However, given the difficulties frequently encountered during the chemical synthesis of new derivatives, this scenario is often hindered. However, computer predictions can nowadays help us trimming down the number of hypothesis to be experimentally tested, while feeding the ambition to carry out compound optimization in a resource-efficient manner.

The rationale behind the choices with regards to the substituents of the furan rings were mostly driven by the development and utilization of several predictive models of multiple molecular properties and features, including solubility, metabolic stability, pharmacokinetics, and passive permeability to the blood-brain barrier. For example, removal of one carboxyl group was justified by an attempt to maximize the probability of the resulting compounds being absorbed in the intestinal tract—which could be hindered by the presence of two negative charges found in the major microspecies of AT09-A00 at the pH values of the intestinal tract (excluding the stomach). Replacement of one methyl group for one chlorine atom not only meant to satisfy TTR's eagerness for halogens but also to increase metabolic stability. While difficulties in the chemical synthesis limited the experimental evaluation of hydroxyl-bearing AT09 derivatives, which would likely favor binding to TTR through interaction with Ser-117 residues, the predictions suggest that phase 1 metabolism may introduce that modification to the furan ring.

FIG. 4 lists the three bis-furan compounds that have been synthesized and tested for biological activity in this work. These include the screening hit AT09-A00 and two related optimized derivatives: AT09-B00 and AT09-B06.

Toxicity considerations. Despite a keen interest in conducting further studies and early optimization on the identified bis-furan hit compound, an awareness on the toxicity concerning surrounding the furan and the 3-furoic acid moieties is present. Furan is known to be a liver toxicant and hepatocarcinogen in rodents [35,36]. Injections of several furan related compounds including furosemide have been reported to produce midzonal to centrilobular necrosis in mice and rats [37,38]. Interestingly, no hepatic effects have been observed with 3-methylfuran, which is thought to be metabolised to the nontoxic carboxylic derivative [38].

Evidence of liver toxicity for furan-containing compounds in humans is limited. For example furosemide has not been associated with liver effects in humans, but it has caused jaundice and attention has been drawn to its potential hepatotoxicity in case of high dose administration to patients with renal failure [39]. Evidence of toxicity with ipomeanol, a 3-substituted furan, and with menthofuran, a monoterpene furan derivative, have also been reported in human and experimental studies respectively [40].

With such alerts in mind, in this disclosure, the toxicity potential of the bis-furan compounds now disclosed in HepG2 human liver carcinoma cell line was probed. HepG2 are widely used in the pharmaceutical industry to screen the cytotoxicity of new chemical entities at the lead generation phase [41]. These cells are highly differentiated and display many of the genotypic features of normal liver cells [42]. Details about this assay are provided below.

In an embodiment, the screening hit AT09-A00, bis((3-carboxy-2-methyl-furan-5-yl)methyl)sulfane (3), was prepared following the synthetic pathway outlined in Scheme 1. Ethyl 5-(chloromethyl)-2-methylfuran-3-carboxylate (1) was prepared through the condensation of chloroacetaldehyde and ethyl acetoacetate [43], followed by chloromethylation with paraformaldehyde and HCl, using zinc chloride as catalyst, as previously described for the chloromethylation of tri-substituted furans [44]. Then, the synthetic methodology reported by S. Wagner and co-workers for the preparation of tetrahydrothiophene [45] was applied to the synthesis of bis-furan 2. Two equivalents of chloromethylated furan 1 were reacted with $Na_2S \cdot 9H_2O$, in a mixture of dimethylformamide (DMF) and water under reflux for 2 hours, affording the bis-furan 2 in a near-quantitive yield. This bis-furan 2, upon hydrolysis of the esters groups with KOH, afforded the target bis-furan 3 in 50% yield.

In an embodiment, the synthetic methodology for the synthesis of bis-furans 9 (AT09-B00) and 12 (AT09-B06), with a trans carbon-carbon double bond as linker, is outlined in Scheme 2 and Scheme 3, respectively. The Wittig reaction between in situ generated phosphorus ylides and commercial available 5-chlorofuran-2-carbaldehyde (7) is the key step. Thus, the synthesis of the required phosphorus ylide involved the chloromethylation of ethyl 4-methylfuran-3-carboxylate (4), using the same reaction conditions as for furan 1, to give chloromethylfuran 5 in 94% yield, which then reacted with triphenylphosphine in refluxing toluene for 12 hours to afford the corresponding phosphonium salt 6 in high yield (82%). Carrying out the Wittig reaction between the phosphorus ylide, generated in situ from phosphonium salt 6 and sodium ethoxyde, and 5-chlorofuran-2-carbaldehyde (7) in refluxing ethanol for 3.5 hours led to the formation of bis-furan 8 as a mixture of E and Z stereoisomers in a 75:25 ratio. Hydrolysis of the mixture, followed by selective recrystallization (acetone/hexane), afforded the target (E)-5-[2-(5-chlorofuran-2-yl)vinyl]-4-methylfuran-3-carboxylic acid (9) in pure form (Scheme 2).

In an embodiment, in order to obtain bis-furan 12, which differs from bis-furan 9 in the position of the methyl group, phosphonium salt 10 was prepared from reaction of chloromethylfuran 1 with triphenylphosphine in refluxing toluene for 12 hours. The Wittig reaction between the corresponding phosphorus ylide and 5-chlorofuran-2-carbaldehyde (7) afforded bis-furan 11 as E and Z isomeric mixture (70:40) in 50% yield. However, successive recrystallizations (ethyl acetate/hexane) afforded the desired E-isomer of 11 in pure form (Scheme 3).

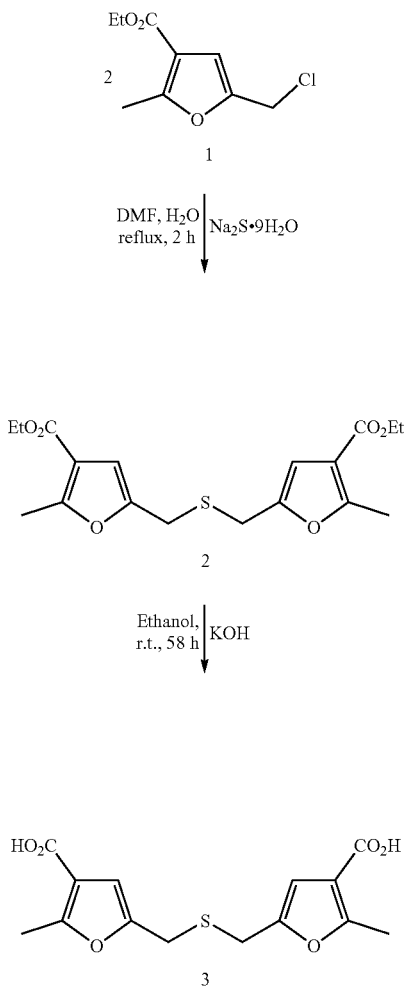

Scheme 1 - Synthetic strategy towards bis-furan 3, AT09-A00.

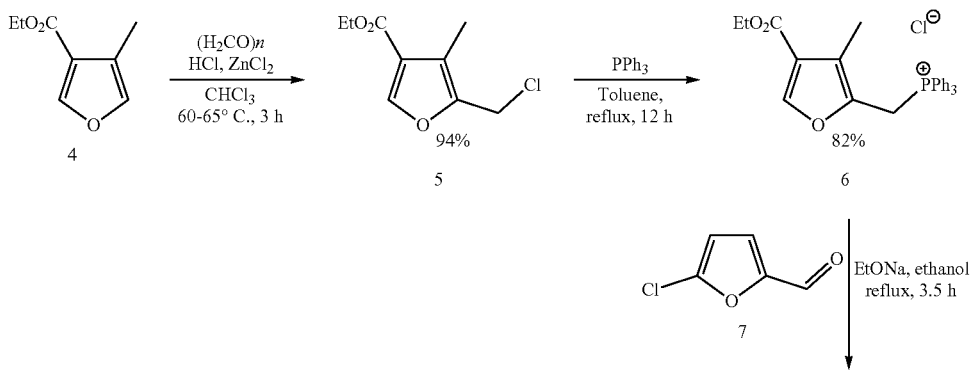

Scheme 2 - The Wittig approach to the synthesis of bis-furan 9, AT09-B06.

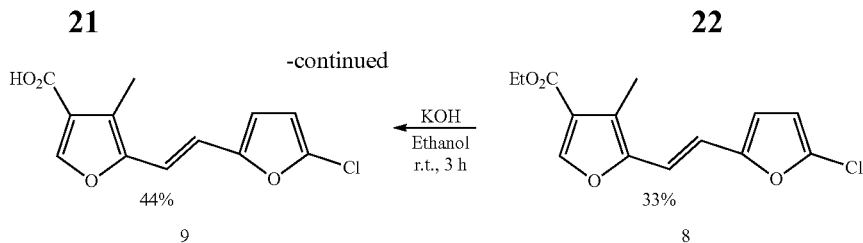

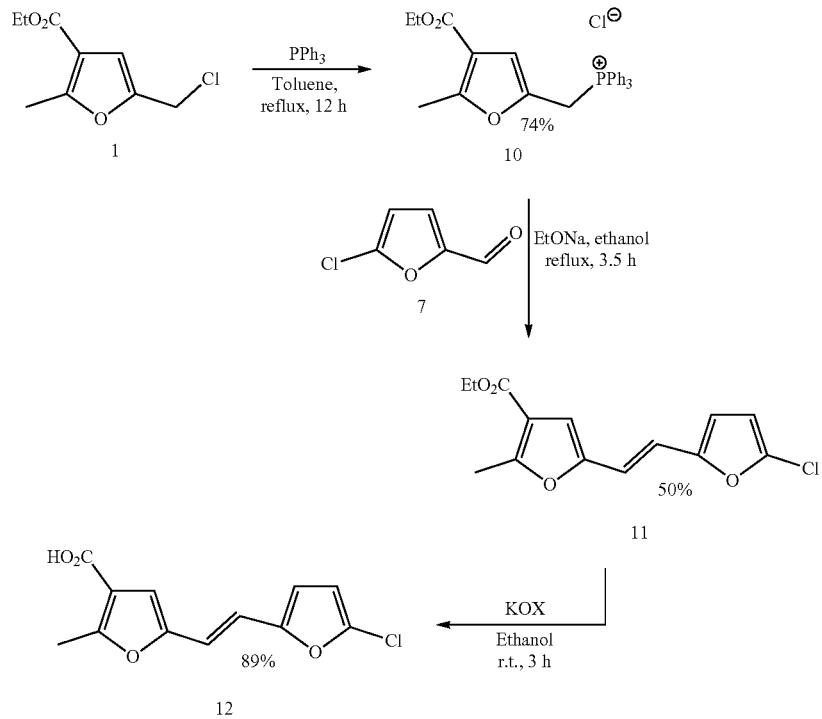

In an embodiment, the in vitro activity of the compounds now disclosed was tested. The activity of compounds towards the inhibition of amyloid fibril formation by transthyretin (TTR) may be assessed by several biochemical assays. Within the context of this work, the term "activity" (or "potency") may denote a compound's ability to bind to TTR, stabilize the native tetrameric form of the protein and prevent the formation of amyloid aggregates and fibrils. Amongst the several available assays reported in the literature to evaluate the activity of TTR stabilizers and amyloid inhibitors, a fast and reliable fibril formation assay in acidic conditions was used [32,46].

In an embodiment, the TTR aggregation assay was conducted. The first set of evaluations performed in this disclosure was based on a fast, stagnant fibril formation assay, useful in the quick screening of compounds. In this assay, a solution of the test compound is added to a solution of TTR, so that the final concentration is 3.6 µM in protein (TTR) and 7.2, 3.6 and 1.8 µM in the test compound. At such concentrations, compounds may exert their activity through binding to one or both TTR binding sites. The pH of the resulting solution is then lowered to 4.4 to promote amyloidogenesis. The process of amyloid fibril formation over time is assessed by turbidity measurements at three different wavelengths, using a spectrophotometer endowed with a microplate reader. Further details about this assay are given herein.

In an embodiment, the extent of fibril formation of each mixture was normalized by comparison to a sample with protein (TTR) in absence of test compounds, which, at the end of 72 hours, represents 100% of amyloid fibril formation. In each experiment, each compound concentration was tested in triplicate. For each compound concentration, the arithmetic mean of the triplicate experiments was calculated, as well as the arithmetic mean of the three measured wavelengths. A compound was considered "highly potent" if the resulting percentage of amyloid fibril formation was found below 10% at a compound concentration of 7.2 µM (TTR:compound stoichiometry 1:2) and below 40% at 3.6 µM (TTR:compound stoichiometry 1:1).

Figure 5:
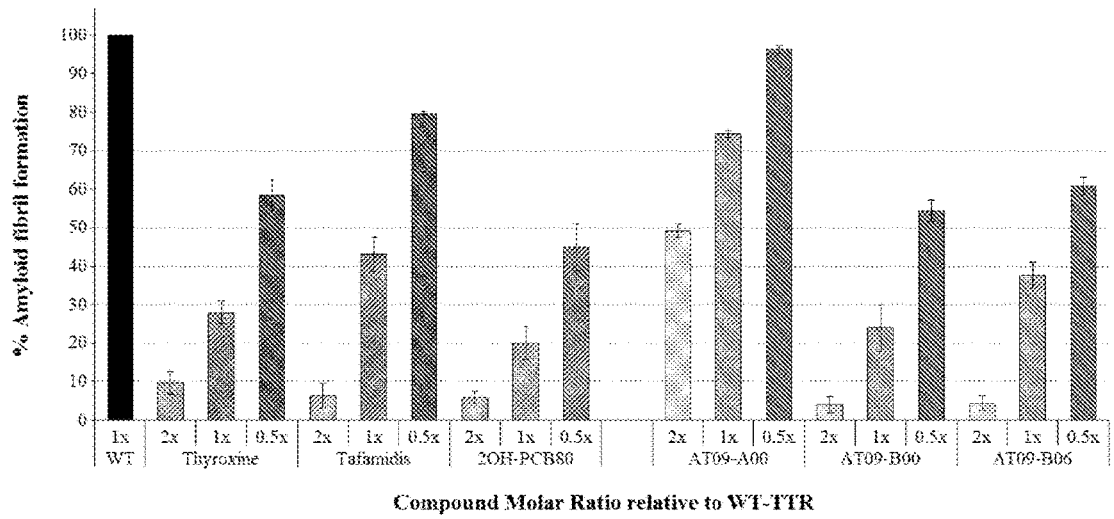
FIG. 5—In vitro evaluation of inhibitory activity against WT-TTR amyloid fibril formation of AT09 and reference compounds. Reference compounds (thyroxine, tafamidis and 2OH—PCB80) are represented by dash bars and AT09 compounds by solid-gray bars. All compounds were analyzed at 2×, 1× and 0.5× the molar concentration of wild-type TTR (3.6 µM). Upon assay completion at 72 hours incubation at 37° C., the percentage of amyloid fibril formation was normalized against the positive control (black bar) corresponding to 100% of amyloid formation in the absence of test compounds.

In an embodiment, FIG. 5 summarizes the results of the in vitro evaluation of the activity of the virtual screening hit, AT09-A00, and the two related designed derivatives, AT09-B00 and AT09-B06, towards the inhibition of amyloid fibril formation by TTR. The results are contrasted with those obtained with three reference compounds: thyroxine, the endogenous TTR ligand; tafamidis, the first and only drug treatment available for FAP; and 2OH—PCB80, a pollutant found to be one of the strongest TTR amyloid inhibitor discovered to date. While the virtual screening hit displays lower inhibitory activity than tafamidis and thyroxine, it is remarkable to verify that both AT09 derivatives produced stronger inhibition, with AT09-B00 approaching the high levels of activity of 2OH—PCB80, a highly toxic compound. These results reflect success of the early ligand optimization strategies and underlie the decision to conduct further experimental evaluation of compound AT09-B00.

Figure 6A:
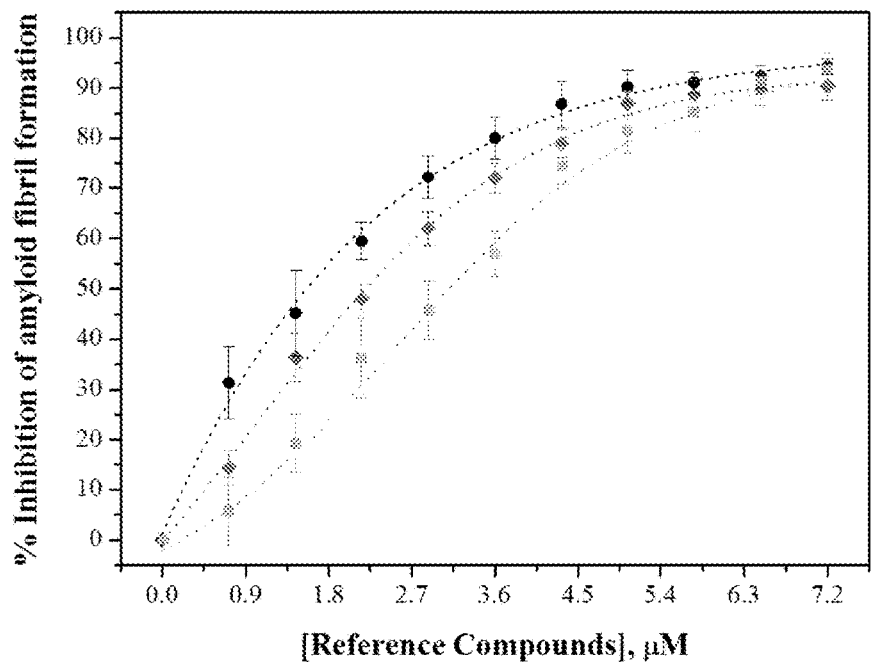
FIG. 6—Inhibition curves for reference compounds (A) and the optimized AT09 compounds (B) against wild-type TTR amyloid formation. WT-TTR was incubated with reference compounds (thyroxine, ♦; tafamidis, ■; and 2OH—PCB80, ●) and AT09 compounds (AT09-B00, ▲; and AT09-B06, ▼) at final concentrations varying between 0 and 7.2 µM, corresponding to molar ratios of 0 to 2 times the concentration of protein (3.6 µM). After 72 hours at 37° C., the percentage of amyloid fibril formation was against protein samples in absence of test compounds, corresponding to 100% of amyloid fibril formation. The inhibition curve for compound AT09-A00 is provided in FIG. 11.
Figure 6B:
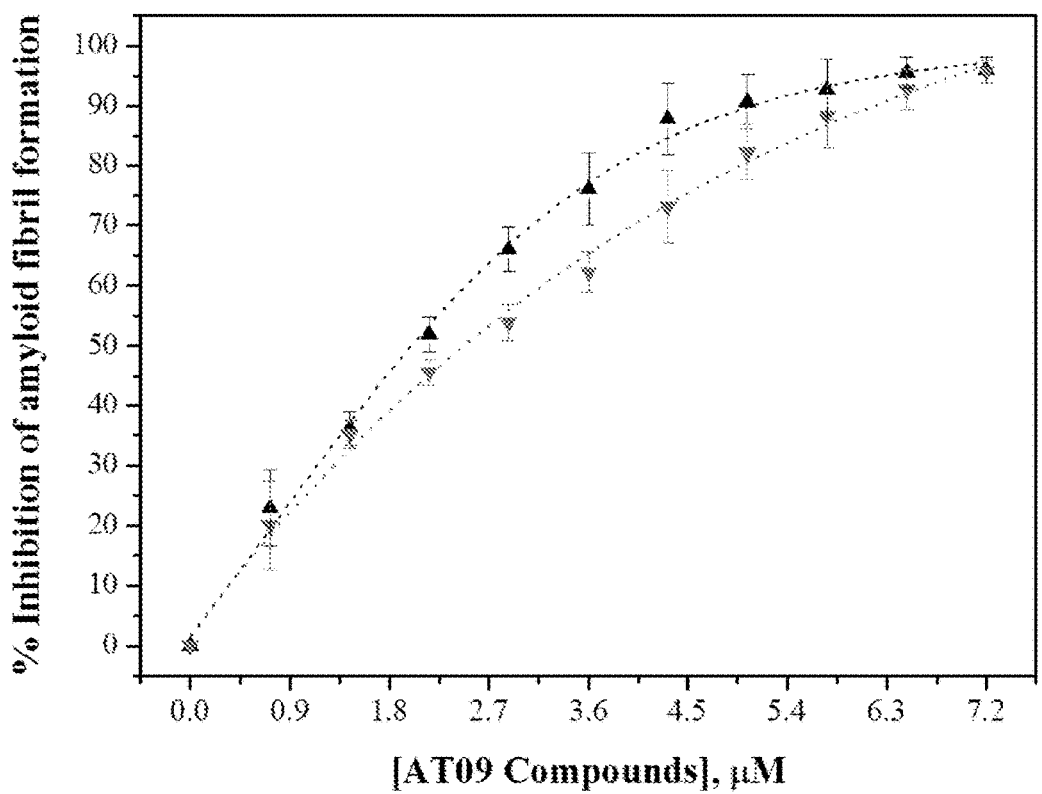

In an embodiment, the $IC_{50}$ determination assay was conducted. For the sake of disambiguation, in this disclosure, the expression "$IC_{50}$" is used to express the concentration of compound inhibiting amyloid formation by 50%, where other authors may have used the "$EC_{50}$" measure to express the same. To obtain a complementary measure of the activity of compounds, $IC_{50}$ values were determined for the screening hit, AT09-A00, the two optimized derivatives, AT09-B00 and AT09-B06, and also for the reference compounds by monitoring the effect of increasing compound concentrations on inhibition. Ten different compound concentrations were used for each $IC_{50}$ determination, while the protein concentration was kept constant at 3.6 µM (FIG. 6). The $IC_{50}$ values of the AT09 compounds are in close agreement with the results obtained on the extent of amyloid inhibition (FIG. 5). While the screening hit AT09-A00 has a higher $IC_{50}$ (7.10 µM), the two optimized derivatives AT09-B00 and AT09-B06 have lower $IC_{50}$ values than tafamidis (see Table 1). In fact, with an $IC_{50}$ of 2.02 µM, AT09-B00 surpasses all reference compounds, except 2OH—PCB80, in terms of amyloid inhibition activity in vitro. As suggested by Johnson et al., the ability to reach such high levels of inhibition when working with protein concentrations (3.6 µM) that mimic TTR concentration in serum is only possible if compounds effectively stabilize the protein by occupying only one of TTR's two equivalent T4-binding sites [6]. Although positive cooperativity in ligand binding to the two TTR binding sites has been proposed as a critical aspect of 2OH—PCB:TTR interactions with implications in amyloid formation [32], the results seem to lessen the importance of binding cooperativity in achieving an efficient inhibition. It may be argued that the high inhibition profile witnessed for 2OH—PCB ($IC_{50}$ of 1.59 µM) is mostly linked with its near-perfect shape and chemical complementary for T4 biding sites, leading to its high affinity [32].

In an embodiment, Isothermal titration calorimetry (ITC) experiments were conducted to determine the binding constants of bis-furan compounds to TTR. Tafamidis was also studied in order to allow the benchmarking of AT09-B00 and AT09-B06 against a reference TTR stabilizer. In all experiments, a solution of the test compound (at a concentration of 130 µM for the bis-furans and 150 µM for tafamidis) was titrated into a calorimetric cell containing WT-TTR (7 µM) at 25° C. An initial injection of 4 µL of titrant was followed by 28 regular injections of 10 µL until saturation of the titrated solution was reached. The heat associated with each injection was measured throughout time and calculated by integration of the area under the deflection of the measured peak, after baseline correction (i.e. subtraction of blank). Further details about the ITC experiments are provided herein.

Figure 7A:
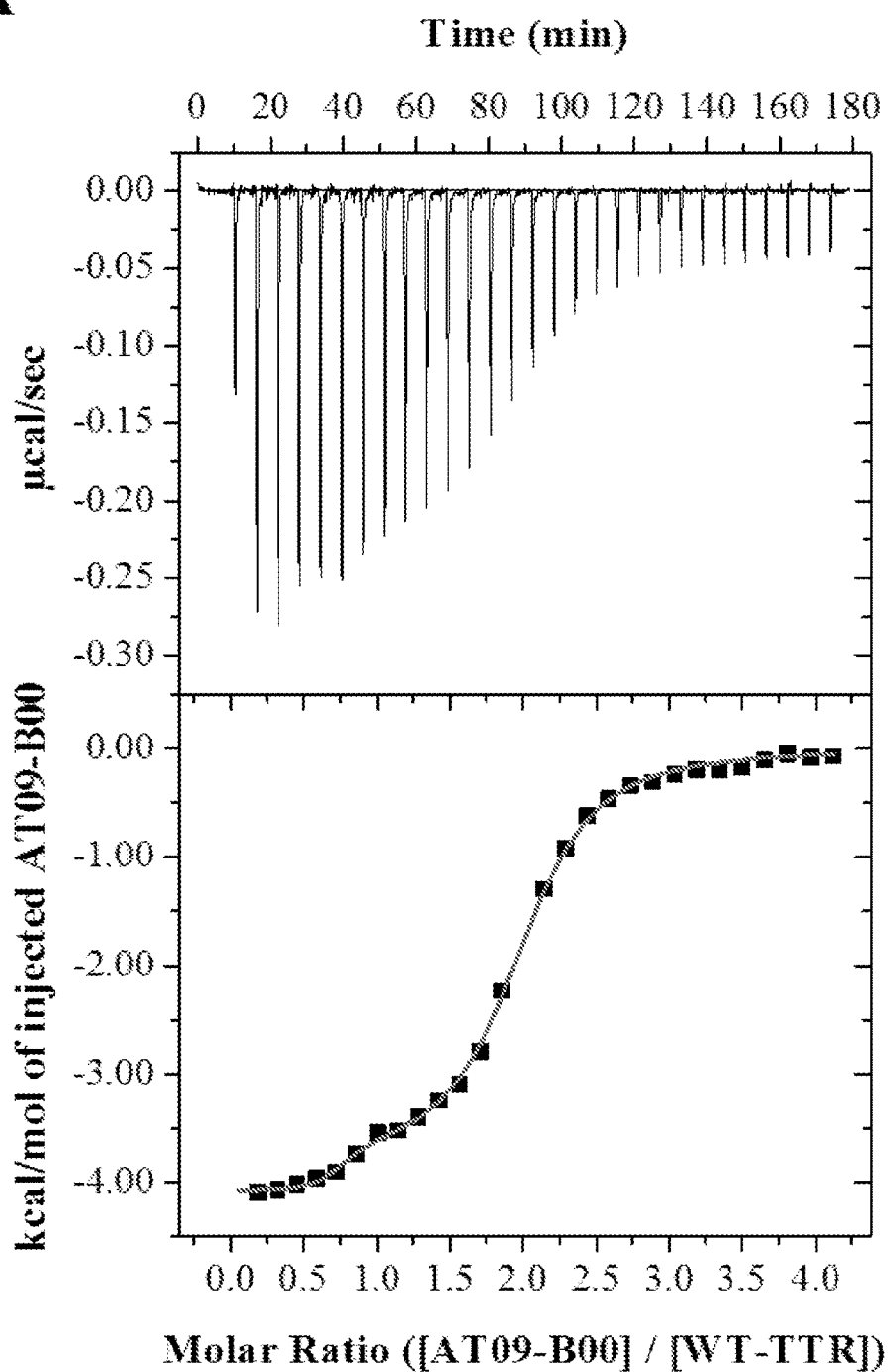
FIG. 7—calorimetric titration of AT09-B00 (A), AT09-B06 (B) and tafamidis (C) with WT-TTR. ITC experiments were performed in 20 mM sodium phosphate, 150 mM sodium chloride, pH 7.2, 2% DMSO, and at 25° C. Top panels show the recorded heat changes associated with the injection of ligand into the reaction cell containing protein solution. Bottom panels show the binding isotherm corresponding to the data in the top panels and the best fitting curves. The heat of dilution of each ligand solution was subtracted from the raw data. Association constants were obtained through non-linear regression (solid line) of the experimental data, according to a model of binding to a macromolecule with two ligand-binding sites, using the ITC data analysis module in Origin version 7.0 provided by Malvern.
Figure 7B:
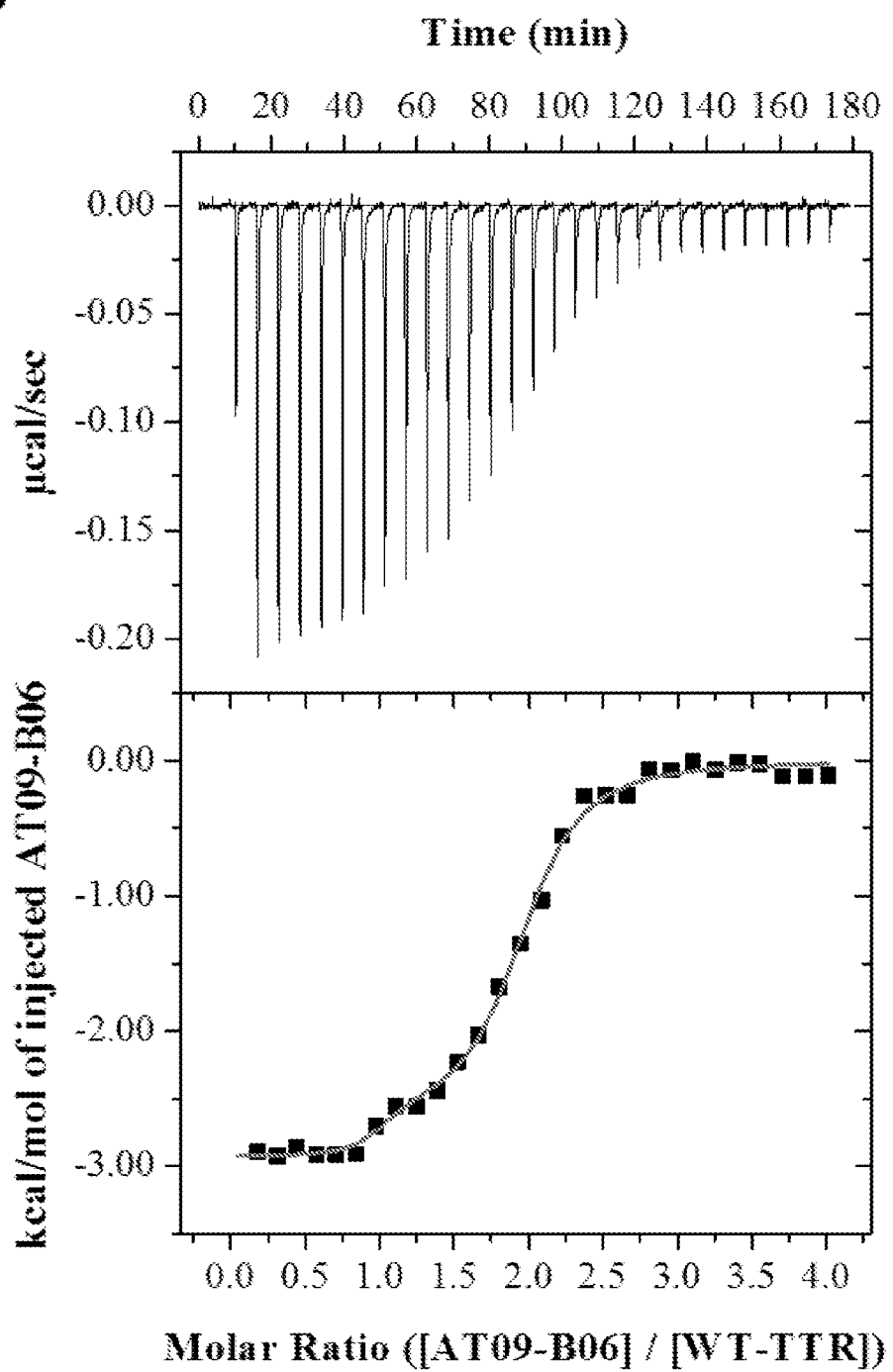
Figure 7C:
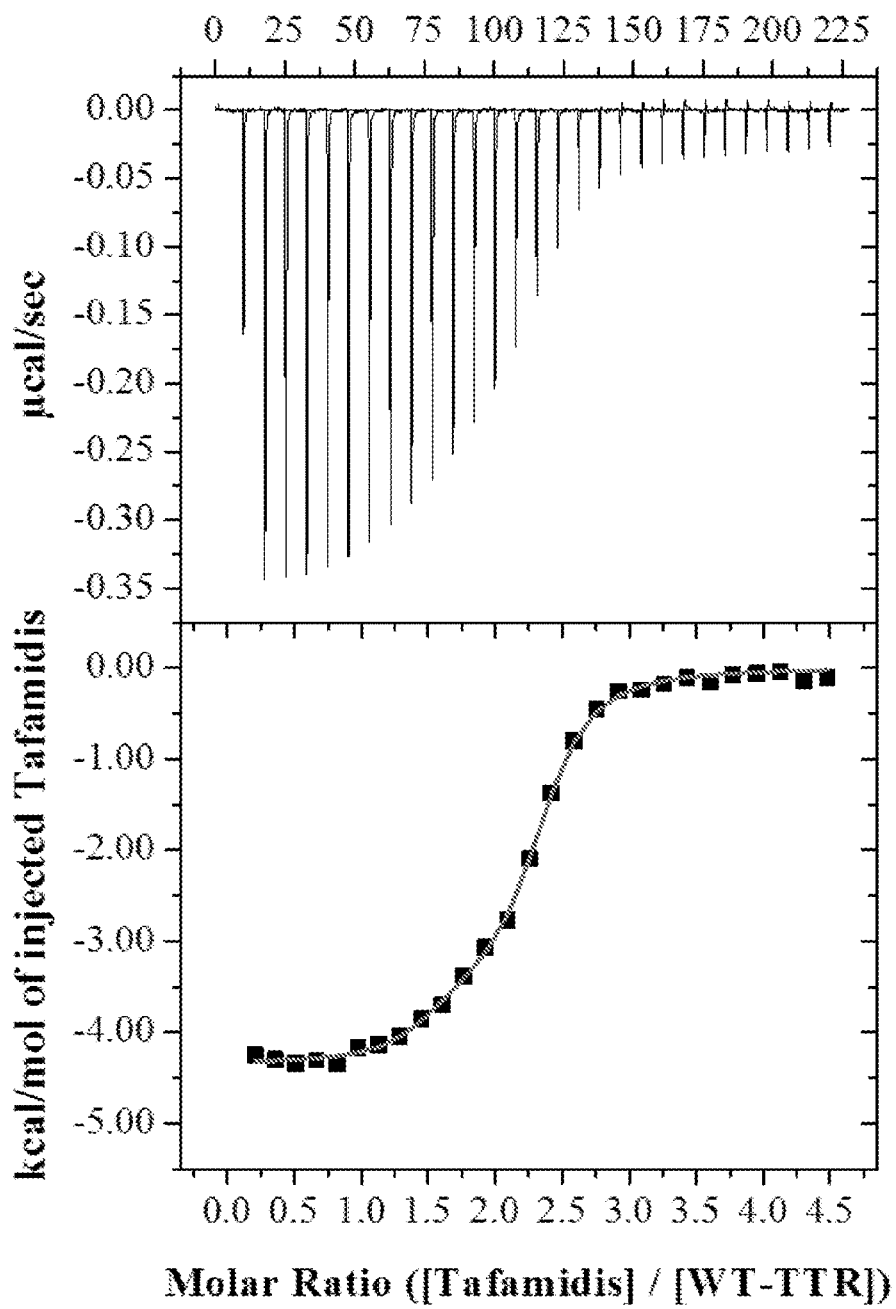

As shown in FIG. 7, the integrated heat exchanges were plotted against the molar ratio of the added compound to WT-TTR, resulting in complete binding isotherms. The isotherms were best fit by a model of binding to a macromolecule with two ligand-binding sites [47], and the association constants were obtained via non-linear regression (FIG. 7, bottom panels). The corresponding dissociation constants were calculated according to the equation given herein. The results indicate that both bis-furan compounds bind TTR with negative cooperativity: $K_{d1}$=3.5 nM and $K_2$=357 nM for AT09-B00; $K_{d1}$=3.9 nM and $K_{d2}$=278 nM for AT09-B06. These dissociation constants may seem only marginally better than the ones obtained for tafamidis ($K_{d1}$=9.3 nM and $K_2$=274 nM)—and similar to those recently reported for the inhibitor AG10 ($K_{d1}$=4.8 nM and $K_{d2}$=314 nM) [48]. However, the differences in $K_{d1}$ (AT09-B00<AT09-B06<tafamidis) seem to agree with the level of inhibitory activity reflected by the determined $IC_{50}$ values: respectively, 2.02 µM, 2.49 µM and 3.10 µM for AT09-B00, AT09-B06 and tafamidis (see Table 1). These results substantiate the above stated notion that the first ligand binding event, and in particular the affinity of that first association, may be the main driver of TTR stabilization and consequent inhibition of amyloid formation. Indeed, regardless of the difference between $K_{d1}$ and $K_{d2}$ (i.e. the extent of cooperativity in binding to the two equivalent T4-binding sites), a lower $K_{d1}$ tends to yield higher inhibitory activity.

A more exhaustive analysis of the thermodynamic signature behind the association of bis-furan compounds to WT-TTR and other amyloidogenic variants is underway, and will be provided in a separate contribution. Hopefully, this will indulge the curiosity on the role of the enthalpic and entropic components to achieving tight binding to and stabilization of particularly unstable TTR variants. Nevertheless, the results presented herein provide insight on a key determinant for the inhibition of TTR amyloid formation and underline the value of the bis-furan compounds now disclosed as potent TTR stabilizers.

Efficiency and lipophilic efficiency in amyloid inhibition: "ligand efficiency" and "ligand lipophilic efficiency" are two renowned metrics widely used in the drug discovery field, particularly in lead selection and optimization [49]. These metrics attempt to provide a measure of compound quality by capturing the ratio between potency and, respectively, the number of non-hydrogen atoms or lipophilicity of an active molecule. This notion of efficiency is relevant given the high number of failures of large and highly lipophilic candidates in the recent past, mostly linked to toxicity problems. Abad-Zapatero and Metz proposed an additional metric, based on the ligand efficiency metric, called "binding efficiency index" (BEI), suggesting that molecular weight deals better with the contribution of heteroatoms from different rows of the periodic table [50].

Since several ligands that compete with T4 for T4-binding TTR sites are "greasy" halogenated biaryl compounds, it seemed relevant to quantify the efficiency of the TTR amyloid inhibitors under study on such basis. The reference value of 27 for BEI was determined using a reference $IC_{50}$ value of 1.0 nM [50]. Because the $IC_{50}$ values express the concentration of compound inhibiting TTR amyloid fibril formation by 50% and reflect the high protein concentrations used in the in vitro assay (thus departing from the typical values obtained for common measures of activity, affinity or potency), a correction factor of 1000 is applied to bring values within a similar scale, and call this new metric "inhibition efficiency index" (1E1). Moreover, an "inhibition ligand efficiency" (ILE), for the compounds now disclosed, is calculated by subtraction of the calculated octanol-water partition coefficient (c Log P) to the $pIC_{50}$ values, which in fact reflects the ratio between inhibition efficiency ($IC_{50}$) and the octanol-water partition coefficient.

Figure 8:
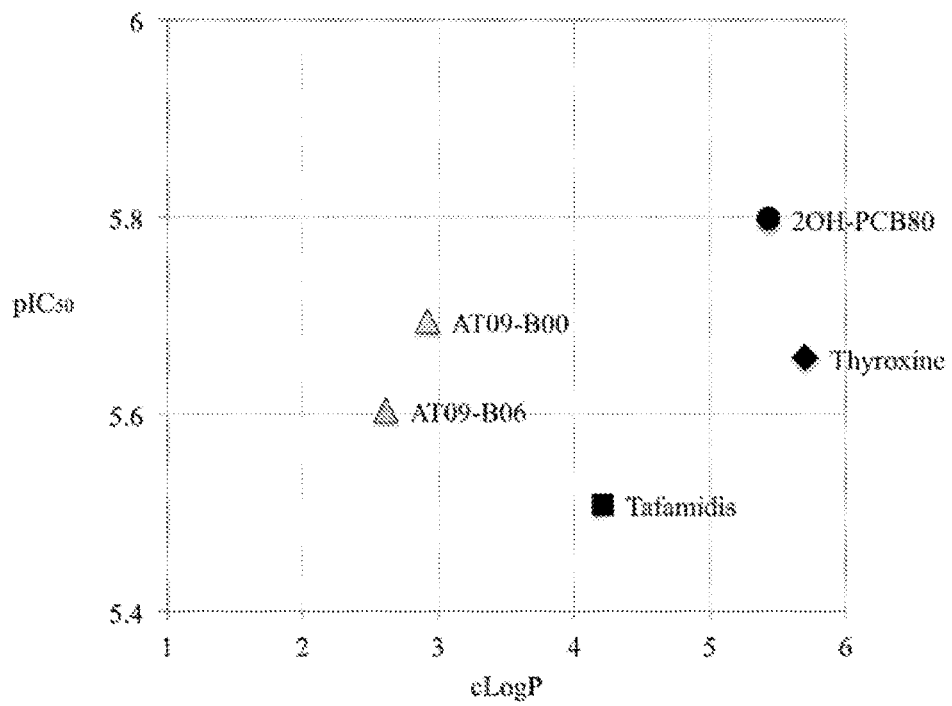
FIG. 8—Lipophilic efficiency at TTR amyloid inhibition (LiPE-like plot) for AT09 and reference compounds, depicting the relationship between inhibitory activity ($pIC_{50}$) and lipophilicity (c Log P).
Figure 9A:
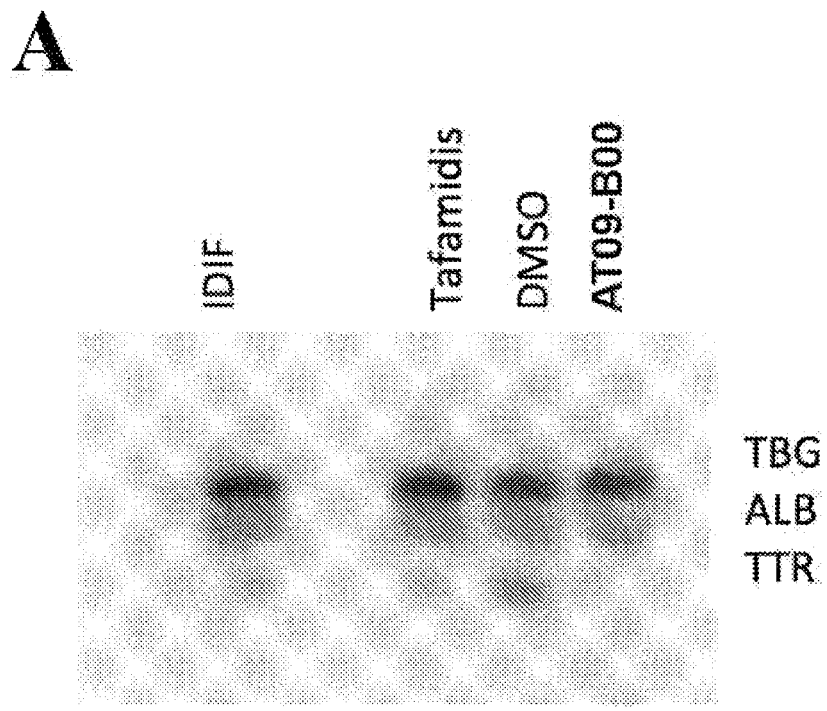
FIG. 9—TTR T4-binding competition assays (A, B) and TTR stability to dissociation assays (C, D) for AT09-B00 and reference compounds, in human plasmas from normal subjects (wild-type TTR) and heterozygotic TTR V30M carriers. Iododiflunisal (IDIF) and tafamidis (taf.) are included for comparison, incubated in equal amount as AT09-B00. (A) PAGE analysis of heterozygotic TTR V30M carrier plasma incubated with $[^{125}I]$-T4, in the absence (DMSO) or presence of the test or reference compounds. The bands correspond to radioactive T4 bound to the major T4-binding plasma proteins: thyroxine-binding globulin (TBG), albumin (ALB) and transthyretin (TTR). (B) The results shown in A for TTR are analyzed by calculation of the TTR/total (TTR+ALB+TBG) ratio for each sample. (C) IEF analysis of plasma TTR stability to dissociation in the absence (vehicle) or presence of the test compound (AT09-B00) or reference compounds. The different molecular species visualized in an exemplary IEF gel after Coomassie Blue staining are indicated. (D) Bar charts showing the ratio between the bands for TTR tetramer and total TTR, obtained after densitometry of IEF gels corresponding to 5 plasma samples of normal and TTR V30M carriers.
Figure 9B:
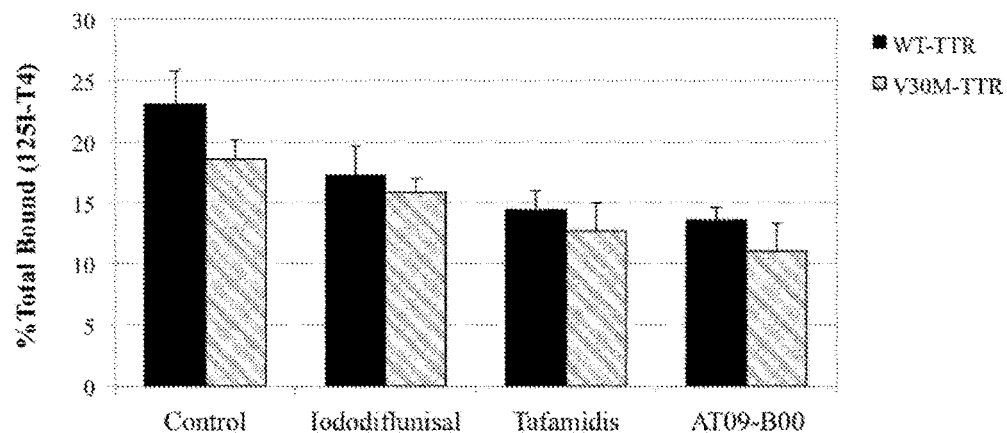
Figure 9C:
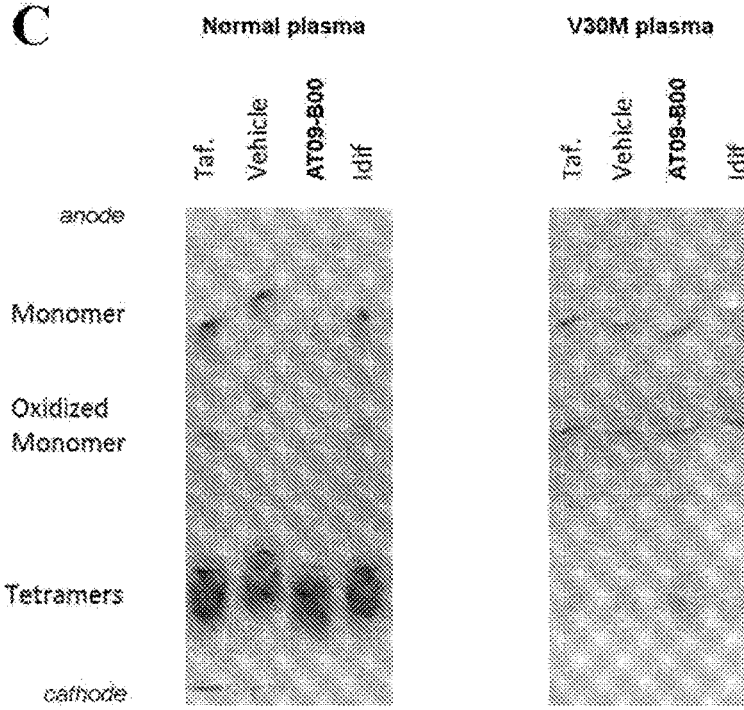
Figure 9D:
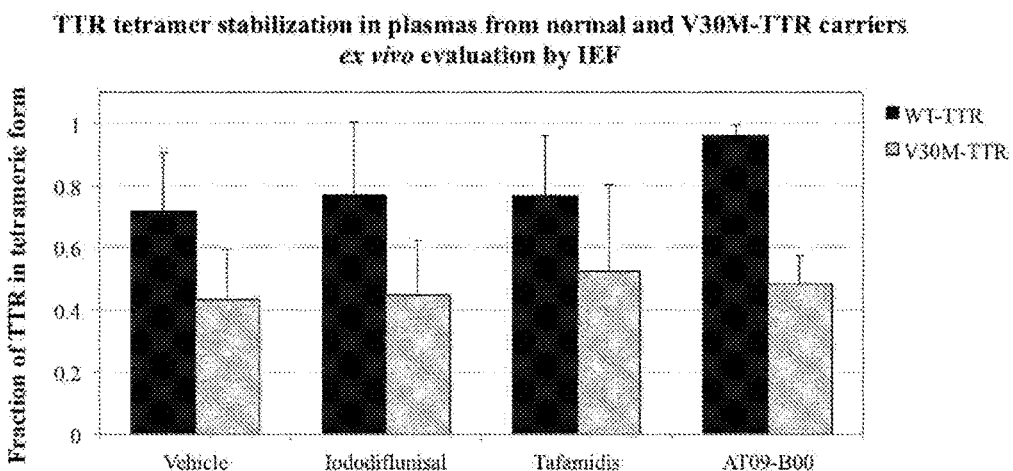

Table 1 reports the $IC_{50}$ values determined for AT09 and reference compounds, along with basic physicochemical properties and the inhibitory efficiency metrics herein defined. The results show that, besides more active than the reference compounds, except 2OH—PCB80, AT09 compounds hold the highest inhibition efficiency and inhibition lipophilic efficiency compared to all reference compounds. In addition, FIG. 8 provides a complementary graphical representation of the lipophilic efficiency of AT09 compounds as compared to the reference compounds.

TABLE 1

Basic physicochemical properties, $IC_{50}$ values and inhibition efficiency metrics for AT09 compounds, compared with reference compounds.

| Compound | MW (Da) | $IC_{50}$ ± S.D. (μM) | $pIC_{50}$ | cLogP | IEI* | ILE** |
| --- | --- | --- | --- | --- | --- | --- |
| AT09-B00 | 252 | 2.02 ± 0.22 | 5.69 | 2.92 | 22.6 | 2.77 |
| AT09-B06 | 252 | 2.49 ± 0.30 | 5.60 | 2.61 | 22.3 | 2.99 |
| Tafamidis | 307 | 3.10 ± 0.15 | 5.51 | 4.21 | 17.9 | 1.30 |
| 2OH-PCB80 | 322 | 1.59 ± 0.27 | 5.80 | 5.43 | 18.0 | 0.37 |
| T4 | 763 | 2.20 ± 0.03 | 5.66 | 5.70 | 7.4 | −0.04 |

$IC_{50}$ values, corresponding to the concentration of test compounds capable of inhibiting TTR amyloid fibril formation by 50%, were determined from the inhibition curves shown in FIG. 6 and as described in the herein.
Values are reported as the mean of at least 3 independent determinations ± the standard deviation. $pIC_{50}$ values correspond to the negative logarithm of $IC_{50}$ values.
*IEI is the acronym for "inhibition efficiency index", which is defined here as: IEI = $(pIC_{50}/MW) \times 1000$.
**ILE is the acronym for "inhibition lipophilic efficiency", which is determined by the formula: ILE = $pIC_{50}$ − cLogP.
The cLogP was calculated at the same model pH for all compounds, on the basis that all compounds (except 2OH-PCB80) bear one carboxylic acid functionality.

In an embodiment, ex vivo evaluation were conducted, in particular another set of experiments, involving assays of higher complexity, was performed in order to confirm the affinity of the compounds for TTR, their stabilizing effect on the protein, and also their selectivity for TTR versus other T4-binding proteins found in the blood plasma. These assays have been applied only to the most potent AT09 TTR amyloid inhibitor identified in vitro, AT09-B00, using two reference compounds for comparison purposes: iododiflunisal (IDIF), a TTR stabilizer reported previously [51], and tafamidis, the only drug for FAP approved by the European and the Japanese regulatory agencies (see FIG. 1).

In an embodiment, thyroxine competition in human plasma was evaluated. In particular, binding affinity and selectivity for plasma TTR was assessed by competition with thyroxine (T4) for TTR and plasma proteins albumin (ALB) and thyroxine-binding globulin (TBG), taking advantage of radioactive-labeled thyroxine ($[^{125}I]$-T4) in a displacement assay monitored by native polyacrylamide gel electrophoresis (PAGE), described in detail in the present disclosure. AT09-B00 was assayed in order to confirm its putative mode of action through binding to TTR's T4 binding sites and obtain a preliminary assessment of the compound's selectivity for TTR versus other carrier proteins present in the plasma.

The results of the competition assays in Panels A and B of FIG. 9 allow an estimate of two important aspects: compound affinity for TTR T4-binding sites and compound specificity amongst the plasma T4-carrier proteins. In these experiments, heavy bands in the gel indicate high amounts of radioactive T4 bound to different plasma proteins. Thus, a decrease of band intensity indicates displacement of radioactive T4 from the corresponding plasma protein. From analysis of Panel A (FIG. 9) it is clear that most T4 is bound to TBG, followed by albumin and TTR (lane "DMSO"). Moreover, incubation of plasma with the test and reference compounds leads to a significant decrease in the amount of T4 bound to TTR. This is obvious for iododiflunisal (lane "IDIF"), more so for tafamidis (lane "taf."), but even more so for AT09-B00. Thus, displacement of T4 from TTR, and consequently binding affinity for TTR, occurs in the following increasing order: iododiflunisal<tafamidis<AT09-B00. This is confirmed by the quantification shown in Panel B (FIG. 9). Here, the results are reported as ratios between band intensity associated to T4 binding to TTR and T4 binding to the total plasma proteins (TBG+ALB+TTR) and the amount of radioactive T4 bound to TTR is lowest in the sample incubated with compound AT09-B00. The specificity of AT09-B00 for TTR is also highlighted by the small difference in band intensity for TBG and albumin in contrast with the large decrease observed for the TTR band (Panel A, FIG. 8).

Additionally, Panel B of FIG. 9 also highlights the comparison of T4 displacement in plasmas from both normal and TTR V30M carriers. While it could be argued that compound AT09-B00 shows superior T4 competition for TTR V30M when compared to tafamidis, the fact that this compound offered results at least comparable to the current drug, prior to substantial lead optimization efforts, is a positive indication on the potential relevance of the bis-furan scaffold towards the development of novel and highly effective TTR stabilizers.

Full bar charts showing T4 displacement from other T4-carrier proteins in plasmas (including TBG, ALB and TTR) are provided in supplementary data.

In an embodiment, TTR tetramer stabilization in human plasma was evaluated. Therefore, besides their affinity for TTR binding sites in plasma or their ability to prevent amyloid formation in vitro, the ultimate challenge for compounds under test, with regards to their potential therapeutic activity, consists in the assessment of their ability to stabilize the mutant protein upon binding.

In an embodiment, the AT09-B00 compound was further tested ex vivo for its effect on the stability of human plasma TTR, using isoelectric focusing (IEF) under semi-denaturating conditions, i.e. in the presence of 4 M of urea—as described in this disclosure and in references [51,52]. After plasma incubation with the test and reference compounds, TTR was isolated by PAGE and run on IEF. Bands corresponding to different TTR species were quantified and the tetramer to total protein ratio was determined. Under the experimental conditions used, TTR presented a typical pattern of two main bands, representing monomers (normal and oxidized forms), and several bands of lower isoelectric point (pI) indicating different forms of TTR tetramers.

In panel C of FIG. 9, an exemplary IEF gel is shown. As compared to vehicle and the reference TTR stabilizer iododiflunisal, in the presence of AT09-B00 and tafamidis stronger bands corresponding to TTR tetramers are observed and the bands corresponding to monomeric species were reduced or absent. The bar chart (panel D) shows the result of IEF densitometric analysis of isolated TTR incubated with the compounds, expressed as the tetramer to total protein ratio. The plotted values correspond to averages taken across repeated experiments with 5 samples obtained from wild type TTR plasmas and 5 samples from Val30Met TTR (TTR V30M) plasmas. Strikingly, samples incubated with AT09-B00 yielded a tetramer to total protein ratio of 0.961 (S.D.=0.034; P-value<0.05), compared to 0.717 in the control (vehicle), 0.768 with iododiflunisal and 0.767 with tafamidis—an impressive result in wild type TTR.

Perhaps more strikingly, the stability of TTR V30M seemed to be only marginally affected by the presence of compounds in the IEF studies under semi-denaturing conditions. As can be witnessed in panels C and D (FIG. 9), all tested compounds showed limited ability to stabilize TTR in plasmas of heterozygotic V30M carriers, with AT09-B00 yielding a tetramer to total protein ratio of 0.481

(S.D.=0.094; P-value=0.80), compared to 0.430 in the control (vehicle), 0.445 with iododiflunisal and 0.522 with tafamidis. While these results may disclose a poor TTR stabilization performance for the small organic compounds under test, including AT09-B00, they underline a critical need for the discovery of compounds endowed with chaperone-like activity against multiple variants of TTR. Given that more than 100 mutations in the TTR sequence are linked to reduced protein stability and amyloidogenesis, this is a highly desirable goal.

In an embodiment, the toxicity profiling in HepG2 cell lines was evaluated. Cell viability of HepG2 cells (human liver carcinoma cell line) was determined in the presence of increasing concentrations of AT09-B00 and AT09-B06, in order to obtain a preliminary assessment of the toxicity of the bis-furan compounds (a detailed description of the assay may be found below). Further toxicology is required if AT09 compounds are to be progressed to subsequent stages of development, not only to discard potential liver damage (or toxicity to other organs/tissues) but also given the long-term nature of treatments required by patients suffering from TTR amyloidoses (such as FAP), associated co-morbidities, or other TTR-related pathologies.

Figure 10:
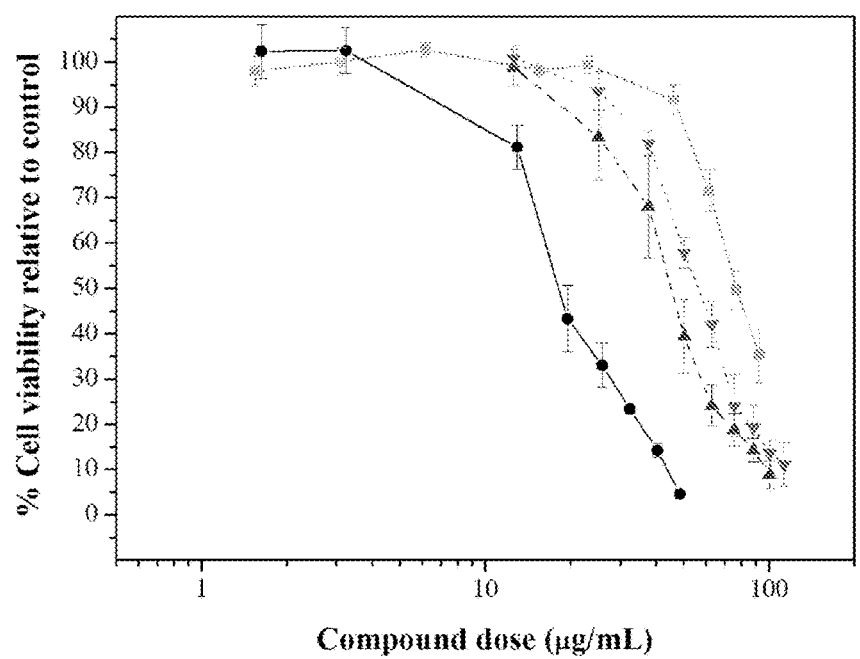
FIG. 10—Cell (HepG2) viability in the presence of reference and AT09 compounds. HepG2 cells were treated with tafamidis (■, solid line), 2OH—PCB80 (●, solid line), AT09-B00 (▲, dash line) and AT09-B06 (▼, dot line) for 72 hours. Cell viability was determined by the resazurin assay and the percentage of viable cells was normalized against a positive control with no compound added, corresponding to 100% cell viability.
Figure 11:
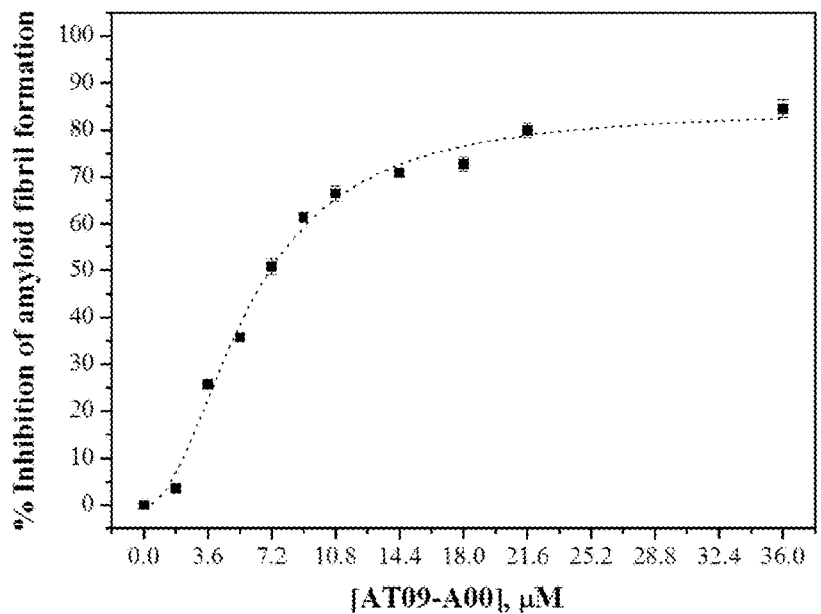
FIG. 11—Inhibition curve of the screening hit AT09-A00 against wild-type TTR amyloid formation.
Figure 12:
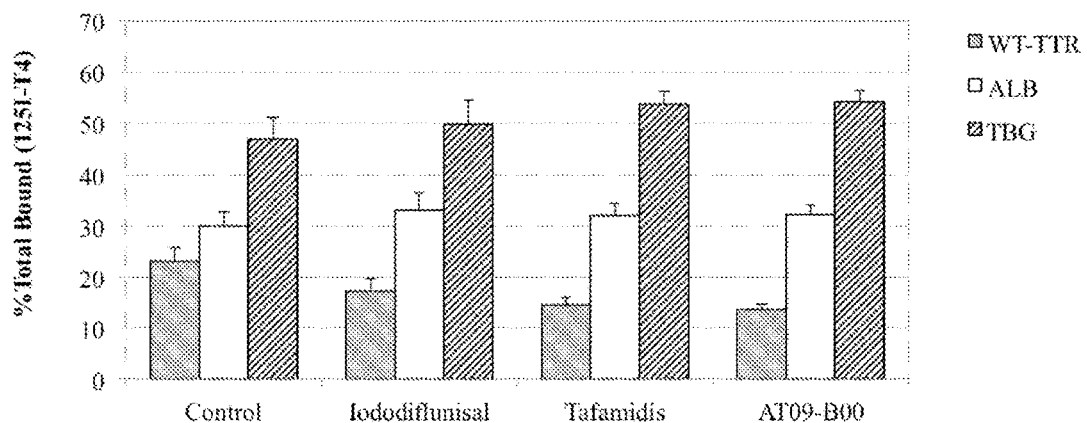
FIG. 12—T4-binding competition assays for AT09-B00 and reference compounds, in human plasmas from normal subjects (wild-type TTR). Iododiflunisal (IDIF) and tafamidis (taf.) are included for comparison, incubated in equal amount as AT09-B00. The compounds displace radioactive T4 from the three main T4-carrier proteins in the blood plasma by competition.
Figure 13:
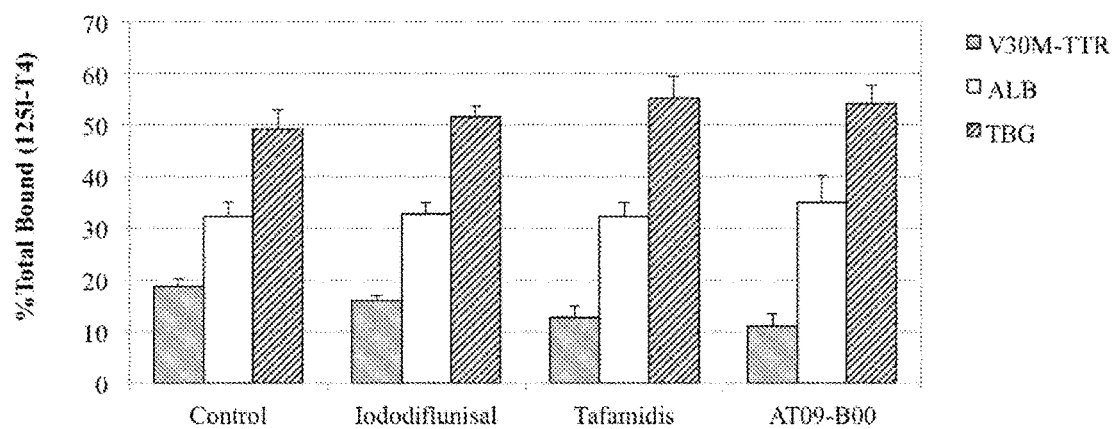
FIG. 13—T4-binding competition assays for AT09-B00 and reference compounds, in human plasmas from heterozygotic TTR V30M carriers.

FIG. 10 shows the results of cell viability studies conducted with compounds AT09-B00 and AT09-B06. The plot shows that these compounds have relatively low toxicity for HepG2 cells, even at high doses, showing viability profiles comparable to that of tafamidis. Tafamidis appears to be a well tolerated and safe compound, as suggested by the results of an open clinical study [9]. Indeed, an inhibitory dose at 50% of the dose-response curve ($ID_{50}$) of more than 75 µg/mL was obtained with tafamidis. Compounds AT09-B06 reached an $ID_{50}$ value of 56.6 µg/mL, while the most active amyloid inhibitor AT09-B00 exhibited an $ID_{50}$ of 45.5 µg/mL. A summary of these results can be found in Table 2.

TABLE 2

$ID_{50}$ values determined from cell viability assays in HepG2 cell lines upon 72 hours of incubation with test and reference compounds. Values are provided both in µg/mL (dose) and µM (concentration).

| Compound | $ID_{50}$ | |
| --- | --- | --- |
| | µg/mL | µM |
| AT09-B00 | 45.5 | 181 |
| AT09-B06 | 56.6 | 225 |
| Tafamidis | 76.1 | 247 |
| 2OH-PCB80 | 19.4 | 60 |

The quest for efficacious therapies for amyloid neurodegenerative diseases is at the heart of a global effort among academic groups, biotech companies and the pharmaceutical industry. In the present report, the discovery of novel and potent transthyretin amyloid inhibitors is disclosed. Departing from the common halogenated biaryl pharmacophore of TTR ligands and following the identification of a bis-furan scaffold through in silico approaches, this disclosure presents the rationale behind early ligand optimization of compounds with high inhibitory activity and efficiency. This included the replacement of a —$CH_2SCH_2$-linker, holding high flexibility and associated heavy conformational entropy penalty, for a shorter and more rigid trans-olefin linker found in stilbenoid amyloid inhibitors. Together with a conservative new set of substituents to the furan rings, this modification yielded two derivatives displaying lower $IC_{50}$ values than tafamidis, the only presently available drug solution for TTR amyloidosis, in spite of their lower molecular weight and lipophilicity. Besides inhibiting TTR amyloid in vitro more efficiently, the reported compounds showed high thyroxine displacement and selectivity for TTR in blood plasmas from normal subjects and TTR V30M carriers. The best bis-furan compound showed unprecedented ability to stabilize the native tetrameric form of wild-type TTR in human plasma.

The mode of action of the reported bis-furan compounds, along with the opportunity to fine-tune molecular properties of new potential candidates for different target-product profiles at the current stage of research, underlines the relevance of this discovery towards the treatment of TTR-related clinical manifestations in the central nervous system and also to the field of Alzheimer's disease—where TTR may play a neuroprotective role.

In an embodiment, reference compound 2OH—PCB80 was purchased from ChemBridge Corporation (San Diego, Calif.). Thyroxine, DMSO and other chemicals required for synthesis and biochemical evaluation were purchased from Sigma-Aldrich Co. with the highest purity commercially available. During the screening stage (prior to the elucidation of its synthetic route), the hit compound AT09-A00 was acquired from TimTec LLC, Newark Del. 19711, USA, under catalog code ST092803 (ST4010891 in March 2011), in the amount of 10 milligrams. Iododiflunisal was available in Saraiva's research lab at Instituto de Biologic Molecular e Celular, Universidade do Porto. Tafamidis was prepared using general procedures described in the literature [53].

In an embodiment, all compounds used in this work, namely compound 9, compound 12 and tafamidis, were recrystallized after synthesis, their melting point was determined and their structure confirmed by NMR. The purity of the compounds was further assessed by High-Resolution Mass Spectrometry (HRMS) and Gas Chromatography Mass Spectrometry (GCMS), revealing near complete purity of all test items.

In an embodiment, NMR spectra were run in $CDCl_3$ or DMSO-$d_6$ on a 400 MHz instrument and recorded at the following frequencies: proton ($^1H$, 400 MHz), carbon ($^{13}C$, 100 MHz), phosphorus ($^{31}P$, 161.97 MHz). Chemical shifts are expressed in parts per million related to internal TMS, and coupling constants (J) are in hertz. Infrared spectra (IR) were recorded on a Fourier Transform spectrometer. Mass spectra were recorded under electrospray ionization (ESI) and electronic impact (EI). Melting points were determined in open glass capillaries and are uncorrected. Thin-layer chromatography (TLC) analyses were performed using precoated silica gel plates. Flash column chromatography was performed with silica gel 60 as the stationary phase. Furans 1 and 4 were prepared using general procedures described in the literature [54-56].

In an embodiment, the synthesis of Bis((3-carboxy-2-methyl-furan-5-yl)methyl)sulfane (3) (AT-09-A00) was carried out as follows: Bis ((3-ethoxycarbonyl-2-methyl-furan-5-yl)methyl)sulfane (2): A round-botted three-necked flask with dimethylformamide (6.0 mL) was heated at 175° C. After suspending the heating, furan 1 (1.95 g, 2.61 mmol) in dimethylformamide (1.5 mL) and sodium sulphide nonahydratate (2.59 g, 2.87 mmol) in hot water (2.3 mL) were added simultaneously and dropwisely. This mixture was heated under reflux for 2 h. The reaction was extracted with ethyl acetate (4×80 mL) and washed with water (2×85 mL). The combined organic layers were dried with anhydrous sodium sulphate and the solvent was evaporated under reduced pressure. The crude was purified by thin layer chromatography [ethyl acetate/hexane (1:8)] affording 2 as a white solid (quantitative yield). mp 53-55° C.; IR (KBr)

$v_{max}$=776, 1077, 1201, 1228, 1693, 1707 cm$^{-1}$. $^1$H NMR (400 MHz, CDCl$_3$) δ (ppm)=1.35 (t, J=7.0 Hz, 6H), 2.56 (s, 6H), 3.62 (s, 4H), 4.28 (q, J=7.0 Hz, 4H), 6.43 (s, 2H); $^{13}$C NMR (100 MHz, CDCl$_3$) δ (ppm)=13.9, 14.4, 27.5, 60.2, 108.6, 114.2, 148.8, 159.1, 163.9; HRMS (EI) calcd for C$_{18}$H$_{22}$O$_6$S 366.1137 [M$^+$], found 366.1138.

Bis((3-carboxy-2-methyl-furan-5-yl)methyl)sulfane (3) (AT-09-A00): to a solution of furan 2 (0.10 g, 0.27 mmol) in ethanol (3.0 mL) an aqueous saturated solution of potassium hydroxide (5 mL) was added dropwise. The reaction mixture was stirred at room temperature for 58 hours during which more potassium hydroxide solution portions were added. Subsequently, the mixture was acidified to pH 2 with aqueous solution of 1 M HCl and extracted twice with ethyl acetate. The combined organic layers were dried with anhydrous sodium sulphate and the solvent evaporated under reduced pressure. Recrystallization with ethyl acetate/hexane afforded the desired acid 3 (AT-09-A00) as a white solid (0.04 g, 50%). Decompose>275° C.; IR (KBr) $v_{max}$=778, 1089, 1239, 1674, 1681 cm$^{-1}$. $^1$H NMR (400 MHz, DMSO-d$_6$) δ (ppm)=2.48 (s, 6H), 3.72 (s, 4H), 6.41 (s, 2H), 12.49 (s, 2H); $^{13}$C NMR (100 MHz, DMSO-d$_6$) δ (ppm)=13.3, 27.0, 108.5, 114.4, 149.3, 157.8, 164.6; HRMS (EI) calcd for C$_{14}$H$_{14}$O$_6$S 310.0511 [M$^+$], found 310.0507.

In an embodiment, the synthesis of (E)-ethyl 5-(2-(5-chlorofuran-2-yl)vinyl)-4-methylfuran-3-carboxylate (9) (AT-09-B00) was carried out as follows: _Ethyl 5-chloromethyl-4-methyl-3-furoate (5): the chloromethylation of furan 4 was carried out using an analogous method to that described in the literature [44]. To a solution of furan 4 (5.19 mmol), paraformaldehyde (0.24 g, 7.79 mmol) and zinc chloride (0.32 g, 1.2 mmol) in chloroform (4.2 mL), a solution of HCl 2M in diethyl ether (11.2 mL, 1.2 mmol) was added, under nitrogen atmosphere. After vigorous stirring for 3 hours, the mixture was cooled to room temperature and treated with water. The organic layer was separated and the aqueous layer was extracted with chloroform (3×50 mL). The combined organic layers were washed with water until neutral pH was observed, dried with anhydrous sodium sulphate and evaporated under reduced pressure affording furan 5 as dark yellow oil (0.94 g, 94%). IR (KBr) $v_{max}$=651, 710, 777, 1079, 1213, 1260, 1709 cm$^{-1}$. $^1$H NMR (400 MHz, CDCl$_3$) δ (ppm)=1.34 (t, J=7.2 Hz, 3H) 2.24 (s, 3H), 4.29 (q, J=7.2 Hz, 2H), 4.58 (s, 2H), 7.95 (s, 2H); $^{13}$C NMR (100 MHz, CDCl$_3$) δ (ppm)=9.2, 14.3, 35.5, 60.2, 119.8, 120.0, 147.6, 148.1, 163.3. ((4-(Ethoxycarbonyl)-3-methyl-furan-2-yl)methyl)triphenylphosphonium chloride (6): to a stirred solution of 5 (1.24 g, 6.12 mmol) in dry toluene (5.5 mL) at room temperature, triphenylphosphine (1.78 g, 6.73 mmol) was added. This mixture was heated under reflux for 12 h. The salt was separated by filtration, washed with diethyl ether and purified by crystallization (ethanol/diethyl ether) affording compound 6 as a yellow solid (2.32 g, 82%). mp 201-203° C.; IR (KBr) $v_{max}$=509, 519, 690, 744, 1067, 1304, 1439, 1695, 1708 cm$^{-1}$.

$^1$H NMR (400 MHz, DMSO-d$_6$) δ (ppm)=1.21 (t, J=7.2 Hz, 3H), 1.65 (d, J=3.6 Hz, 3H), 4.16 (q, J=7.2 Hz, 2H), 5.45 (d, J=14.4 Hz, 2H), 7.76-7.80 (m, 12H, Ar—H), 7.90-7.93 (m, 3H, Ar—H), 8.19 (d, J=2.4 Hz, 1H); $^{13}$C NMR (100 MHz, DMSO-d$_6$) δ (ppm)=8.2, 14.0, 21.2 (d, $^1J_{CP}$=54.9 Hz), 59.9, 117.8 ($^1J_{CP}$=85.0 Hz), 119.1 (d, $^4J_{CP}$=3.2 Hz), 121.2 ($^3J_{CP}$=8.7 Hz), 130.0, 130.1, 133.8, 133.9, 135.1, 139.8 (d, $^2J_{CP}$=11.5 Hz), 149.4 (d, $^4J_{CP}$=3.1 Hz), 162.2; $^{31}$P NMR (161.97 MHz, DMSO-d$_6$) δ (ppm)=20.70; HRMS (ESI) calcd for C$_{27}$H$_{26}$O$_3$P 429.1615 [M$^+$-Cl], found 429.1614.

(E)-ethyl 5-(2-(5-chlorofuran-2-yl)vinyl)-4-methylfuran-3-carboxylate (8): to a reaction mixture of 6 (1.49 g, 3.23 mmol) and 5-chlorofuran-2-carbaldehyde (0.45 g, 3.23 mmol) in dried ethanol (5.3 mL) heated at reflux, a sodium ethoxide solution (0.24 g of metallic sodium in 9.0 mL of freshly dried ethanol) was added dropwise. The mixture was further heated at reflux for 3.5 h. The solvent was evaporated under reduced pressure and the crude purified by flash chromatography [ethyl acetate/hexane (1:10)-(1:6)] giving a dark brown oil (0.3 g, 33%). The product was obtained as E and Z isomeric mixture (75:25) and used in the following step without further purification. $^1$H NMR (400 MHz, CDCl$_3$) δ (ppm)=1.35 (t, J=7.2 Hz, 3H), 2.21 (s, 3H, for Z isomer), 2.28 (s, 3H, for E isomer), 4.30 (q, J=7.2 Hz, 2H), 6.09 (d, J=16.0 Hz, 2H, for Z isomer), 6.19 (d, J=3.2 Hz, 1H, for E isomer), 6.29 (d, J=3.2 Hz, 1H, for E isomer), 6.67 (d, J=16.0 Hz, 1H, for E isomer), 6.77 (d, J=16.0 Hz, 1H, for E isomer), 6.93 (d, J=3.2 Hz, 1H, for Z isomer), 7.90 (s, 1H, for E isomer), 8.01 (s, 1H, for Z isomer); $^{13}$C NMR (100 MHz, CDCl$_3$, for E isomer) δ (ppm)=9.1, 14.2, 60.0, 108.4, 110.7, 113.7, 118.8, 120.5, 136.0, 147.2, 149.9, 152.4, 163.4.

(E)-5-(2-(5-chlorofuran-2-yl)vinyl)-4-methylfuran-3-carboxylic acid (9) (AT-09-B00): to a stirred solution of 8 (0.10 g, 0.36 mmol) in ethanol (3.0 mL), an aqueous saturated solution of potassium hydroxide (5 mL) was added dropwise. After 3 h, the reaction was completed and the mixture was acidified to pH 2 with aqueous solution of 3M HCl and extracted twice with dichloromethane. The combined organic layers were dried with anhydrous sodium sulphate and the solvent evaporated under reduced pressure. Recrystallization (acetone/hexane) afforded the desired E-isomer of 9 (AT-09-B00) as an orange solid (0.04 g, 44%). mp 184-186° C. IR (KBr) $v_{max}$=594, 769, 947, 1158, 1327, 1486, 1673, 1690, 2974 cm$^{-1}$. $^1$H NMR (400 MHz, DMSO-d$_6$) δ (ppm)=2.23 (s, 3H), 6.55 (d, J=3.2 Hz, 1H), 6.69 (d, J=3.2 Hz, 1H), 6.73 (d, J=16.2 Hz, 1H), 6.83 (d, J=16.2 Hz, 1H), 8.24 (s, 1H), 12.69 (s, 1H); $^{13}$C NMR (100 MHz, DMSO-d$_6$) δ (ppm)=8.8, 109.4, 111.7, 112.6, 113.5, 119.0, 120.7, 134.7, 148.4, 149.3, 152.3, 164.1; HRMS (EI) calcd for C$_{12}$H$_9$ClO$_4$ 252.0189 [M$^+$], found 252.0182.

In an embodiment, the synthesis of (E)-5-(2-(5-chlorofuran-2-yl)vinyl)-1-methylfuran-3-carboxylic acid (12) (AT-09-B06) was carried out as follows: ((4-(Ethoxycarbonyl)-5-methylfuran-2-yl)methyl)triphenylphosphonium chloride (10): to a stirred solution of furan 1 (4.0 g, 19.7 mmol) in dry toluene (18 mL) at room temperature, triphenylphosphine (5.70 g, 21.7 mmol) was added. This mixture was heated under reflux for 12 h. The salt was separated by filtration, washed with diethyl ether and purified by crystallization (ethanol/diethyl ether) affording compound 10 as a yellow solid (6.78 g, 74%). mp 236-238° C.; IR (KBr) $v_{max}$=502, 521, 687, 717, 1074, 1220, 1292, 1436, 1711 cm$^{-1}$.

$^1$H NMR (400 MHz, DMSO-d$_6$) δ (ppm)=1.21 (t, J=7.2 Hz, 3H), 2.30 (d, J=3.2 Hz, 3H), 4.16 (q, J=7.2 Hz, 2H), 5.55 (d, J=14.8 Hz, 2H), 6.40 (d, J=4.4 Hz, 1H), 7.77-7.79 (m, 12H, Ar—H), 7.91-7.93 (m, 3H, Ar—H); $^{13}$C NMR (100 MHz, DMSO-d$_6$) δ (ppm)=13.2, 14.1, 22.7 (d, $^1J_{CP}$=50.6 Hz), 60.1, 112.3 (d, $^3J_{CP}$=8.2 Hz), 114.1, 117.8 ($^1J_{CP}$=85.4 Hz), 130.1, 130.2, 133.8, 133.9, 135.2, 140.7 (d, $^2J_{CP}$=11.0 Hz), 159.2, 162.4; $^{31}$P NMR (161.97 MHz, DMSO-d$_6$) δ (ppm)=20.53; HRMS (ESI) calcd for C$_{27}$H$_{26}$O$_3$P 429.1615 [M+-Cl], found 429.1614.

(E)-ethyl 5-(2-(5-chlorofuran-2-yl)vinyl)-1-methylfuran-3-carboxylate (11): to a reaction mixture of 10 (4.0 g, 8.60 mmol) and 5-chlorofuran-2-carbaldehyde (1.12 g, 8.60 mmol) in dried ethanol (11 mL) heated at reflux, a sodium ethoxide solution (0.24 g of metallic sodium in 9.0 mL of freshly dried ethanol) was added dropwise. The mixture was further heated at reflux for 3.5 h. The solvent was evaporated under reduced pressure and the crude purified by flash chromatography [ethyl acetate/hexane (1:5)-(1:4)] giving a dark brown oil (1.2 g, 50%). The product was obtained as E and Z isomeric mixture (70:40). Recrystallization (ethyl acetate/hexane) afforded the desired E-isomer of 11 as a yellow solid (71.1 mg). $^1$H NMR (400 MHz, CDCl$_3$) δ (ppm)=1.35 (t, J=7.2 Hz, 3H), 2.60 (s, 3H), 4.29 (q, J=7.2 Hz, 2H), 6.18 (d, J=3.4 Hz, 1H), 6.28 (d, J=3.4 Hz, 1H), 6.54 (s, 1H), 6.65 (d, J=16.0 Hz, 1H), 6.69 (s, 1H); $^{13}$C NMR (100 MHz, CDCl$_3$) δ (ppm)=13.9, 14.4, 60.2, 108.5, 109.5, 110.8, 114.2, 114.4, 115.6, 136.3, 150.4, 152.3, 159.0, 163.8.

(E)-5-(2-(5-chlorofuran-2-yl)vinyl)-1-methylfuran-3-carboxylic acid (12) (AT-09-B06): to a stirred solution of 11 (65.6 mg, 0.23 mmol) in ethanol (2.5 mL), an aqueous saturated solution of potassium hydroxide (5 mL) was added dropwise. After 3 h, the reaction was completed and the mixture was acidified to pH 2 with aqueous solution of 3M HCl and extracted twice with dichloromethane. The combined organic layers were dried with anhydrous sodium sulphate and the solvent evaporated under reduced pressure. Recrystallization (acetone/hexane) afforded the desired E-isomer of 12 (AT-09-B06) as a yellow solid (52 mg, 89%). mp 186-188° C.; IR (KBr) $v_{max}$=774, 798, 950, 1015, 1259, 1457, 1653, 1669, 2960 cm$^{-1}$. $^1$H NMR (400 MHz, DMSO-d$_6$) δ (ppm)=2.55 (s, 3H), 6.55 (d, J=3.2 Hz, 1H), 6.65 (d, J=3.2 Hz, 1H), 6.71 (s, 1H), 6.75 (bs, 2H), 12.63 (br s, 1H); $^{13}$C NMR (100 MHz, DMSO-d$_6$) δ (ppm)=13.5, 109.3, 110.5, 111.9, 113.8, 114.2, 115.9, 134.8, 149.8, 152.1, 158.5, 164.4; HRMS (EI) calcd for $C_{12}H_9ClO_4$ 252.0189 [M$^+$], found 252.0184.

In an embodiment, the protein expression and purification was conducted as follows: recombinant human wild-type TTR (WT-TTR) was expressed in BL21 (DE3) *E. coli* cells (NZYTech) transformed with the pET23a plasmid containing the TTR and ampicillin-resistance genes. The transformed cells were grown in Luria Broth and the WT-TTR expression was achieved by induction with 1 mM IPTG for 4 hours. After cell harvesting and a freeze/thaw cycle, the cells were sonicated and the insoluble materials pelleted by centrifugation. The protein purification protocol comprises an initial precipitation step with ammonium sulphate, followed by anionic exchange chromatography and size exclusion chromatography, as previously reported [57]. The concentrations of WT-TTR solutions were determined spectrophotometrically at 280 nm, using an extinction coefficient of 7.76×10$^4$ M$^{-1}$·cm$^{-1}$, based on a 55 kDa molecular mass for the TTR tetramer [58].

In an embodiment, the compound preparation for amyloid fibril formation assay was conducted as follows: compounds were prepared as 10.8 mM stock solutions in pure DMSO. Several dilutions in DMSO of the stock solution were made to provide secondary stock solutions. The concentrations were chosen depending on the efficacy of the compound in inhibiting the formation of TTR amyloid fibrils.

In an embodiment, the amyloid fibril formation assay used in this disclosure was based on the one presented in reference [46] and adapted to run in a 96-well microplate. For this purpose, 1 μL of different compound secondary stock solutions was added to 50 μL of a 7.2 μM WT-TTR solution in 10 mM sodium phosphate buffer, 100 mM KCl and 1 mM EDTA, pH 7.2, previously dialyzed against the same buffer solution. After 30 minutes of incubation at room temperature, the pH of the mixture was lowered to 4.4 with 49 μL of 200 mM acetate buffer, 100 mM KCl and 1 mM EDTA, pH 4.3. The final 100 μL solutions per well have the following composition: 1% DMSO, 3.6 μM of WT-TTR and a variety of compound concentrations which may range between 0.72 μM (0.2×TTR) to 36 μM (10×TTR). The mixtures were incubated at 37° C. for 72 hours.

In an embodiment, the turbidity at 405 nm, 450 nm and 490 nm (or 550, 600 and 650 nm when the compound absorbs at the previous wavelengths) was measured over time using a microplate spectrophotometer (BioTek Instruments, Inc. Winooski, Vt., USA) to evaluate the extent of fibril formation. Immediately before the turbidity measurements, the mixtures were gently shaken for 1 minute for homogenization but to avoid damaging the formed amyloid aggregates and fibrils. The final turbidity for each compound concentration tested in triplicate was calculated as an average of the three wavelengths measured. In addition, control samples containing TTR with no inhibitor and 1% DMSO, as well as inhibitor in absence of TTR, were tested and analyzed. All compounds were found to be soluble throughout the course of the experiment, ensuring that turbidity was the result of TTR amyloid fibril formation.

In an embodiment, the extent of amyloid fibril formation was compared to WT-TTR with no inhibitor, assigned to be 100% amyloid fibril formation (or 0% amyloid inhibition) at the end of the experiment.

In this disclosure, the IC$_{50}$ is defined as the concentration of a test compound that inhibits the formation of TTR amyloid by 50%. IC$_{50}$ values were determined by monitoring the effect of increasing concentrations of the compounds under test on the inhibition values. Ten different compound concentrations were used for each IC$_{50}$ assay, along with a fixed WT-TTR concentration (3.6 μM). The extent of amyloid fibril formation throughout 72 hours was determined as described in the discussion of the Amyloid fibril formation assay. IC$_{50}$ values were determined by non-linear least square fitting of the inhibition curves using the program OriginPro7 (OriginLab Corporation, USA).

In an embodiment, the isothermal titration calorimetry (ITC) experiments were performed on a Malvern high precision VP-ITC titration calorimetry system (Malvern Instruments, Worcestershire, UK; previously from MicroCal). Compound stock solutions were prepared in pure DMSO. Both compound and WT-TTR dilutions were prepared in 20 mM sodium phosphate buffer, 150 mM sodium chloride and 2% DMSO, at pH 7.2. All solutions were filtered and degassed prior to use. Direct titrations were performed at 25° C. to study tafamidis (150 μM), AT09-B00 (130 μM) and AT09-B06 (130 μM), using the classic setup with ligand solutions in the syringe and protein WT-TTR (7 μM) in the calorimetric cell.

In an embodiment, in all titrations, the initial injection of 4 μL of titrant to the calorimetric cell was followed by 28 injections at regular intervals of 10 μL each, until saturation of the titrated solution was reached. Injections were separated by 450 s for tafamidis and 350 s for AT09-B00 and AT09-B06 to allow equilibration. The extent of binding was determined by direct measurement of the heat exchanged with the environment: the heat associated with each injection is proportional to the complex concentration and can be calculated by integrating the area under the deflection of the measured calorimetric signal. Data were analyzed with the Origin 7.0 software package from Malvern. A baseline correction was applied to each experiment by subtraction of data from injections of ligand solution into a buffer blank correlating to the heat of dilution of the ligand solution. For the calculation of the association constant (K$_a$), data analysis was performed according to a model of binding to a macromolecule with two ligand-binding sites, by non-linear regression [46]. The reported dissociation constant ($K_d$) is the reciprocal of $K_a$, according to the equation $\Delta G= -RTlnK_a=RTlnK_d$, where $\Delta G$ is the Gibbs free energy of binding, R is the gas constant and T is the temperature.

In an embodiment, the ex vivo thyroxine competition assays were conducted. Binding to TTR in human plasma was evaluated through a competition assay with radioactive thyroxine ($[^{125}I]$-T4]) and monitored by gel electrophoresis as described in reference [52]. In short, 5 µL of human plasma, 0.25-0.5 µL of [$^{125}I$]-T4 (specific radioactivity 1250 µCi/mL; concentration 320 µCi/mL; Perkin Elmer, Boston, Mass., USA) and 5 µL of phosphate-buffered saline (PBS) with 10% glycerol are incubated for 1 hour at room temperature and the samples are subjected to native polyacrylamide gel electrophoresis (PAGE). After electrophoresis, the gels are dried, subjected to phosphor imaging (Typhoon 8600; Molecular Diagnostics, Amersham Biosciences), and analysed using the ImageQuant program version 5.1. The intensity of the protein bands is compared. Two or three bands of different intensity should be visualized in plasma samples. The bands correspond to the major T4-binding plasma proteins, namely albumin (ALB), transthyretin (TTR) and thyroxine-binding globulin (TBG). The intensity of the bands should be decreased, as compared to the control samples (absence of compound), if the compound competes with T4 for binding to TTR.

The results are analyzed by calculation of the TTR/total (TTR+ALB+TBG) ratio for each sample. The displacement of T4 from TTR is calculated as the difference between the average of ratios of TTR/total protein for the control sample and the average of the ratios of TTR/total protein for each sample.

In an embodiment, ex vivo TTR stability assays were conducted. Plasma TTR stability to dissociation is assessed by isoelectric focusing (IEF) in semi-denaturing conditions of human plasma samples as described in references [51,52]. To perform the assay, 30 µL of human plasma are incubated with 5 µL of a 10 mM solution of test compounds and control compounds overnight at 4° C. followed by a 1 hour incubation at room temperature. The samples are then subjected to native PAGE and the gel band containing TTR is excised and applied to an IEF gel. IEF is carried out in semi-denaturing conditions (4 M urea), containing 5% (v/v) ampholytes pH 4-6.5 (GE Healthcare), at 1200 V for 6 hours. Proteins are stained with Coomassie Blue, the gels are scanned and subjected to densitometry using the ImageQuant program. The results are expressed as the average ratio of TTR tetramer for over total TTR over 5 repetitions±the standard deviation.

In an embodiment, the HepG2 cell viability assay was conducted as follows:

Adherent human hepatoma cells HepG2 were cultured in DMEM (Dulbecco's Modified Eagle's Medium) with 10% fetal bovine serum (FBS), 100 U/mL penicillin, 100 µg/mL streptomycin, and 1 mM sodium pyruvate. The cells were grown in 75 cm$^2$ culture flasks at 37° C., in an atmosphere of 5% $CO_2$, and subcultured twice a week using a trypsin-EDTA solution.

Upon 3-4 days of growth and reaching approximately 90-95% confluence, HepG2 cells were plated in 96-well microplates with cell density of 12×10$^3$ cells/well and in a volume of 100 µL per well. Preliminary studies indicated that this cell density is optimal for HepG2 cells which show a linear increase over 72 hours of incubation at 37° C. and 5% $CO_2$ (data not shown).

In this assay, the compounds were dissolved in pure DMSO and subsequently diluted in DMEM (in 9 intermediate compound concentrations). After adhesion of HepG2 cells to the microplates, 100 µL of each solution of intermediate compound concentration was added to each well (in quadruplicate). Positive controls with 10 wells containing only cells were tested; solvent controls resulted from the analyses of the three highest DMSO concentrations tested and were carried out in triplicate.

After addition of the compounds to the cells, the microplates were incubated for approximately 72 hours at 37° C. in an atmosphere of 5% $CO_2$ until the cell viability assay was performed.

The viability of HepG2 cells in the presence of test compounds was assessed by the resazurin reduction assay [59]. A stock solution of 0.01% resazurin in PBS is diluted 1:10 in incomplete RPMI 1640 cell medium (without addition of antibiotics and FBS). After washing the cells with 200 µL PBS containing $Ca^{2+}$ and $Mg^{2+}$, 200 µL of 0.001% resazurin were added to the wells. Blanks with incomplete RPMI 1640 medium alone were done in triplicate. The microplates were incubated at 37° C. and 5% $CO_2$ for approximately 2-4 hours.

To quantify the reduction of resazurin, microplate absorbance readings were taken at two wavelengths, 540 nm (reduced form) and 630 nm (oxidized form), in a microplate spectrophotometer (BioTek Instruments, Inc.). The percentage of viable cells at each compound concentration was determined using the equation $$\% \text{ viable cells}=[(\varepsilon_{630\ nm}\times Abs_{540\ nm})-(\varepsilon_{540\ nm}\times Abs_{630\ nm})]/[(\varepsilon_{630\ nm}\times Ctrl_{540\ nm})-(\varepsilon_{540\ nm}\times Ctrl_{630\ nm})]$$

where $\varepsilon$ is the molar extinction coefficient, Abs is the absorbance and Ctrl is the absorbance of the positive control (cells without compound).

$ID_{50}$ values express the inhibitory dose of each test compound at 50% of the dose-response curve and were determined by non-linear least square fitting to the experimental points using the program OriginPro7 (OriginLab Corporation, USA).

Certain aspects of the present disclosure provide pharmaceutical preparations comprising a compound, pharmaceutically acceptable salt, solvate, hydrate, tautomer, stereoisomer, or prodrug thereof as described herein and a pharmaceutically acceptable carrier. The compound, pharmaceutically acceptable salt, solvate, hydrate, tautomer, stereoisomer, or prodrug thereof is also referred to herein as an active ingredient, active agent, or active compound of the pharmaceutical preparation. Additional active agents may, however, be present, e.g., an additional therapeutic agent, such as, for example, Tafamidis, Tolcapone, Donepezil, Patisiran or Resuviran. The pharmaceutical preparations provided herein are suitable for the respective route of administration. For example, a pharmaceutical preparation for parenteral administration is typically sterile and essentially non-pyrogenic. In some embodiments, preparations for other administration routes are also sterile and non-pyrogenic.

Some aspects of this disclosure provide pharmaceutical preparations comprising a compound as provided herein, e.g., a compound as provided in FIG. 2, 3, or 4, or a pharmaceutically acceptable salt, solvate, hydrate, tautomer, stereoisomer, or prodrug thereof. In some embodiments, the pharmaceutical preparation comprises a compound, pharmaceutically acceptable salt, solvate, hydrate, tautomer, stereoisomer, or prodrug thereof as described elsewhere herein. In some embodiments, the pharmaceutical preparation comprises a chemical delivery system (CDS), for example, comprised in or conjugated to the compound, pharmaceutically acceptable salt, solvate, hydrate, tautomer, stereoisomer, or prodrug thereof. In some embodiments, the CDS enhances delivery of the compound to the central nervous system, e.g., to the brain. In some embodiments, the CDS enhances delivery of the compound across the blood brain barrier.

In some embodiments, the preparation is for administration to a human subject. In some embodiments, the preparation is sterile. In some embodiments, the preparation is essentially pyrogen-free. In some embodiments, the preparation is pyrogen-free.

Typically, the pharmaceutical preparations provided herein comprise an amount of the active ingredient, e.g., of a compound described herein, that is effective to achieve a desired effect in a subject after administration to the subject.

For example, in some embodiments, the preparation comprises the compound, or the pharmaceutically acceptable salt, solvate, hydrate, tautomer, stereoisomer, or prodrug thereof in an amount effective to inhibit amyloid fibril formation in a subject. In some embodiments, the amyloid fibril formation is transthyretin (TTR) amyloid fibril formation. In some embodiments, the preparation comprises the compound, or the pharmaceutically acceptable salt, solvate, hydrate, tautomer, stereoisomer, or prodrug thereof, in an amount effective to decrease the level of amyloid fibril formation by at least 5%, at least 10%, at least 15%, at least 20%, at least 25%, at least 30%, at least 40%, at least 50%, at least 60%, at least 70%, at least 75%, at least 80%, at least 90%, at least 95%, at least 95.7%, at least 98%, or at least 99% in the subject.

In some embodiments, the preparation comprises the compound, or the pharmaceutically acceptable salt, solvate, hydrate, tautomer, stereoisomer, or prodrug thereof, in an amount effective to increase TTR stability in the subject. In some embodiments, the preparation comprises the compound, or the pharmaceutically acceptable salt, solvate, hydrate, tautomer, stereoisomer, or prodrug thereof, in an amount effective to increase serum or plasma TTR stability in the subject. In some embodiments, the preparation comprises the compound, or the pharmaceutically acceptable salt, solvate, hydrate, tautomer, stereoisomer, or prodrug thereof, in an amount effective to increase the ratio of tetrameric TTR to monomeric TTR in the subject. In some embodiments, the preparation comprises the compound, or the pharmaceutically acceptable salt, solvate, hydrate, tautomer, stereoisomer, or prodrug thereof, in an amount effective to increase the level of tetrameric TTR in the subject and/or to decrease the level of monomeric TTR in the subject.

In some embodiments, the pharmaceutical preparation comprises the compound, or the pharmaceutically acceptable salt, solvate, hydrate, tautomer, stereoisomer, or prodrug thereof, in an amount effective to increase the stability of TTR, increase the level of tetrameric TTR, decrease the level of monomeric TTR, and/or increase the ratio of tetrameric to monomeric TTR in the subject by at least 2%, at least 2.5%, at least 3%, at least 4%, at least 5%, at least 6%, at least 7%, at least 7.5%, at least 8%, at least 9%, at least 10%, at least 12%, at least 12.5%, at least 15%, at least 20%, at least 25%, at least 30%, at least 50%, at least 60%, at least 70%, at least 75%, at least 80%, at least 95%, or at least 99% as compared to the stability, level, or ratio in the absence of the compound, the pharmaceutically acceptable salt, solvate, hydrate, tautomer, stereoisomer, or prodrug thereof.

In some embodiments, the preparation comprises the compound, or the pharmaceutically acceptable salt, solvate, hydrate, tautomer, stereoisomer, or prodrug thereof, in an amount effective to increase the ratio of tetrameric to monomeric TTR in the subject to at least 0.72, at least 0.75, at least 0.8, at least 0.85, at least 0.9, at least 0.95, at least 0.98, or at least 0.99, and/or to maintain such a ratio in the subject. In some embodiments, the ratio of tetrameric to monomeric TTR in the subject before administration of the pharmaceutical preparation is lower than the ratio observed or expected in a healthy subject, lower than the average ratio observed in an age- and gender-matched population, or less than 0.72, less than 0.71, less than 0.7, less than 0.69, less than 0.68, less than 0.67, less than 0.66, less than 0.65, or less than 0.5. In some embodiments, the subject carries a TTR mutation associated with an amyloid disease. In some embodiments, the subject carries a TTR mutation associated with an amyloid disease but does not exhibit an abnormal TTR stability or a symptom of the amyloid disease.

In some embodiments, the preparation comprises the compound, or the pharmaceutically acceptable salt, solvate, hydrate, tautomer, stereoisomer, or prodrug thereof in an amount effective to ameliorate at least one symptom of an amyloid disease in the subject. In some embodiments, the symptom is neuropathy, neurological impairment, neurological dysfunction, cognitive deficiency, nutritional deficiency, and decreased TTR stability. In some embodiments, the amyloid disease is AA amyloidosis, Alzheimer's disease, Light-Chain (AL) amyloidosis, Type-2 Diabetes, Medullary Carcinoma of the Thyroid, Parkinson's disease, Polyneuropathy, Spongiform Encephalopathy (Creutzfeldt Jakob disease), Familial Amyloid Polyneuropathy, Familial Amyloid Cardiomyopathy, or Senile Systemic Amyloidosis.

In some embodiments, the preparation comprises a dose of 0.1-1000 mg of the compound or the pharmaceutically acceptable salt, solvate, hydrate, tautomer, stereoisomer, or prodrug thereof per kg body weight of the subject. For example, in some embodiments, the preparation comprises a dose of 0.1 mg/kg, 0.2 mg/kg, 0.3 mg/kg, 0.4 mg/kg, 0.5 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 200 mg/kg, 250 mg/kg, 300 mg/kg, 400 mg/kg, 500 mg/kg, 600 mg/kg, 700 mg/kg, 750 mg/kg, 800 mg/kg, 900 mg/kg, or 1000 mg/kg. In some embodiments, the preparation comprises a dose of 0.1-10 mg/kg, 0.1-100 mg/kg, 1-10 mg/kg, 1-100 mg/kg, 1-1000 mg/kg, 10-100 mg/kg, 10-1000 mg/kg, 100-1000 mg/kg, 10-50 mg/kg, 10-25 mg/kg, 10-20 mg/kg, 50-100 mg/kg, or 100-250 mg/kg, In some embodiments, the pharmaceutical preparation is provided in a dosage form, e.g., in a dosage form for parenteral or for oral administration. In some such embodiments, the pharmaceutical preparation is in the form of a dosage form for oral administration, e.g., in the form of a pill, tablet, capsule, lozenge, gel, or other suitable dosage form. In some embodiments, the dosage form for administration comprises 1 mg, 2 mg, 3 mg, 4 mg, 5 mg, 6 mg, 7 mg, 8 mg, 9 mg, 10 mg, 15 mg, 20 mg, 25 mg, 30 mg, 40 mg, 50 mg, 60 mg, 70 mg, 80 mg, 90 mg, 100 mg, 200 mg, 250 mg, 300 mg, 400 mg, 500 mg, 600 mg, 700 mg, 750 mg, 800 mg, 900 mg, or 1000 mg of the compound, or the pharmaceutically acceptable salt, solvate, hydrate, tautomer, stereoisomer, or prodrug thereof.

In some embodiments, the dosage form comprises 0.1-10 mg, 0.1-100 mg, 1-10 mg, 1-100 mg, 1-1000 mg, 10-100 mg, 10-1000 mg, 100-1000 mg, 10-50 mg, 10-25 mg, 10-20 mg, 50-100 mg, or 100-250 mg of the compound, or the pharmaceutically acceptable salt, solvate, hydrate, tautomer, stereoisomer, or prodrug thereof.

In some embodiments, the preparation comprises a micronized form of the compound or of the pharmaceutically acceptable salt, solvate, hydrate, tautomer, stereoisomer, or prodrug thereof. Suitable methods for micronization of compounds are known to those of skill in the art and the disclosure is not limited in this respect.

In some embodiments, the pharmaceutical preparation further comprises at least one additional compound, or a pharmaceutically acceptable salt, solvate, hydrate, tautomer, stereoisomer, or prodrug thereof, wherein the at least one additional compound is approved for therapy of an amyloid disease. Such compositions allow for combination therapy of amyloid diseases. In some embodiments, such combination therapy is used to achieve an additive or synergistic effect of the therapeutic compounds used. In some such embodiments, the compounds are administered at their maximum tolerated dose to achieve the maximum therapeutic effect.

In other embodiments, the subject to be treated with the combination is a subject in which monotherapy has not yielded the desired effect. In some embodiments, administering a single compound to treat amyloid disease, e.g., a compound already approved for human treatment or in clinical trials, is not successful in the subject because the compound is toxic or causes unacceptable side effects when administered to the subject at effective doses. In such cases, a combination therapy may be employed in which two compounds targeted at ameliorating a symptom of the amyloid disease are administered at sub-toxic doses to yield an additive or synergistic therapeutic effect without the toxicity associated with single compound treatment regimen. For example, in some embodiments, the additional compound is Tafamidis, Tolcapone, Donepezil, Patisiran or Resuviran.

In some embodiments, a pharmaceutical preparation provided herein is for use in the treatment of an amyloid disease, for example, AA amyloidosis, Alzheimer's disease, Light-Chain (AL) amyloidosis, Type-2 Diabetes, Medullary Carcinoma of the Thyroid, Parkinson's disease, Polyneuropathy, or Spongiform Encephalopathy (Creutzfeldt Jakob disease).

In some embodiments, a compound, or a pharmaceutically acceptable salt, solvate, hydrate, tautomer, stereoisomer, or prodrug thereof, described herein is administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the active agent, e.g., the compound, or a pharmaceutically acceptable salt, solvate, hydrate, tautomer, stereoisomer, or prodrug thereof, can be administered to a subject by any mode that delivers the active agent to the desired surface. Administering the pharmaceutical preparation of the present disclosure may be accomplished by any means known to the skilled artisan. Preferred routes of administration include but are not limited to oral, parenteral, intramuscular, intranasal, sublingual, intratracheal, and inhalation.

For oral administration, the compounds (e.g., a compound provided in FIG. 2, 3, or 4), or a pharmaceutically acceptable salt, solvate, hydrate, tautomer, stereoisomer, or prodrug thereof, or other therapeutic agents) can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the active agent (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the active agent (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the active agent or derivative either alone or as a mixture in different ratios.

Pharmaceutical preparations that can be used orally include push-fit capsules made of gelatin, as well as soft, sealed capsules made of gelatin and a plasticizer, such as glycerol or sorbitol.

The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the active agents (or derivatives thereof). The active agent (or derivative) is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this disclosure are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this disclosure are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

Such devices use formulations suitable for the dispensing of active agent (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified active agent may also be prepared in different formulations depending on the type of chemical modification or the type of device employed.

Formulations suitable for use with a nebulizer, either jet or ultrasonic, will typically comprise active agent (or derivative) dissolved in water at a concentration of about 0.1 to 25 mg of biologically active agent per mL of solution. The formulation may also include a buffer and a simple sugar (e.g., for active agent stabilization and regulation of osmotic pressure). The nebulizer formulation may also contain a surfactant, to reduce or prevent surface induced aggregation of the active agent caused by atomization of the solution in forming the aerosol.

Formulations for use with a metered-dose inhaler device will generally comprise a finely divided powder containing the active agent (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing active agent (or derivative) and may also include a bulking agent, such as lactose, sorbitol, sucrose, or mannitol in amounts which facilitate dispersal of the powder from the device, e.g., 50 to 90% by weight of the formulation. The active agent (or derivative) should most advantageously be prepared in particulate form with an average particle size of less than 10 micrometers (μm), most preferably 0.5 to 5 μm, for most effective delivery to the distal lung.

Nasal delivery of a pharmaceutical preparation of the present disclosure is also contemplated. Nasal delivery allows the passage of a pharmaceutical preparation of the present disclosure to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical preparation of the present disclosure solution into a chamber of defined volume, which chamber has an aperture dimensioned to aerosolize and aerosol formulation by forming a spray when a liquid in the chamber is compressed. The chamber is compressed to administer the pharmaceutical preparation of the present disclosure. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds described herein, or the pharmaceutically acceptable salts, solvates, hydrates, tautomers, stereoisomers, or prodrugs thereof, may also be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical preparations for parenteral administration include aqueous solutions of the active agent(s) in water-soluble form. Additionally, suspensions of the active agent(s) may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In some embodiments, the active agent(s) may be in powder form for constitution with a suitable vehicle, e.g., sterile, pyrogen-free water or a suitable buffer, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical preparations also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical preparations also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical preparations are suitable for use in a variety of drug delivery systems. For a brief review of methods for drug delivery, see Langer, *Science* 249:1527-1533, 1990, which is incorporated herein by reference.

The active agents and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The therapeutic agent(s), including specifically but not limited to the active agent, may be provided in particles. Particles as used herein means nano or microparticles (or in some instances larger) which can consist in whole or in part of the active agent or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the active agent in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

Methods of Use

Some aspects of this disclosure provide methods of using the compounds, pharmaceutically acceptable salts, solvates, hydrates, tautomers, stereoisomers, and prodrugs provided herein for inhibiting amyloid fibril formation and for treating amyloid diseases including, but not limited to, Familial Amyloid Polyneuropathy, Familial Amyloid Cardiomyopathy, Senile Systemic Amyloidosis, AA amyloidosis, Alzheimer's disease, Light-Chain (AL) amyloidosis, Type-2 Diabetes, Medullary Carcinoma of the Thyroid, Parkinson's disease, Polyneuropathy, and Spongiform Encephalopathy (Creutzfeldt Jakob disease).

Some aspects of this disclosure provide methods for inhibiting amyloid fibril formation in a subject. The methods comprise administering to a subject in need thereof a compound as provided herein, e.g., a compound provided in FIG. 2, 3, or 4, or a pharmaceutically acceptable salt, solvate, hydrate, tautomer, stereoisomer, or prodrug thereof, or a pharmaceutical preparation provided herein. In some embodiments, the subject exhibits an increased level of amyloid fibril formation as compared to a reference level. In some embodiments, the reference level is a level observed or expected in a healthy subject or a population of healthy subjects. In some embodiments, the amyloid fibril formation is transthyretin amyloid fibril formation. In some embodiments, the subject has or has been diagnosed with an amyloid disease. In some embodiments, the amyloid disease is a transthyretin amyloid disease. In some embodiments, he amyloid disease is Familial Amyloid Polyneuropathy. In some embodiments, the amyloid disease is Familial Amyloid Cardiomyopathy. In some embodiments, the amyloid disease is Senile Systemic Amyloidosis. In some embodiments, the amyloid disease is Alzheimer's Disease.

Some aspects of this disclosure provide methods for treating an amyloid disease. In some embodiments, the method comprising administering to a subject in need thereof a compound provided herein, or a pharmaceutically acceptable salt, solvate, hydrate, tautomer, stereoisomer, or prodrug thereof, or a pharmaceutical preparation provided herein. Typically, such methods comprise administering an amount of the compound, of the pharmaceutically acceptable salt, solvate, hydrate, tautomer, stereoisomer, or prodrug thereof, or of the pharmaceutical preparation to the subject that is effective to ameliorate at least one symptom of the amyloid disease in the subject. In some embodiments, the amyloid disease is AA amyloidosis, Alzheimer's Disease, Light-Chain (AL) amyloidosis, Type-2 Diabetes, Medullary Carcinoma of the Thyroid, Parkinson's disease, Polyneuropathy, or Spongiform Encephalopathy (Creutzfeldt Jakob disease). In some embodiments, the amyloid disease is Familial Amyloid Polyneuropathy, Familial Amyloid Cardiomyopathy, Senile Systemic Amyloidosis.

In some embodiments, the method for inhibiting amyloid fibril formation or for treating an amyloid disease comprises administering an amount of the compound, of the pharmaceutically acceptable salt, solvate, hydrate, tautomer, stereoisomer, or prodrug thereof, or of the pharmaceutical preparation to the subject that is effective to ameliorate at least one symptom of the amyloid disease in the subject. In some embodiments, the method comprises administering the compound, the pharmaceutically acceptable salt, solvate, hydrate, tautomer, stereoisomer, or prodrug thereof, or the pharmaceutical preparation at a dosage of 0.1-1000 mg of the compound or the pharmaceutically acceptable salt, solvate, hydrate, tautomer, stereoisomer, or prodrug thereof per kg body weight of the subject per day. In some embodiments, the method comprises administering a dose as provided herein. For example, in some embodiments, the method comprises administering a dose of 0.1 mg/kg, 0.2 mg/kg, 0.3 mg/kg, 0.4 mg/kg, 0.5 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 200 mg/kg, 250 mg/kg, 300 mg/kg, 400 mg/kg, 500 mg/kg, 600 mg/kg, 700 mg/kg, 750 mg/kg, 800 mg/kg, 900 mg/kg, or 1000 mg/kg to the subject. In some embodiments, the method comprises administering a dose of 0.1-10 mg/kg, 0.1-100 mg/kg, 1-10 mg/kg, 1-100 mg/kg, 1-1000 mg/kg, 10-100 mg/kg, 10-1000 mg/kg, 100-1000 mg/kg, 10-50 mg/kg, 10-25 mg/kg, 10-20 mg/kg, 50-100 mg/kg, or 100-250 mg/kg to the subject. In some embodiments, the method comprises administering a pharmaceutical preparation as provided herein via a parenteral or an oral administration route. For example, in some embodiments, the method comprises administering an oral dosage form, e.g., in the form of a pill, tablet, capsule, lozenge, gel, or other suitable oral dosage form, comprising 1 mg, 2 mg, 3 mg, 4 mg, 5 mg, 6 mg, 7 mg, 8 mg, 9 mg, 10 mg, 15 mg, 20 mg, 25 mg, 30 mg, 40 mg, 50 mg, 60 mg, 70 mg, 80 mg, 90 mg, 100 mg, 200 mg, 250 mg, 300 mg, 400 mg, 500 mg, 600 mg, 700 mg, 750 mg, 800 mg, 900 mg, or 1000 mg of a compound, or a pharmaceutically acceptable salt, solvate, hydrate, tautomer, stereoisomer, or prodrug thereof as provided herein to the subject. In some embodiments, the method comprises administering a dosage form comprises 0.1-10 mg, 0.1-100 mg, 1-10 mg, 1-100 mg, 1-1000 mg, 10-100 mg, 10-1000 mg, 100-1000 mg, 10-50 mg, 10-25 mg, 10-20 mg, 50-100 mg, or 100-250 mg of the compound, or the pharmaceutically acceptable salt, solvate, hydrate, tautomer, stereoisomer, or prodrug thereof.

In some embodiments, the dose or dosage form is administered to the subject once a day, twice a day, or three times a day. In other embodiments, the dose is administered to the subject once a week, once a month, once every two months, four times a year, three times a year, twice a year, or once a year.

In some embodiments, the method for inhibiting amyloid fibril formation or for treating an amyloid disease comprises administering the compound, the pharmaceutically acceptable salt, solvate, hydrate, tautomer, stereoisomer, or prodrug thereof, or the pharmaceutical preparation at a dosage effective to increase the stability of TTR, increase the level of tetrameric TTR, decrease the level of monomeric TTR, and/or increase the ratio of tetrameric to monomeric TTR in the subject by at least 2%, at least 2.5%, at least 3%, at least 4%, at least 5%, at least 6%, at least 7%, at least 7.5%, at least 8%, at least 9%, at least 10%, at least 12%, at least 12.5%, at least 15%, at least 20%, at least 25%, at least 30%, at least 50%, at least 60%, at least 70%, at least 75%, at least 80%, at least 95%, or at least 99% as compared to the stability, level, or ratio in the absence of the compound, the pharmaceutically acceptable salt, solvate, hydrate, tautomer, stereoisomer, or prodrug thereof.

In some embodiments, the method for inhibiting amyloid fibril formation or for treating an amyloid disease comprises administering the compound, the pharmaceutically acceptable salt, solvate, hydrate, tautomer, stereoisomer, or prodrug thereof, or the pharmaceutical preparation at a dosage effective to increase the ratio of tetrameric to monomeric TTR in the subject to at least 0.72, at least 0.75, at least 0.8, at least 0.85, at least 0.9, at least 0.95, at least 0.98, or at least 0.99, and/or to maintain such a ratio in the subject.

In some embodiments, the method for inhibiting amyloid fibril formation or for treating an amyloid disease comprises administering the compound, the pharmaceutically acceptable salt, solvate, hydrate, tautomer, stereoisomer, or prodrug thereof, or the pharmaceutical preparation in an amount effective to decrease the level of amyloid fibril formation by at least 5%, at least 10%, at least 15%, at least 20%, at least 25%, at least 30%, at least 40%, at least 50%, at least 60%, at least 70%, at least 75%, at least 80%, at least 90%, at least 95%, at least 95.7%, at least 98%, or at least 99% in the subject.

In some embodiments, the method for inhibiting amyloid fibril formation or for treating an amyloid disease further comprises administering at least one additional compound to the subject, wherein the at least one additional compound is approved for therapy of an amyloid disease. In some embodiments, the additional compound is Tafamidis, Tolcapone, Donepezil, Patisiran or Resuviran. In some embodiments, the method comprises administering the additional compound at the dosage commonly used for that compound when administered alone. In some embodiments, the additional compound is administered at a dosage below the dosage commonly used in single therapy with the compound. In some embodiments, both the compound, the pharmaceutically acceptable salt, solvate, hydrate, tautomer, stereoisomer, or prodrug thereof, or the pharmaceutical preparation described herein and the additional compound are administered at dosages that are below the maximum effective dose when administered alone.

In some embodiments, the method for inhibiting amyloid fibril formation or for treating an amyloid disease comprises identifying the subject as exhibiting an increased level of amyloid fibril formation as compared to a reference level or as having an amyloid disease. In some embodiments, the subject is identified as exhibiting an increased level of amyloid fibril formation as compared to a reference level, as having an amyloid disease, or as being at an above-average risk of developing an amyloid disease by performing an analysis of a sample obtained of the subject. In some embodiments, the sample is a body fluid, cell, or tissue sample obtained from the subject. In some embodiments, the analysis comprises detecting the presence of amyloid fibrils, a level of transthyretin expression, and/or a mutation in the transthyretin gene in the sample, analysis of abdominal fat, and/or imaging studies of the heart of the subject.

In some embodiments, the method for treating an amyloid disease is aimed to ameliorate an existing condition, for example, an existing amyloid disease in a subject. In some embodiments, the treatment is aimed to prevent a condition, e.g., an amyloid disease, or a symptom of such a condition, e.g., cognitive dysfunction or neuropathology, from occurring or from recurring. For example, in some embodiments, a compound, composition, or preparation as described herein is administered to a subject having an amyloid disease or exhibiting a decreased level of TTR in order to inhibit TTR amyloid fibril formation. For another example, in some embodiments, a compound, composition, or preparation as described herein is administered to a subject having an amyloid disease in addition to another clinical intervention to treat the amyloid disease, e.g., in addition to a liver transplant in a subject having a mutated TTR gene, in order to prevent or delay recurrence of the disease, e.g., via TTR from non-liver sources. In other embodiments, a compound, composition, or pharmaceutical preparation as described herein is administered to a subject not showing symptoms of an amyloid disease, such as cognitive dysfunction or neuropathology, but known to be predisposed or at an elevated risk to develop an amyloid disease, for example, based on familial history or genetic testing. In such embodiments, the administration may delay or prevent the onset of a symptom associated with an amyloid disease.

Some embodiments disclosed herein include a choice of treatment, referring to a selection of a clinical intervention from a number of alternatives, e.g., from the various compounds, compositions, or pharmaceutical preparations described herein, or further including additional treatment options for amyloid disease, e.g., treatment with Tafamidis or Donepezil, or via liver transplantation. In some embodiments, a choice of treatment involves the design of a personalized therapeutic approach for a subject having an amyloid disease based on the results from diagnostic methods. For example, in some embodiments, a choice of treatment includes administering to a subject having an amyloid disease a specific compound, composition, or pharmaceutical preparation described herein, based on a determination that the subject exhibits decreased TTR stability, e.g., as measured by a ratio of tetrameric to monomeric TTR in the plasma of the subject being below a threshold level indicating normal TTR stability, or based on determining that the subject carries a TTR mutation associated with an amyloid disease, e.g., by performing genetic analysis on a biological sample obtained from the subject. In some embodiments, a choice of treatment includes the determination of an appropriate treatment and dosage regimen. Some embodiments further include carrying out the selected treatment, e.g., by administering a compound, composition, or pharmaceutical preparation described herein according to an appropriate treatment and dosage regimen.

In some embodiments, the method of treating an amyloid disease comprises administering a compound, the pharmaceutically acceptable salt, solvate, hydrate, tautomer, stereoisomer, or prodrug thereof, or a pharmaceutical preparation as described herein at a dosage effective to ameliorate a symptom of the amyloid disease, e.g., a neuropathy, neurological impairment, neurological dysfunction, impairment of motor function, impairment of sensory function, impairment of memory, or cognitive deficiency in the subject. In some embodiments, the method further comprises monitoring at least one symptom associated with the amyloid disease in the subject during the treatment or after treatment has been administered. This may include, in some embodiments, testing motor function, sensory function, cognitive function, or memory function in the subject. While some exemplary symptoms of amyloid disease are described herein, other symptoms will be apparent to those of skill in the art. In addition, the skilled artisan will be able to identify suitable tests for monitoring such symptoms in a subject, e.g., by administering a suitable test for motor function, sensory function, cognitive function, or memory function in the subject. The disclosure is not limited in this respect.

The present disclosure is further illustrated by the following Examples, which are provided to illustrate some embodiments of this disclosure and are not to be construed as limiting. The entire contents of all of the references (including literature references, issued patents, published patent applications, and co-pending patent applications, if any) cited throughout this disclosure are hereby expressly incorporated by reference.

REFERENCES AND NOTES

[1] J. Toyn, What lessons can be learned from failed Alzheimer's disease trials?, Expert Rev. Clin. Pharmacol. 8 (2015) 1-3. doi:10.1586/17512433.2015.1034690.

[2] M. Ratner, Biogen's early Alzheimer's data raise hopes, some eyebrows, Nat. Biotech. 33 (2015) 438-438. doi:10.1038/nbt0515-438.

[3] R. M. M. Brito, A.M. Damas, M.J. Saraiva, Amyloid Formation by Transthyretin: From Protein Stability to Protein Aggregation, Curr. Med. Chem. Immun. Endoc. Metab. Agents. 3 (2003) 349-360.

[4] Y. Ando, T. Coelho, J. L. Berk, M. W. Cruz, B.-G. Ericzon, S. Ikeda, et al., Guideline of transthyretin-related hereditary amyloidosis for clinicians., Orphanet J. Rare Dis. 8 (2013) 31. http://www.pubmedcentral.nih.gov/articlerender.fcgi?artid=3584981&tool=pmcentrez&rendertype=abstract (accessed Mar. 31, 2015).

[5] C. E. Bulawa, S. Connelly, M. DeVit, L. Wang, C. Weigel, J. A. Fleming, et al., Tafamidis, a potent and selective transthyretin kinetic stabilizer that inhibits the amyloid cascade, Proc. Natl. Acad. Sci. 109 (2012) 9629-9634. doi:10.1073/pnas.1121005109.

[6] S. M. Johnson, S. Connelly, C. Fearns, E. T. Powers, J. W. Kelly, The transthyretin amyloidoses: from delineating the molecular mechanism of aggregation linked to pathology to a regulatory-agency-approved drug, J. Mol. Biol. 421 (2012) 185-203. doi:10.1016/j.jmb.2011.12.060.

[7] T. Coelho, L. F. Maia, M. Waddington, J. W. Kelly, J. Chan, J. Packman, Tafamidis for transthyretin familial amyloid polyneuropathy, (2012) 785-792.

[8] T. Coelho, L. F. Maia, M. Waddington, J. W. Kelly, J. Chan, J. Packman, Tafamidis for transthyretin familial amyloid polyneuropathy, Neurology. 79 (2012) 785-792.

[9] T. Coelho, L. F. Maia, A. M. Da Silva, M. W. Cruz, V. Plante-Bordeneuve, O. B. Suhr, et al., Long-term effects of tafamidis for the treatment of transthyretin familial amyloid polyneuropathy, J. Neurol. 260 (2013) 2802-2814. doi:10.1007/500415-013-7051-7.

[10] N. M. Beirão, E. Matos, I. Beirão, P. P. Costa, P. Torres, Recurrence of vitreous amyloidosis and need of surgical reintervention in portuguese patients with familial amyloidosis ATTR V30M, Retina. 31 (2011) 1373-1377. doi:10.1097/IAE.0b013e318203c0c2.

[11] L. F. Maia, R. Magalhaes, J. Freitas, R. Taipa, M. M. Pires, H. Osorio, et al., CNS involvement in V30M transthyretin amyloidosis: clinical, neuropathological and biochemical findings, J. Neurol. Neurosurg. Psychiatry. 86 (2014) 159-167. doi:10.1136/jnnp-2014-308107.

[12] L. F. Maia, I. R. A. Mackenzie, H. H. Feldman, Clinical phenotypes of Cerebral Amyloid Angiopathy, J. Neurol. Sci. 257 (2007) 23-30. doi:10.1016/j.jns.2007.01.054.

[13] R. Costa, A. Gonçalves, M. J. Saraiva, I. Cardoso, Transthyretin binding to A-Beta peptide-impact on A-Beta fibrillogenesis and toxicity, FEBS Lett. 582 (2008) 936-42. doi:10.1016/j.febslet.2008.02.034.

[14] R. Costa, F. Ferreira-da-Silva, M.J. Saraiva, I. Cardoso, Transthyretin protects against A-beta peptide toxicity by proteolytic cleavage of the peptide: a mechanism sensitive to the Kunitz protease inhibitor, PLoS One. 3 (2008) e2899. doi:10.1371/journal.pone.0002899.

[15] C. A. Ribeiro, M. J. Saraiva, I. Cardoso, Stability of the transthyretin molecule as a key factor in the interaction with a-beta peptide—relevance in Alzheimer's disease., PLoS One. 7 (2012) e45368. doi:10.1371/journal.pone.0045368.

[16] C. A. Ribeiro, S. M. Oliveira, L. F. Guido, A. Magalhães, G. Valencia, G. Arsequell, et al., Transthyretin stabilization by iododiflunisal promotes amyloid-β peptide clearance, decreases its deposition, and ameliorates cognitive deficits in an Alzheimer's disease mouse model., J. Alzheimers. Dis. 39 (2014) 357-70. http://www.ncbi.nlm.nih.gov/pubmed/24169237 (accessed Jun. 4, 2015).

[17] S. Nencetti, E. Orlandini, TTR fibril formation inhibitors: is there a SAR?, Curr. Med. Chem. 19 (2012) 2356-79. http://www.ncbi.nlm.nih.gov/pubmed/2247-1984.

[18] S. K. Palaninathan, N. N. Mohamedmohaideen, E. Orlandini, G. Ortore, S. Nencetti, A. Lapucci, et al., Novel transthyretin amyloid fibril formation inhibitors: synthesis, biological evaluation, and X-ray structural analysis, PLoS One. 4 (2009) e6290. doi:10.1371/journal.pone.0006290.

[19] M. M. Alhamadsheh, S. Connelly, A. Cho, N. Reixach, E. T. Powers, D. W. Pan, et al., Potent kinetic stabilizers that prevent transthyretin-mediated cardiomyocyte proteotoxicity, Sci. Transl. Med. 3 (2011) 97ra81. doi:10.1126/scitranslmed.3002473.

[20] C. J. V. Simões, T. Mukherjee, R. M. M. Brito, R. M. Jackson, Toward the Discovery of Functional Transthyretin Amyloid Inhibitors: Application of Virtual Screening Methods, J. Chem. Inf. Model. 50 (2010) 1806-1820. doi:10.1021/ci100250z.

[21] G. Ortore, A. Martinelli, Computational studies on transthyretin, Curr. Med. Chem. 19 (2012) 2380-7. http://www.ncbi.nlm.nih.gov/pubmed/22471985 (accessed Nov. 14, 2012).

[22] C. A. Lipinski, Experimental and Computational Approaches to Estimate Solubility and Permeability in Drug Discovery and Development Settings, Adv. Drug Deliv. Rev. 46 (2001) 3-26. doi:10.1016/S0169-409X(00)00129-0.

[23] J. E. Mills, P. M. Dean, Three-Dimensional Hydrogen-Bond Geometry and Probability Information from a Crystal Survey., J. Comput. Aided Mol. Des. 10 (1996) 607-622. http://www.ncbi.nlm.nih.gov/pubmed/9007693.

[24] D. F. Veber, S. R. Johnson, H.-Y. Cheng, B. R. Smith, K. W. Ward, K. D. Kopple, Molecular Properties That Influence the Oral Bioavailability of Drug Candidates, J. Med. Chem. 45 (2002) 2615-2623. http://www.ncbi.nlm.nih.gov/pubmed/12036371.

[25] Y. C. Martin, A bioavailability score, J. Med. Chem. 48 (2005) 3164-3170. doi:10.1021/jm0492002.

[26] W. J. Egan, K. M. Merz, J. J. Baldwin, Prediction of Drug Absorption Using Multivariate Statistics, J. Med. Chem. 43 (2000) 3867-3877. http://www.ncbi.nlm.nih.gov/pubmed/11052792.

[27] S. L. McGovern, B. T. Helfand, B. Feng, B. K. Shoichet, A Specific Mechanism of Nonspecific Inhibition, J. Med. Chem. 46 (2003) 4265-4272. doi:10.1021/jm030266r.

[28] J. Seidler, S. L. McGovern, T. N. Doman, B. K. Shoichet, Identification and Prediction of Promiscuous Aggregating Inhibitors Among Known Drugs., J. Med. Chem. 46 (2003) 4477-4486. doi:10.1021/jm030191r.

[29] H. M. Petrassi, T. Klabunde, J. Sacchettini, J. W. Kelly, Structure-Based Design of N-Phenyl Phenoxazine Transthyretin Amyloid Fibril Inhibitors, J. Am. Chem. Soc. 122 (2000) 2178-2192. doi:10.1021/ja993309v.

[30] G. M. Morris, D. S. Goodsell, R. S. Halliday, R. Huey, W. E. Hart, R. K. Belew, et al., Automated Docking Using a Lamarckian Genetic Algorithm and An Empirical Binding Free Energy Function, J. Comput. Chem. 19 (1998) 1639-1662. doi:10.1002/(SICI)1096-987X(19981115)19: 14<1639::AID-JCC10>3.0.CO; 2-B.

[31] T. Klabunde, H. M. Petrassi, V. B. Oza, P. Raman, J. W. Kelly, J. C. Sacchettini, Rational design of potent human transthyretin amyloid disease inhibitors, Nat. Struct. Biol. 7 (2000) 312-321. doi:10.1038/74082.

[32] H. E. Purkey, S. K. Palaninathan, K. C. Kent, C. Smith, S. H. Safe, J. C. Sacchettini, et al., Hydroxylated Polychlorinated Biphenyls Selectively Bind Transthyretin in Blood and Inhibit Amyloidogenesis: Rationalizing Rodent PCB Toxicity, Chem. Biol. 11 (2004) 1719-1728. doi:10.1016/j.chembiol.2004.10.009.

[33] C. E. Bulawa, S. Connelly, M. Devit, L. Wang, C. Weigel, J. a Fleming, et al., Tafamidis, a potent and selective transthyretin kinetic stabilizer that inhibits the amyloid cascade, Proc. Natl. Acad. Sci. USA. (2012). doi:10.1073/pnas.1121005109.

[34] S. M. Johnson, S. Connelly, I. A. Wilson, J. W. Kelly, Toward optimization of the linker substructure common to transthyretin amyloidogenesis inhibitors using biochemical and structural studies, J. Med. Chem. 51 (2008) 6348-58. doi:10.1021/jm800435s.

[35] L. A. Peterson, K. C. Naruko, D. P. Predecki, A reactive metabolite of furan, cis-2-butene-1,4-dial, is mutagenic in the Ames assay, Chem. Res. Toxicol. 13 (2000) 531-534. doi:10.1021/tx000065f.

[36] H. K. Hamadeh, S. Jayadev, E. T. Gaillard, Q. Huang, R. Stoll, K. Blanchard, et al., Integration of clinical and gene expression endpoints to explore furan-mediated hepatotoxicity, Mutat. Res. 549 (2004) 169-183. doi:10.1016/j.mrfmmm.2003.12.021.

[37] R. J. McMurtry, J. R. Mitchell, Renal and hepatic necrosis after metabolic activation of 2-substituted furans and thiophenes, including furosemide and cephaloridine, Toxicol. Appl. Pharmacol. 42 (1977) 285-300. doi:10.1016/0041-008X(77)90005-9.

[38] R. A. Wiley, G. J. Traiger, S. Baraban, L. M. Gammal, Toxicity-distribution relationships among 3-alkylfurans in mouse liver and kidney, Toxicol. Appl. Pharmacol. 74 (1984) 1-9. doi:10.1016/0300-483X(84)90128-8.

[39] J. R. Mitchell, W. Z. Potter, J. A. Hinson, D. J. Jollow, Hepatic necrosis caused by furosemide., Nature. 251 (1974) 508-511. doi:10.1038/251508a0.

[40] T. M. Alvarez-Diez, J. Zheng, Mechanism-Based Inactivation of Cytochrome P450 3A4 by 4-Ipomeanol, Chem. Res. Toxicol. 17 (2004) 150-157. doi:10.1021/tx0341431.

[41] H. H. J. Gerets, E. Hanon, M. Cornet, S. Dhalluin, O. Depelchin, M. Canning, et al., Selection of cytotoxicity markers for the screening of new chemical entities in a pharmaceutical context: A preliminary study using a multiplexing approach, Toxicol. Vitr. 23 (2009) 319-332. doi:10.1016/j.tiv.2008.11.012.

[42] S. Sassa, O. Sugita, R. A. Galbraith, A. Kappas, Drug metabolism by the human hepatoma cell, Hep G2, Biochem. Biophys. Res. Commun. 143 (1987) 52-57. doi: 10.1016/0006-291X(87)90628-0.

[43] H. E. Winberg, F. S. Fawcett, W. E. Mochel, C. W. Theobald, Dimethylenedihydroheteroaromatic Compounds and Heterocyclophanes by 1,6-Hofmann Elimination Reactions, J. Am. Chem. Soc. 82 (1960) 1428-1435. doi:10.1021/ja01491a037.

[44] L. M. Pevzner, Synthesis and Phosphorylation of 4-Functionalized 2-tert-Butyl-3-chloromethylfurans, Russ. J. Gen. Chem. 72 (2002) 1085-1089. doi:10.1023/A:1020750715942.

[45] J. K. Lawson, W. K. Easley, W. S. Wagner, W. S. Johnson, W. D. Wood, Tetrahydrothiophene, Org. Synth. 4, 36 (n.d.) 892, 89. http://www.orgsyn.org/Content/pdfs/procedures/CV4P0892.pdf.

[46] Z. Lai, W. Colon, J. W. Kelly, The acid-mediated denaturation pathway of transthyretin yields a conformational intermediate that can self-assemble into amyloid, Biochemistry. 35 (1996) 6470-82. http://www.ncbi.nlm.nih.gov/pubmed/8639594 (accessed Mar. 31, 2015).

[47] A. Velázquez-Campoy, H. Ohtaka, A. Nezami, S. Muzammil, E. Freire, Isothermal titration calorimetry, Curr. Protoc. Cell Biol. Chapter 17 (2004) Unit 17.8. doi:10.1002/0471143030.cb1708523.

[48] S. C. Penchala, S. Connelly, Y. Wang, M. S. Park, L. Zhao, A. Baranczak, et al., AG10 inhibits amyloidogenesis and cellular toxicity of the familial amyloid cardiomyopathy-associated V122I transthyretin, Proc. Natl. Acad. Sci. USA. 110 (2013) 9992-9997. doi:10.1073/pnas.1300761110.

[49] A. L. Hopkins, C. R. Groom, A. Alex, Ligand efficiency: A useful metric for lead selection, Drug Discov. Today. 9 (2004) 430-431. doi:10.1016/51359-6446(04)03069-7.

[50] C. Abad-Zapatero, J. T. Metz, Ligand efficiency indices as guideposts for drug discovery, Drug Discov. Today. 10 (2005) 464-469. doi:10.1016/51359-6446(05)03386-6.

[51] I. Cardoso, M. R. Almeida, N. Ferreira, G. Arsequell, G. Valencia, M. J. Saraiva, Comparative in vitro and ex vivo activities of selected inhibitors of transthyretin aggregation: relevance in drug design., Biochem. J. 408 (2007) 131-8. doi:10.1042/BJ20070689.

[52] M. R. Almeida, B. Macedo, I. Cardoso, I. Alves, G. Valencia, G. Arsequell, et al., Selective binding to transthyretin and tetramer stabilization in serum from patients with familial amyloidotic polyneuropathy by an iodinated diflunisal derivative, Biochem. J. 381 (2004) 351-356.

[53] R. Labaudiniere, Compounds, compositions and methods for stabilizing transthyretin and inhibiting transthyretin misfolding, U.S. Pat. No. 7,868,033, 2005.

[54] H. E. Winberg, F. S. Fawcett, W. E. Mochel, C. W. Theobald, Dimethylenedihydroheteroaromatic Compounds and Heterocyclophanes by 1,6-Hofmann Elimination Reactions, J. Am. Chem. Soc. 82 (1960) 1428-1435. doi:10.1021/ja01491a037.

[55] S. E. Whitney, M. Winters, B. Rickborn, Benzyneoxazole cycloadducts: isolation and retro-Diels-Alder reactions, J. Org. Chem. 55 (1990) 929-935. doi:10.1021/jo00290a025.

[56] A. Naganawa, Y. Ichikawa, M. Isobe, Synthetic studies on tautomycin synthesis of 2,3-disubstituted maleic anhydride segment, Tetrahedron. 50 (1994) 8969-8982. doi:10.1016/S0040-4020(01)85365-5.

[57] T. Q. Faria, Z. L. Almeida, P. F. Cruz, C. S. H. Jesus, P. Castanheira, R. M. M. Brito, A look into amyloid formation by transthyretin: aggregation pathway and a novel kinetic model., Phys. Chem. Chem. Phys. 17 (2015) 7255-63. http://www.ncbi.nlm.nih.gov/pubmed/25694367 (accessed Mar. 31, 2015).

[58] A. Raz, D. S. Goodman, The interaction of thyroxine with human plasma prealbumin and with the prealbumin-retinol-binding protein complex, J. Biol. Chem. 244 (1969) 3230-3237.

[59] J. O'Brien, I. Wilson, T. Orton, F. Pognan, Investigation of the Alamar Blue (resazurin) fluorescent dye for the assessment of mammalian cell cytotoxicity, Eur. J. Biochem. 267 (2000) 5421-5426. doi:10.1046/j.1432-1327.2000.01606.x.

INCORPORATION BY REFERENCE

All references recited in this document are incorporated herein in their entirety by reference, as if each and every reference had been incorporated by reference individually. In case of a conflict, the present disclosure will control.

EQUIVALENTS AND SCOPE

Those skilled in the art will recognize, or be able to ascertain using no more than routine experimentation, many equivalents to the specific embodiments of the disclosure described herein. The scope of the present disclosure is not intended to be limited to the above description, but rather is as set forth in the appended claims.

Where singular forms of elements or features are used in the specification of the claims, the plural form is also included, and vice versa, if not specifically excluded. For example, the term "a cell" or "the cell" also includes the plural forms "cells" or "the cells," and vice versa. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure also includes embodiments in which more than one, or all of the group members are present in, employed in, or otherwise relevant to a given product or process.

Furthermore, it is to be understood that the disclosure encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the disclosure, or aspects of the disclosure, is/are referred to as comprising particular elements, features, steps, etc., certain embodiments of the invention or aspects of the disclosure consist, or consist essentially of, such elements, features, steps, etc. For purposes of simplicity those embodiments have not been specifically set forth in haec verba herein. Thus for each embodiment of the invention that comprises one or more elements, features, steps, etc., the disclosure also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the disclosure, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

The following claims further set out particular embodiments of the disclosure.

ABBREVIATIONS

Abeta (Aβ), amyloid beta; AD, Alzheimer's disease; ALB, albumin; CAA, cerebral amyloid angiopathy; FAP, familial amyloid polyneuropathy; IEF, isoelectric focusing; ITC, isothermal titration calorimetry; LT, liver transplant; NSAID, non-steroidal anti-inflammatory drug; PMND, protein misfolding neurodegenerative disease; T4, thyroxine; TBG, thyroxine-binding globulin; TTR, transthyretin; VS, virtual screening.

The invention claimed is:
1. A compound of Formula (I):

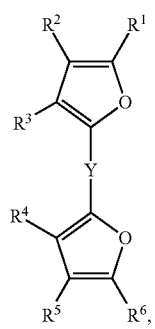

(I)

or pharmaceutically acceptable salt, solvate, hydrate, tautomer, stereoisomer, or prodrug thereof, wherein:
—Y— is —CH=CH— or —CH$_2$—CH$_2$—;
$R^1$ is H or —CH$_3$;
$R^2$ is —OR$^a$, —C(=O)OR$^a$, —S(=O)$_2$NHR$^a$, —S(=O)$_2$OR$^a$, —P(=O)NH$_2$(OR$^a$), —C(=O)N(R$^a$)$_2$, —C(=O)NHOR$^a$, or —CHN$_4$ (tetrazolyl);
$R^3$ is H or —CH$_3$;
$R^4$ is H, —OH, Halogen, —CH$_3$, or —OCH$_3$;
$R^5$ is H, F, —CN, —SH, —OR$^a$, —S(=O)$_2$NHR$^a$, —S(=O)$_2$OR$^a$, —P(=O)NH$_2$(OR$^a$), —C(=O)NHOR$^a$, or —CHN$_4$ (tetrazolyl);
$R^6$ is H, —OH, Halogen, —CH$_3$, or —OCH$_3$; and
each instance of R$^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two instances of R$^a$ are joined to form a substituted or unsubstituted, heterocyclic ring, or substituted or unsubstituted, heteroaryl ring.

2. The compound according to claim 1, wherein the compound is of the formula:

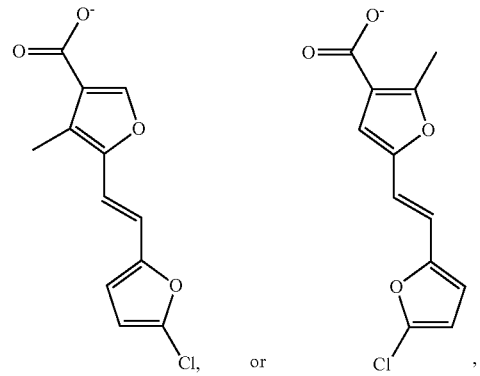 [SMILES: Cc1c(C(=O)[O-])coc1/C=C/c1ccc(Cl)o1 ; "or" ; Cc1oc(/C=C/c2ccc(Cl)o2)cc1C(=O)[O-] ; ","]

or pharmaceutically acceptable salt, solvate, hydrate, tautomer, stereoisomer, or prodrug thereof.

3. The compound of claim 1, or a pharmaceutically acceptable salt, solvate, hydrate, tautomer, stereoisomer, or prodrug thereof, wherein —Y— is —CH=CH—.

4. The compound according to claim 3, or pharmaceutically acceptable salt, solvate, hydrate, tautomer, stereoisomer, or prodrug thereof, wherein the C=C double bond connecting the two furan rings is of (E)-configuration.

5. The compound according to claim 3, or pharmaceutically acceptable salt, solvate, hydrate, tautomer, stereoisomer, or prodrug thereof, wherein the C=C double bond connecting the two furan rings is of (Z)-configuration.

6. The compound of claim 1, or a pharmaceutically acceptable salt, solvate, hydrate, tautomer, stereoisomer, or prodrug thereof, wherein $R^2$ is —C(=O)OR$^a$.

7. The compound of claim 1, or a pharmaceutically acceptable salt, solvate, hydrate, tautomer, stereoisomer, or prodrug thereof, wherein $R^4$ is H.

8. The compound of claim 1, or a pharmaceutically acceptable salt, solvate, hydrate, tautomer, stereoisomer, or prodrug thereof, wherein $R^5$ is H.

9. The compound of claim 1, or a pharmaceutically acceptable salt, solvate, hydrate, tautomer, stereoisomer, or prodrug thereof, wherein $R^6$ is halogen.

10. The compound of claim 1, or a pharmaceutically acceptable salt, solvate, hydrate, tautomer, stereoisomer, or prodrug thereof, wherein —Y— is —CH$_2$—CH$_2$—.

11. The compound of claim 1, or a pharmaceutically acceptable salt, solvate, hydrate, tautomer, stereoisomer, or prodrug thereof, wherein each instance of $R^a$ is H.

12. The compound of claim 1, or a pharmaceutically acceptable salt, tautomer, or stereoisomer thereof.

13. A pharmaceutical preparation comprising the compound according to claim 1, or a pharmaceutically acceptable salt, solvate, hydrate, tautomer, stereoisomer, or prodrug thereof, and a pharmaceutically acceptable carrier.

14. A method of inhibiting amyloid fibril formation in a subject, the method comprising administering to said subject an effective amount of a compound according to claim 1, or a pharmaceutically acceptable salt, solvate, hydrate, tautomer, stereoisomer, or prodrug thereof.

15. A method of ameliorating an amyloid disease, the method comprising administering to a subject in need thereof an effective amount of a compound of claim 1, or a pharmaceutically acceptable salt, solvate, hydrate, tautomer, stereoisomer, or prodrug thereof.

16. The method according to claim 15, wherein the amyloid disease is AA amyloidosis, Alzheimer's Disease, Light-Chain (AL) amyloidosis, Type-2 Diabetes, Medullary Carcinoma of the Thyroid, Parkinson's disease, Polyneuropathy, or Spongiform Encephalopathy.

17. The method according to claim 15, wherein the amyloid disease is Creutzfeldt Jakob disease.

18. The method according to claim 15, the method comprising administering to a subject in need thereof an effective amount of a compound of claim 1, or a pharmaceutically acceptable salt, tautomer, or stereoisomer thereof.

19. The method according to claim 15, wherein the amyloid disease is familial amyloid polyneuropathy.

20. The method according to claim 15, wherein the amyloid disease is familial amyloid cardiomyopathy.

21. The method according to claim 15, wherein the amyloid disease is senile systemic amyloidosis.

* * * * *